(12) United States Patent
Perez et al.

(10) Patent No.: US 10,266,708 B2
(45) Date of Patent: Apr. 23, 2019

(54) PRECURSOR COMPOUNDS FOR MOLECULAR COATINGS

(71) Applicant: aPEEL Technology, Inc., Santa Barbara, CA (US)

(72) Inventors: Louis Perez, Santa Barbara, CA (US); Chance Holland, Goleta, CA (US); James Rogers, Santa Barbara, CA (US); Stephen William Kaun, Santa Barbara, CA (US); Carlos Hernandez, Santa Barbara, CA (US); Charles Patrick Frazier, Goleta, CA (US)

(73) Assignee: Apeel Technology, Inc., Goleta, CA (US)

( * ) Notice: Subject to any disclaimer, the term of this patent is extended or adjusted under 35 U.S.C. 154(b) by 0 days.

(21) Appl. No.: 15/330,403

(22) Filed: Sep. 15, 2016

(65) Prior Publication Data

US 2017/0073532 A1    Mar. 16, 2017

Related U.S. Application Data

(60) Provisional application No. 62/219,372, filed on Sep. 16, 2015.

(51) Int. Cl.
| | |
|---|---|
| *C09D 7/63* | (2018.01) |
| *A01N 3/00* | (2006.01) |
| *A23B 5/06* | (2006.01) |
| *A23B 7/16* | (2006.01) |
| *A23B 9/14* | (2006.01) |

(52) U.S. Cl.
CPC ............ *C09D 7/63* (2018.01); *A01N 3/00* (2013.01); *A23B 5/06* (2013.01); *A23B 7/16* (2013.01); *A23B 9/14* (2013.01)

(58) Field of Classification Search
CPC .......... C09D 7/1233; C09D 7/63; A01N 3/00; A23B 5/06; A23B 7/16; A23B 9/14
See application file for complete search history.

(56) References Cited

U.S. PATENT DOCUMENTS

| | | |
|---|---|---|
| 1,016,761 A | 2/1912 | Moore |
| 2,213,557 A | 9/1940 | Tisdale |
| 2,222,000 A | 11/1940 | Julius |
| 2,275,659 A | 3/1942 | Steinle et al. |
| 2,324,448 A | 7/1943 | Gottlieb |
| 2,333,887 A | 11/1943 | Redlinger |
| 2,657,282 A | 10/1953 | Te |
| 3,232,765 A | 2/1966 | Rosenthal et al. |
| 3,997,674 A | 12/1976 | Ukai |
| 4,002,775 A | 1/1977 | Kabara |
| 4,421,775 A | 12/1983 | Chan, Jr. |
| 4,423,071 A | 12/1983 | Chignac et al. |
| 4,654,370 A | 3/1987 | Marriott, III et al. |
| 4,661,359 A | 4/1987 | Seaborne |
| 4,710,228 A | 12/1987 | Seaborne et al. |
| 4,732,708 A | 3/1988 | Ekman et al. |
| 4,962,885 A | 10/1990 | Coffee |
| 5,051,448 A | 9/1991 | Shashoua |
| 5,110,509 A | 5/1992 | Peter et al. |
| 5,126,153 A | 6/1992 | Beck |
| 2,363,232 A | 11/1994 | Witt |
| 5,376,391 A | 12/1994 | Nisperos |
| 5,389,389 A | 2/1995 | Beck |
| 5,607,970 A | 3/1997 | Ishihara et al. |
| 5,658,768 A | 8/1997 | Quinlan |
| 5,827,553 A | 10/1998 | Dimitroglou et al. |
| 5,832,527 A | 11/1998 | Kawaguchi |
| 5,906,831 A | 5/1999 | Larsson et al. |
| 5,925,395 A | 7/1999 | Chen |
| 5,939,117 A | 8/1999 | Chen et al. |
| 6,162,475 A | 12/2000 | Hagenmaier et al. |
| 6,165,529 A | 12/2000 | Yang |
| 6,241,971 B1 | 6/2001 | Fox et al. |
| 6,254,645 B1 | 7/2001 | Kellis, Jr. et al. |
| 6,255,451 B1 | 7/2001 | Koch et al. |
| 6,294,186 B1 | 9/2001 | Beerse et al. |
| 6,348,217 B1 | 2/2002 | Santos et al. |
| 6,503,492 B2 | 1/2003 | McGlone et al. |
| 7,375,135 B2 | 5/2008 | Najib-Fruchart et al. |
| 7,550,617 B2 | 6/2009 | Imig et al. |

(Continued)

FOREIGN PATENT DOCUMENTS

| | | |
|---|---|---|
| CN | 1215420 A | 4/1999 |
| CN | 1616561 A | 5/2005 |

(Continued)

OTHER PUBLICATIONS

Jerome et al. ("""One pot" and selective synthesis of monoglycerides over homogeneous and heterogeneous guanidine catalysts" Green Chem., 2004, 6, 72-74).*

(Continued)

*Primary Examiner* — Yong S. Chong
(74) *Attorney, Agent, or Firm* — Fenwick & West LLP

(57) ABSTRACT

Presented are compositions that can be used as protective coatings for agricultural (e.g., food) substrates. The compositions can comprise a compound of Formula I:

(Formula I)

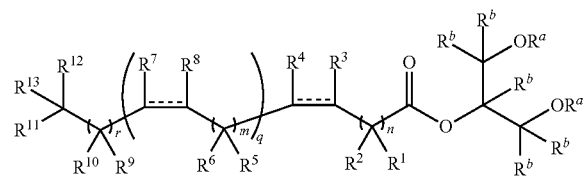

and an additive, wherein the variables m, n, q, r, $R^a$, $R^b$, $R^1$, $R^2$, $R^3$, $R^4$, $R^5$, $R^6$, $R^7$, $R^8$, $R^9$, $R^{10}$, $R^{11}$, $R^{12}$ and $R^{13}$ are defined herein. The protective coatings formed from the compositions can be used to prevent food spoilage due to, for instance, moisture loss, oxidation, or infection by a foreign pathogen.

25 Claims, 18 Drawing Sheets
(7 of 18 Drawing Sheet(s) Filed in Color)

(56) References Cited

U.S. PATENT DOCUMENTS

| | | | |
|---|---|---|---|
| 7,732,470 | B2 | 6/2010 | Imig et al. |
| 7,785,897 | B2 | 8/2010 | Agnes et al. |
| 7,851,002 | B2 | 12/2010 | Hekal et al. |
| 7,931,926 | B2 | 4/2011 | Lidster et al. |
| 7,943,336 | B2 | 5/2011 | Viksoe-Nielsen et al. |
| 8,101,221 | B2 | 1/2012 | Chen et al. |
| 8,119,178 | B2 | 2/2012 | Lidster et al. |
| 8,197,870 | B2 | 6/2012 | Krasutsky et al. |
| 8,247,609 | B2 | 8/2012 | Roques et al. |
| 8,263,751 | B2 | 9/2012 | Peterson |
| 8,424,243 | B1 | 4/2013 | Narciso et al. |
| 8,501,445 | B2 | 8/2013 | Yoshikawa et al. |
| 8,546,115 | B2 | 10/2013 | Buchert et al. |
| 8,609,169 | B2 | 12/2013 | Chen et al. |
| 8,752,328 | B2 | 6/2014 | Kaiser et al. |
| 8,846,355 | B2 | 9/2014 | Yoshikawa et al. |
| 9,095,152 | B2 | 8/2015 | Munger et al. |
| 9,102,125 | B2 | 8/2015 | Battersby et al. |
| 9,284,432 | B2 | 3/2016 | Yoshikawa et al. |
| 9,744,542 | B2 | 8/2017 | Rogers |
| 9,770,041 | B2 | 9/2017 | Dong et al. |
| 10,092,014 | B2 | 10/2018 | Holland et al. |
| 2001/0042341 | A1 | 11/2001 | Hamersky |
| 2002/0043577 | A1 | 4/2002 | Krasutsky et al. |
| 2004/0022906 | A1 | 2/2004 | Petacvich |
| 2004/0120919 | A1 | 6/2004 | Nguyen et al. |
| 2004/0220283 | A1 | 11/2004 | Zhang et al. |
| 2005/0233039 | A1 | 10/2005 | Wolfe et al. |
| 2007/0278103 | A1 | 12/2007 | Hoerr et al. |
| 2008/0026120 | A1 | 1/2008 | Petcavich |
| 2008/0038471 | A1 | 2/2008 | Boger et al. |
| 2008/0254987 | A1 | 10/2008 | Liu et al. |
| 2008/0262190 | A1 | 10/2008 | Koskimies et al. |
| 2008/0310991 | A1 | 12/2008 | Webster et al. |
| 2009/0104446 | A1 | 4/2009 | Guillet et al. |
| 2009/0142453 | A1 | 6/2009 | Lobisser et al. |
| 2009/0152371 | A1 | 6/2009 | Stark et al. |
| 2009/0325240 | A1 | 12/2009 | Daniell |
| 2010/0029778 | A1 | 2/2010 | Bailey et al. |
| 2010/0186674 | A1 | 7/2010 | Cahill, Jr. et al. |
| 2010/0210745 | A1 | 8/2010 | McDaniel |
| 2010/0278784 | A1 | 11/2010 | Pojasek et al. |
| 2010/0292426 | A1 | 11/2010 | Hossainy |
| 2011/0240064 | A1 | 10/2011 | Wales |
| 2011/0244095 | A1 | 10/2011 | Sardo |
| 2011/0280942 | A1 | 11/2011 | Schad et al. |
| 2012/0003356 | A1 | 1/2012 | Ekanayake et al. |
| 2012/0251675 | A1 | 10/2012 | Sowa et al. |
| 2013/0209617 | A1 | 8/2013 | Lobisser et al. |
| 2013/0216488 | A1 | 8/2013 | Hernandez-Brenes et al. |
| 2014/0033926 | A1 | 2/2014 | Fassel et al. |
| 2014/0199449 | A1 | 7/2014 | Hernandez et al. |
| 2014/0205722 | A1 | 7/2014 | Quintanar Guerrero et al. |
| 2014/0221308 | A1 | 8/2014 | Baker et al. |
| 2014/0234921 | A1 | 8/2014 | Nyyssola et al. |
| 2014/0348945 | A1 | 11/2014 | Dong et al. |
| 2015/0030780 | A1 | 1/2015 | Rogers |
| 2015/0079248 | A1 | 3/2015 | Nussinovitch et al. |
| 2016/0002483 | A1 | 1/2016 | Zhao et al. |
| 2016/0213030 | A1 | 7/2016 | Schad |
| 2016/0256429 | A1 | 9/2016 | Spanova et al. |
| 2016/0324172 | A1 | 11/2016 | Williams et al. |
| 2017/0049119 | A1 | 2/2017 | Perez et al. |
| 2017/0073532 | A1 | 3/2017 | Perez et al. |
| 2017/0332650 | A1 | 11/2017 | Holland |
| 2018/0044276 | A1 | 2/2018 | Perez et al. |
| 2018/0092811 | A1 | 4/2018 | Klee |

FOREIGN PATENT DOCUMENTS

| | | |
|---|---|---|
| CN | 101035926 A | 9/2007 |
| CN | 101356012 A | 1/2009 |
| CN | 102291986 A | 12/2011 |
| CN | 102335142 A | 2/2012 |
| CN | 103283830 A | 9/2013 |
| CN | 103719261 | 4/2014 |
| DE | 25 05 428 | 8/1976 |
| DE | 36 22 191 | 1/1988 |
| EP | 0104043 | 3/1984 |
| EP | 1020124 A2 | 7/2000 |
| EP | 2389814 | 11/2011 |
| JP | 62-126931 | 6/1967 |
| JP | S54-139645 A | 10/1979 |
| JP | S58-034034 A | 2/1983 |
| JP | S63-062574 A | 3/1988 |
| JP | H04-507192 T | 12/1992 |
| JP | 2002-531075 T | 9/2002 |
| JP | 2008-504442 T | 2/2008 |
| JP | 2009-527357 T | 7/2009 |
| JP | 2012-515561 T | 7/2012 |
| WO | WO 93/06735 | 4/1993 |
| WO | WO2001001980 | 1/2001 |
| WO | WO2004030455 | 4/2004 |
| WO | WO 2009/119730 | 10/2009 |
| WO | WO 2011/014831 | 2/2011 |
| WO | WO2012042404 | 4/2012 |
| WO | WO 2014/206911 | 12/2014 |
| WO | WO 2015/017450 | 2/2015 |
| WO | WO2015028299 | 3/2015 |
| WO | WO2015052433 | 4/2015 |
| WO | WO 2015/176020 | 11/2015 |
| WO | WO 2016/168319 | 10/2016 |
| WO | WO 2016/187581 | 11/2016 |
| WO | WO 2017/048951 | 3/2017 |
| WO | WO 2017/100636 | 6/2017 |
| WO | WO 2017/132281 | 8/2017 |

OTHER PUBLICATIONS

Andrade et al. "Atomizing spray systems for application of edible coatings", *Comprehensive Reviews in Food Science and Food Safety*, vol. 11, No. 3, 2012, pp. 323-337.

Ayala-Zavala, J.F. et al., "High Relative Humidity In-Package of Fresh-Cut Fruits and Vegetables: Advantage or Disadvantage Considering Microbiological Problems and Antimicrobial Delivering Systems?", 2008, *J. Food Science*, vol. 73, p. R41-R47.

Ben-Yehoshua S. et al. "Modified-atmosphere packaging of fruits and vegetables: reducing condensation of water in bell peppers and mangoes", 1998, *Acta Hort (ISHS)*, vol. 464, p. 387-92.

Bourtoom, T., "Edible films and coatings: characteristics and properties", *International Food Research Journal*, 2008, vol. 15, No. 3, pp. 237-248.

Deell Jr et al. "Addition of sorbitol with $KMnO_4$ improves broccoli quality retention in modified atmosphere packages", 2006, *J Food Qual*, vol. 29, p. 65-75.

Elgimabi and Ahmed, "Effects of Bactericides and Sucrose-Pulsing on Vase Life of Rose Cut Flowers (*Rosa hybirida*)", 2009, *Botany Research International*, 2(3) pp. 164-168.

He et al. "Stem end blockage in cut *Grevillea* 'Crimson Yul-lo' inflorescences", *Postharvest Biology and Technology*, 2006, vol. 41, pp. 78-84.

Hojjati et al. "Chemical Treatments of *Eustoma* Cut Flower Cultivars for Enhanced Vase Life", 2007, *Journal of Agriculture and Social Sciences*, vol. 3, No. 3, pp. 75-78.

Javad et al. "Postharvest evaluation of vase life, stem bending and screening of cultivars of cut gerbera (*Gerbera jamesonii* Bolux ex. Hook f.) flowers", *African Journal of Biotechnology* 2011, 10(4), pp. 560-566.

Javad et al. "Effect of Cultivar on Water Relations and Postharvest Quality of Gerbera (*Gerbera jamesonii* Bolus ex. Hook f.) Cut Flower", 2012, *World Applied Sciences Journal* vol. 18, No. 5, pp. 698-703.

Jones et al. "Pulsing with Triton X-100 Improves Hydration and Vase Life of Cut Sunflowers (*Helianthus annuus* L.)", 1993, *HortScience*, vol. 28, No. 12, pp. 1178-1179.

Roy, et al. "Modified atmosphere and modified humidity packaging of fresh mushrooms" 1996, *J Food Sci.*, vol. 61, p. 391-7.

Shirazi A, et al. "Controlling relative humidity in modified atmosphere packages of tomato fruit", 1992, *HortScience*, vol. 27, p. 336-9.

(56) References Cited

OTHER PUBLICATIONS

Steuter et al. "Water Potential of Aqueous Polyethylene Glycol", 1981, *Plant Physiol.*, vol. 67 pp. 64-67.
Van Doorn et al. "Effects of surfactants on the longevity of dry-stored cut flowering stems of rose, *Bouvardia*, and *Astilbe*", 1993, *Postharvest Biology and Technology*, vol. 3, pp. 69-76.
Van Doorn et al. "Alkylethoxylate surfactants for rehydration of roses and *Bouvardia* flowers", 2002, *Postharvest Biology and Technology*, vol. 24, pp. 327-333.
Van Meeteren, "Water Relations and Keeping-Quality of Cut Gerbera Flowers. I. The Cause of Stem Break", 1978, *Scientia Horticulturae*, vol. 8, pp. 65-74.
Mattson and Volpenhein. Synthesis and properties of glycerides. *J. Lipid Research*, (1962) 3(3) pp. 281-296.
Tanaka et al. Quantitative determination of isomeric glycerides, free fatty acids and triglycerides by thin layer chromatography-flame ionization detector system. *Lipids*, (1980) 15(10) pp. 872-875.
Bewick, T., et al. "Evaluation of Epicuticular Wax Removal from Whole Leaves with Chloroform," Weed Technology, Jul.-SePages, 1993, vol. 7, No. 3, pp. 706-716.
Cantwell, M., "Properties and recommended conditions for long-term storage of fresh fruits and vegetables," Nov. 2001, 8 Pages.
Cochran, H.D. "Solvation in supercritical water", Fluid Phase Equilibria, 1992, vol. 71, pp. 1-16.
Gabler, M., et al. "Impact of Postharvest Hot Water or Ethanol Treatment of Table Grapes on Gray Mold Incidence, Quality, and Ethanol Content," Plant Disease, Mar. 2005, vol. 89, No. 3, pp. 309-316.
Gil, M. et al. "Fresh-cut product sanitation and wash water disinfection: Problems and solutions", International Journal of Food Microbiology, 2009, vol. 134, pp. 37-45.
Graca, J. et al., "Linear and branched poly (omega-hydroxyacid) esters in plant cutins," J. Agric. Food Chem., 2010, vol. 58, No. 17, pp. 9666-9674.
Hardenburg, R., et al., "The Commercial Storage of Fruits, Vegetables, and Florist and Nursery Stocks," United States Department of Agriculture, Agriculture Handbook No. 66, Sep. 1986, pp. 6-7, 30, 50-51.
Hauff, S. et al. "Determination of hydroxylated fatty acids from the biopolymer of tomato cutin and their fate during incubation in soil," Phytochemical Analysis, Aug. 26, 2010, vol. 21, No. 6, pp. 582-589.
Holcroft, D., "Water Relations in Harvested Fresh Produce," PEF White Paper No. 15-01, The Postharvest Education Foundation (PEF), May 2015, 16 Pages.
Jerome, F., et al. ""One pot" and selective synthesis of monoglycerides over homogeneous and heterogeneous guanidine catalysts" Green Chem., 2004, vol. 6, pp. 72-74.
Karabulut, O. et al. "Postharvest ethanol and hot water treatments of table grapes to control gray mold", Postharvest Biology and Technology, 2004, vol. 34, pp. 169-177.
Kolattukudy, P.E., "Cutin from plants," Biopolymers Online, 3a, 2005, 40 pages.
Krammer, P., et al. "Hydrolysis of esters in subcritical and supercritical water", Journal of Supercritical Fluids, 2000, vol. 16, pp. 189-206.
Loppinet-Serani, A. et al. "Supercritical water for environmental technologies", J Chem Technol Biotechnol, Jan. 12, 2010, vol. 85, pp. 583-589.
Matic, M., "The chemistry of Plant Cuticles: a study of cutin form *Agave americana* L.," 1956, Biochemical Journal, 1956, vol. 63, No. 1, pp. 168-176.
Morton, H. "The Relationship of Concentration and Germicidal Efficiency of Ethyl Alcohol", Annals New York Academy of Sciences, 53(1), 1950, pp. 191-196.
Oh, D. et al. "Antimicrobial activity of ethanol, glycerol monolaurate or lactic acid against Listeria monocytogenes", International Journal of Food Microbiology, 1993, vol. 20, pp. 239-246.
Olmez, H. et al. "Potential alternative disinfection methods for organic fresh-cut industry for minimizing water consumption and environmental impact", LWT—Food Science and Technology, 2009, vol. 42, pp. 686-693.
Osman, S. F., et al., "Preparation, Isolation, and Characterization of Cutin Monomers and oligomers from Tomato Peels," J. Agric, Food Chem, 1999, vol. 47, No. 2, pp. 799-802.
Rutala, W. et al. "Guideline for Disinfection and Sterilization in Healthcare Facilities, 2008" CDC, 2008, 158 Pages.
Sasaki, M., et al. "Cellulose hydrolysis in subcritical and supercritical water", Journal of Supercritical Fluids, 1998, vol. 13, pp. 261-268.
Sasaki, M., et al. "Dissolution and Hydrolysis of Cellulose in Subcritical and Supercritical Water", Ind. Eng. Chem. Res., 2000, vol. 39, pp. 2883-2890.
Savage, P., "Organic Chemical Reactions in Supercritical Water", Chem. Rev., 1999, vol. 99, pp. 603-621.
Schreiber, L., "Transport barriers made of cutin, suberin and associated waxes", Trends in Plant Science, 2010, vol. 15, No. 10, pp. 546-553.
Schweizer, P., et al. "Perception of free cutin monomers by plant cells", The Plant Journal, 1996, vol. 10, No. 2, pp. 331-341.
Schweizer, P., et al. "Plant Protection by Free Cutin Monomers in Two Cereal Pathosystems", Advances in Molecular Genetics of Plant-Microbe Interactions, 1994, pp. 371-374.
Weingartner, H., et al. "Supercritical water as a solvent", Angewandte Chemie, 2005, vol. 44, Issue 18, pp. 2672-2692.
Yeats, T., et al. "The identification of cutin synthase: formation of the plant polyester cutin," Nat Chem Biol. Jul. 2012, vol. 8, No. 7, pp. 609-611.
PCT International Search Report and Written Opinion for PCT/US2016/065917, dated Mar. 9, 2017, 10 Pages.
PCT International Search Report and Written Opinion for PCT/US2017/014978, dated Apr. 10, 2017, 13 Pages.
PCT International Search Report and Written Opinion for PCT/US2016/051936, dated Jan. 31, 2017, 18 Pages.
Alvaro, J. et al. "Effects of peracetic acid disinfectant on the postharvest of some fresh vegetables", Journal of Food Engineering, 2009, vol. 95, pp. 11-15.
Banerjee, S., et al., "Review Article: Electrospray Ionization Mass Spectrometry: A Technique to Access the Information Beyond the Molecular Weight of the Analyte," International Journal of Analytical Chemistry, Nov. 2011, vol. 2012, Article ID 282574, 40 pages.
Bateman, A., et al., "The Effect of Solvent on the Analysis of Secondary Organic Aerosol Using Electrospray Ionization Mass Spectrometry," Environ. Sci. Technol., 2008, vol. 42, No. 19, pp. 7341-7346.
Bateman, A., et al, "Supporting Information for Manuscript es-2008-01226w—The Effect of Solvent on the Analysis of Secondary Organic Aerosol Using Electrospray Ionization Mass Spectrometry," [online] 2008; available from the Internet URL: http://aerosol.chem.uci.edu/publications/Irvine/2008.sub.--Bateman.sub.--- Est.sub.--SOA.sub.--solvent.sub.--effects.sub.--supporting.sub.--info.pdf, 6 pages.
Cech, N., et al., "Practical Implications of Some Recent Studies in Electrospray Ionization Fundamentals," Mass Spectrometry Reviews, 2001, vol. 20, pp. 362-387.
Chen, D-R., et al., "Electrospraying of Conducting Liquids for Monodisperse Aerosol Generation in the 4 nm to 1.8 .mu.m Diameter Range," J. Aerosol Sci., 1995, vol. 26, No. 6, pp. 963-977.
Enke, C., "A Predictive Model for Matrix and Analyte Effects in Electrospray Ionization of Singly-charged Ionic Analytes," Analytical Chemistry, 1997, vol. 69, No. 23, pp. 4885-4893.
Gaskell, S., "Special Feature: Tutorial—Electrospray: Principles and Practice," J. Mass Spectrom, 1997, vol. 32, pp. 677-688.
Huang, T-Y., et al., "Electron Transfer Reagent Anion Formation via Electrospray Ionization and Collision-induced Dissociation," Anal Chem., 2006, vol. 78, No. 21, pp. 7387-7391.
Huang, N., et al., "Automation of a Fourier Transform Ion Cyclotron Resonance Mass Spectrometer for Acquisition, Analysis, and E-mailing of High-resolution Exact-mass Electrospray Ionization Mass Spectral Data," J. Am Soc Mass Spectrom, 1999, vol. 10, pp. 1166-1173.

(56) References Cited

OTHER PUBLICATIONS

Jaworek, A., "Electrospray Droplet Sources for Thin Film Deposition," J. Mater Sci, 2007, vol. 42, pp. 266-297.
Kebarle, P., "Special Feature: Commentary—A Brief Overview of the Present Status of the Mechanisms Involved in Electrospray Mass Spectrometry," J. Mass Spectrom, 2000, vol. 35, pp. 804-817.
Keller, B., et al., "Review Article: Interferences and Contaminants Encountered in Modern Mass Spectrometry," Analytica Chimica Acta, 2008, vol. 627, pp. 71-81.
Kroll, B., et al., "Review: Chemistry of Secondary Organic Aerosol: Formation and Evolution of Low-volatility Organics in the Atmosphere," Atmospheric Environment, 2008, vol. 42, pp. 3593-3624.
Li, M.,et al., "Direct Quantification of Organic Acids in Aerosols by Desorption Electrospray Ionization Mass Spectrometry," Atmospheric Environment, 2009, vol. 43, pp. 2717-2720.
Nizkorodov, S., et al., "Molecular Chemistry of Organic Aerosols through the Application of High Resolution Mass Spectrometry," Phys. Chem. Chem. Phys, 2011, vol. 13, pp. 3612-3629.
Takats, Z., et al., "Special Feature: Perspective—Ambient Mass Spectrometry Using Desorption Electrospray Ionization (DESI): Instrumentation, Mechanisms and Applications in Forensics, Chemistry, and Biology," J. Mass Spectrom, 2005, vol. 40, pp. 1261-1275.
Wang, R., et al., "Evolution of the Solvent Polarity in an Electrospray Plume," J. Am Soc Mass Spectrom, 2010, vol. 21, pp. 378-385.
Wikipedia, Anonymous "Paint-Wikipedia", Jul. 2013, 7 Pages. https://en.wikipedia.org/w/index.php?title=Paint&oldid=563291624.
Zhu, J., et al., "Focus: Electrospray—Formation and Decompositions of Chloride Adduct Ions, [M+Cl], in Negative Ion Electrospray Ionization Mass Spectrometry," J. Am Soc Mass Spectrom, 2000, vol. 11, pp. 932-941.
Zhu, J., et al., "Ranking of a Gas-phase Acidities and Chloride Affinities of Monosaccharides and Linkage Specificity in Collision-induced Decompositions of Negative Ion Electrospray-generated Chloride Adducts of Oligosaccharides," J. Am Soc Mass Spectrom, 2001, vol. 12, pp. 1193-1204.
PCT International Search Report and Written Opinion in PCT/US2014/048707, dated Nov. 13, 2014, 12 pages.
PCT International Search Report and Written Opinion in PCT/US2017/024799, dated Jun. 8, 2017, 13 pages.
PCT International Search Report and Written Opinion in PCT/US2017/041167, dated Oct. 9, 2017, 20 pages.
Extended European Search Report for European Patent Application No. EP 14831592.2, dated Mar. 2, 2017, 9 Pages.
First Office Action for Chinese Patent Application No. CN 201480050446.3, dated Jun. 4, 2018, 30 Pages.
Notice of Reasons for Rejection for Japanese Patent Application No. JP 2016-531832, dated Jul. 3, 2018, 13 Pages.
Hudson, B., "Fatty Acids," Encyclopedia of Food Sciences and Nutrition (Second Edition), 2003, pp. 2297-2300.
First Office Action for Chinese Patent Application No. CN 201480050446.3, dated Jun. 4, 2018, 28 Pages.
Kolattukudy, P.E., "Biopolyester Membranes of Plants: Cutin and Suberin," Science, 1980, vol. 208, No. 4447, pp. 990-1000.
PCT International Search Report and Written Opinion, PCT Application No. PCT/US2018/46994, dated Dec. 20, 2018, 31 pages.
Tegelaar, E.W. et al., "Some mechanisms of flash pyrolysis of naturally occurring higher plant polyesters," Journal of Analytical and Applied Pyrosis, 1989, vol. 15, 2 pages (abstract only).
United States Office Action, U.S. Appl. No. 16/121,518, dated Oct. 18, 2018, 11 pages.
United States Office Action, U.S. Appl. No. 16/151,268, dated Dec. 14, 2018, 11 pages.
Xizhong, W. et al., "Spray drying", the 2nd edition, Chemical Industry Press, Feb. 28, 2003, pp. 147-151.

\* cited by examiner

PRECURSOR COMPOUNDS FOR MOLECULAR COATINGS

RELATED APPLICATIONS

This application claims the benefit under 35 U.S.C § 119(e) of U.S. Provisional Patent Application Ser. No. 62/219,372, filed Sep. 16, 2015, the disclosure of which is incorporated herein by reference in its entirety.

TECHNICAL FIELD

The present disclosure relates to compositions that can be used to form protective coatings on a substrate. The disclosure also relates to the protective coatings themselves.

BACKGROUND

Common agricultural products are susceptible to degradation and decomposition (i.e., spoilage) when exposed to the environment. Such agricultural products can include, for example, eggs, fruits, vegetables, produce, seeds, nuts, flowers, and/or whole plants (including their processed and semi-processed forms). Nun-agricultural products (e.g., vitamins, candy, etc.) are also vulnerable to degradation when exposed to the ambient environment. The degradation of the agricultural products can occur via abiotic means as a result of evaporative moisture loss from an external surface of the agricultural products to the atmosphere and/or oxidation by oxygen that diffuses into the agricultural products from the environment and/or mechanical damage to the surface and/or light-induced degradation (i.e., photodegradation). Furthermore, biotic stressors such as, for example, bacteria, fungi, viruses, and/or pests can also infest and decompose the agricultural products.

Conventional approaches to preventing degradation, maintaining quality, and increasing the life of agricultural products include refrigeration and/or special packaging. Refrigeration can require capital-intensive equipment, demands constant energy expenditure, can cause damage or quality loss to the product if not carefully controlled, must be actively managed, and its benefits can be lost upon interruption of a temperature-controlled supply chain. Special packaging can also require expensive equipment, consume packaging material, increase transportation costs, and require active management. Despite the benefits that can be afforded by refrigeration and special packaging, the handling and transportation of the agricultural products can cause surface abrasion or bruising that is aesthetically displeasing to the consumer and serves as points of ingress for bacteria and fungi. Moreover, the expenses associated with such approaches can add to the cost of the agricultural product.

The cells that form the aerial surface of most plants (such as higher plants) include an outer envelope or cuticle, which provides varying degrees of protection against water loss, oxidation, mechanical damage, photodegradation, and/or biotic stressors, depending upon the plant species and the plant organ (e.g., fruit, seeds, bark, flowers, leaves, stems, etc.). Cutin, which is a biopolyester derived from cellular lipids, forms the major structural component of the cuticle and serves to provide protection to the plant against environmental stressors (both abiotic and biotic). The thickness, density, as well as the composition of the cutin (i.e., the different types of monomers that form the cutin and their relative proportions) can vary by plant species, by plant organ within the same or different plant species, and by stage of plant maturity. The cutin-containing portion of the plant can also contain additional compounds (e.g., epicuticular waxes, phenolics, antioxidants, colored compounds, proteins, polysaccharides, etc.). This variation in the cutin composition as well as the thickness and density of the cutin layer between plant species and/or plant organs and/or a given plant at different stages of maturation can lead to varying degrees of resistance between plant species or plant organs to attack by environmental stressors (i.e., water loss, oxidation, mechanical injury, and light) and/or biotic stressors (e.g., fungi, bacteria, viruses, insects, etc.).

SUMMARY

Described herein are compositions that can be used to form protective coatings on substrates. The coatings can be used to protect the substrates, e.g., food and/or agricultural products, from spoilage and/or decomposition due to factors such as moisture loss, oxidation, mechanical degradation, photodegradation, and fungal growth. The compositions can be made from monoacylglycerides similar to those that also make up the cutin layer of the plant cuticle.

Accordingly, in one aspect of the present disclosure, a composition comprises a 2-monoacylglyceride compound of the Formula I:

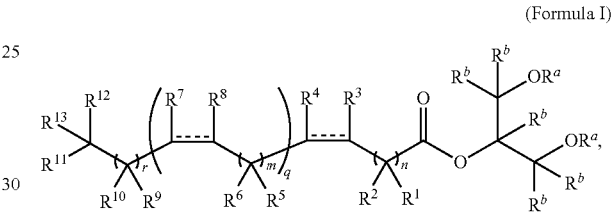

(Formula I)

wherein:

each $R^a$ is independently —H or —$C_1$-$C_6$alkyl;

each $R^b$ is independently selected from —H, —$C_1$-$C_6$alkyl, or —OH;

$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen;

$R^3$, $R^4$, $R^7$, and $R^8$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl wherein each alkyl, alkynyl, cycloalkyl, aryl, or heteroaryl is optionally substituted with one or more —$OR^{14}$, —$NR^{14}R^{15}$, —$SR^{14}$, or halogen; or $R^3$ and $R^4$ can combine with the carbon atoms to which they are attached to form a $C_3$-$C_6$ cycloalkyl, a $C_4$-$C_6$cycloalkenyl, or 3- to 6-membered ring heterocycle; and/or $R^7$ and $R^8$ can combine with the carbon atoms to which they are attached to form a $C_3$-$C_6$ cycloalkyl, a $C_4$-$C_6$cycloalkenyl, or 3- to 6-membered ring heterocycle;

$R^{14}$ and $R^{15}$ are each independently, at each occurrence, —H, —$C_1$-$C_6$alkyl, —$C_2$-$C_6$alkenyl, or —$C_2$-$C_6$alkynyl;

the symbol ══════ represents a single bond or a cis or trans double bond;

n is 0, 1, 2, 3, 4, 5, 6, 7 or 8;

m is 0, 1, 2 or 3;

q is 0, 1, 2, 3, 4 or 5; and r is 0, 1, 2, 3, 4, 5, 6, 7 or 8; and an additive;

wherein a mass ratio (or a molar ratio) of the additive to the compound of Formula I is in a range of about 0.1 to about 1.

The additive of any of the compositions described herein can be any organic compound, including 1-monoacylglycerides, fatty acids, esters, amides, amines, thiols, carboxylic acids, ethers, aliphatic waxes, alcohols, salts (inorganic and organic), or combinations thereof.

In one or more embodiments, the additive is a 1-monoacylglyceride compound of Formula II:

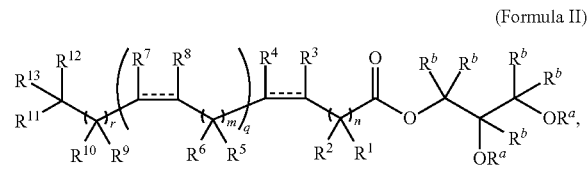

(Formula II)

wherein:
each $R^a$ is independently —H or —$C_1$-$C_6$alkyl;
each $R^b$ is independently selected from —H, —$C_1$-$C_6$alkyl, or —OH;
$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl, wherein each alkyl, alkenyl, alkynyl, cycloalkyl, $_0$aryl, or heteroaryl is optionally substituted with one or more —$OR^{14}$, —$NR^{14}R^{15}$, —$SR^{14}$, or halogen;
$R^3$, $R^4$, $R^7$, and $R^8$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen; or
$R^3$ and $R^4$ can combine with the carbon atoms to which they are attached to form a $C_3$-$C_6$ cycloalkyl, a $C_4$-$C_6$cycloalkenyl, or 3- to 6-membered ring heterocycle; and/or
$R^7$ and $R^8$ can combine with the carbon atoms to which they are attached to form a $C_3$-$C_6$ cycloalkyl, a $C_4$-$C_6$cycloalkenyl, or 3- to 6-membered ring heterocycle;
$R^{14}$ and $R^{15}$ are each independently, at each occurrence, —H, —$C_1$-$C_6$alkyl, —$C_2$-$C_6$alkenyl, or —$C_2$-$C_6$alkynyl;
the symbol ⁼⁼⁼⁼⁼⁼ represents a single bond or a cis or trans double bond;
n is 0, 1, 2, 3, 4, 5, 6, 7 or 8;
m is 0, 1, 2 or 3;
q is 0, 1, 2, 3, 4 or 5; and
r is 0, 1, 2, 3, 4, 5, 6, 7 or 8.

In another aspect of the present disclosure, a solution comprises a compound Formula I and an additive (e.g., a compound of Formula II), wherein the molar ratio or mass ratio of the additive to the compound of Formula I is in a range of 0.1 to 1, and wherein the additive and the compound of Formula I are dissolved in a solvent at a concentration of at least about 0.5 mg/mL.

In another aspect, the present disclosure provides for the use of a composition comprising Formula I and an additive (e.g., a compound of Formula II) to prevent spoilage of an agricultural substrate (e.g., a food).

In another aspect of the present disclosure, a composition includes a compound of Formula I:

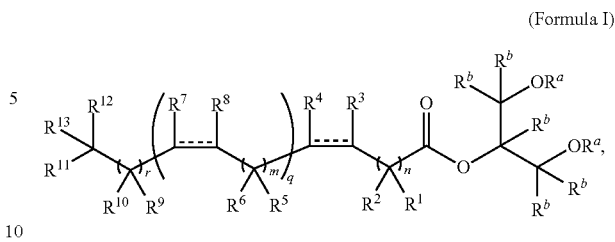

(Formula I)

wherein:
each $R^a$ is independently —H or —$C_1$-$C_6$alkyl;
each $R^b$ is independently selected from —H, —$C_1$-$C_6$alkyl, or —OH;
$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen;
$R^3$, $R^4$, $R^7$, and $R^8$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl wherein each alkyl, alkynyl, cycloalkyl, aryl, or heteroaryl is optionally substituted with one or more —$OR^{14}$, —$NR^{14}R^{15}$, —$SR^{14}$, or halogen; or
$R^3$ and $R^4$ can combine with the carbon atoms to which they are attached to form a $C_3$-$C_6$ cycloalkyl, a $C_4$-$C_6$cycloalkenyl, or 3- to 6-membered ring heterocycle; and/or
$R^7$ and $R^8$ can combine with the carbon atoms to which they are attached to form a $C_3$-$C_6$ cycloalkyl, a $C_4$-$C_6$cycloalkenyl, or 3- to 6-membered ring heterocycle;
$R^{14}$ and $R^{15}$ are each independently, at each occurrence, —H, —$C_1$-$C_6$alkyl, —$C_2$-$C_6$alkenyl, or —$C_2$-$C_6$alkynyl;
the symbol ⁼⁼⁼⁼⁼⁼ represents a single bond or a cis or trans double bond;
n is 0, 1, 2, 3, 4, 5, 6, 7 or 8;
m is 0, 1, 2 or 3;
q is 0, 1, 2, 3, 4 or 5; and
r is 0, 1, 2, 3, 4, 5, 6, 7 or 8; and
at least two additives;
wherein a molar ratio of the additives to the compound of Formula I is about 1 or higher.

In still another aspect of the present disclosure, a composition includes a compound of Formula II:

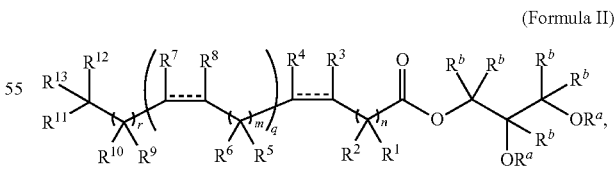

(Formula II)

wherein:
each $R^a$ is independently —H or —$C_1$-$C_6$alkyl;
each $R^b$ is independently selected from —H, —$C_1$-$C_6$alkyl, or —OH;
$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl, wherein each alkyl, alkenyl, alkynyl, cycloalkyl, aryl, or heteroaryl is optionally substituted with one or more —OR$^{14}$, —NR$^{14}$R$^{15}$, —SR$^{14}$, or halogen;

R$^3$, R$^4$, R$^7$, and R$^8$ are each independently, at each occurrence, —H, —OR$^{14}$, —NR$^{14}$R$^{15}$, —SR$^{14}$, halogen, —C$_1$-C$_6$alkyl, —C$_2$-C$_6$alkenyl, —C$_2$-C$_6$alkynyl, —C$_3$-C$_7$cycloalkyl, aryl, or heteroaryl wherein each alkyl, alkenyl, alkynyl, cycloalkyl, aryl, or heteroaryl is optionally substituted with one or more —OR$^{14}$, —NR$^{14}$R$^{15}$, —SR$^{14}$, or halogen; or R$^3$ and R$^4$ can combine with the carbon atoms to which they are attached to form a C$_3$-C$_6$ cycloalkyl, a C$_4$-C$_6$cycloalkenyl, or 3- to 6-membered ring heterocycle; and/or R$^7$ and R$^8$ can combine with the carbon atoms to which they are attached to form a C$_3$-C$_6$ cycloalkyl, a C$_4$-C$_6$cycloalkenyl, or 3- to 6-membered ring heterocycle;

R$^{14}$ and R$^{15}$ are each independently, at each occurrence, —H, —C$_1$-C$_6$alkyl, —C$_2$-C$_6$alkenyl, or —C$_2$-C$_6$alkynyl;

the symbol ══════ represents a single bond or a cis or trans double bond;

n is 0, 1, 2, 3, 4, 5, 6, 7 or 8;

m is 0, 1, 2 or 3;

q is 0, 1, 2, 3, 4 or 5; and r is 0, 1, 2, 3, 4, 5, 6, 7 or 8; and a first additive and a second additive; wherein the compound of Formula II, the first additive, and the second additive are each different from one another; and the first and second additives are each independently selected from the group of compounds consisting of 1-monoacylglycerides, fatty acids, esters, amides, amines, thiols, carboxylic acids, ethers, aliphatic waxes, alcohols, organic salts, and inorganic salts.

Compositions and solutions described herein can each include one or more of the following features, either alone or in combination with one another. The symbol ══════ can represent a single bond, a double bond, or a double bond between R$^3$ and R$^4$. R$^{11}$ can be —OH. n can be 7, and R$^3$ and/or R$^4$ can be —OH. R$^3$ and R$^4$ can combine with the carbon atoms to which they are attached to form an epoxide. R$^1$, R$^2$, R$^3$, R$^4$, R$^5$, R$^6$, R$^7$, R$^8$, R$^9$, R$^{10}$, R$^{11}$, R$^{12}$, and R$^{13}$ can each be —H. The mass ratio of the additive to the compound of Formula I can be in a range of about 0.1 to about 1, about 0.1 to about 0.5, about 0.2 to about 0.4, about 0.25 to about 0.35, about 0.3 to about 0.7, about 0.4 to about 0.6, about 0.45 to about 0.55, about 0.1 to about 1, about 0.1 to about 0.5, about 0.2 to about 0.4, about 0.25 to about 0.35, about 0.3 to about 0.7, about 0.4 to about 0.6, or about 0.45 to about 0.55.

The composition or solution can include an additive. The composition or solution can include a first additive and a second additive. The composition or solution can include at least two additives. The first additive can be different from the second additive. The additive, first additive, or second additive can be a compound of Formula II, where Formula II is as previously described. The additive, first additive, or second additive can be a fatty acid. The additive, first additive, or second additive can be an ester. The first additive can be a fatty acid and the second additive can be a compound of Formula II, where Formula II is as previously described. The composition can comprise less than about 10% of proteins, polysaccharides, phenols, lignans, aromatic acids, terpenoids, flavonoids, carotenoids, alkaloids, alcohols, alkanes, and aldehydes. The additive can be a fatty acid having a carbon chain length that is the same as a carbon chain length of the compound of Formula I. The additive can be a fatty acid having a carbon chain length that is different from a carbon chain length of the compound of Formula I. The additive can be a fatty acid having a carbon chain length that is the same as a carbon chain length of the compound of Formula II. The additive can be a fatty acid having a carbon chain length that is different from a carbon chain length of the compound of Formula II. The at least two additives can each be independently selected from the group of compounds consisting of 1-monoacylglycerides, fatty acids, esters, amides, amines, thiols, carboxylic acids, ethers, aliphatic waxes, alcohols, organic salts, and inorganic salts. The first and second additives can each be independently selected from the group of compounds consisting of 1-monoacylglycerides, fatty acids, esters, amides, amines, thiols, carboxylic acids, ethers, aliphatic waxes, alcohols, organic salts, and inorganic salts. The first and second additives can each be fatty acids. The first additive can be palmitic acid and the second additive can be oleic acid. A carbon chain length of the compound of Formula I can be the same as a carbon chain length of the compound of Formula II. A carbon chain length of the compound of Formula I can be different from a carbon chain length of the compound of Formula II. As used herein, the term "carbon chain length" is understood as the portion of a compound of Formula I, Formula II, Formula III or a fatty acid additive that is bound to the carbonyl carbon. That is, the carbon chain length can be defined by the variables m, n, q and r.

The composition can be soluble in ethanol at a range of at least 20 mg/mL, at least 50 mg/mL, at least 100 mg/mL, at least about 20 mg/mL, at least about 50 mg/mL, or at least about 100 mg/mL. The composition can be soluble in water at a range of at least 20 mg/mL, at least 50 mg/mL, at least 100 mg/mL, at least about 20 mg/mL, at least about 50 mg/mL, or at least about 100 mg/mL. The composition can be soluble in a solvent including ethanol and water at a range of at least 20 mg/mL, at least 50 mg/mL, at least 100 mg/mL, at least about 20 mg/mL, at least about 50 mg/mL, or at least about 100 mg/mL. The solvent can be at least 25% water by volume, at least 50% water by volume, at least 75% water by volume, at least 90% water by volume, less than 35% water by volume, at least about 25% water by volume, at least about 50% water by volume, at least about 75% water by volume, at least about 90% water by volume, or less than about 35% water by volume. The composition can be a solid at about 25° C. and about 1 atmosphere of pressure, and optionally the solid can include crystals having an average diameter less than about 2 millimeters.

The concentration of the solute in the solution can be at least 0.5 mg/mL, at least 1 mg/mL, at least 5 mg/mL, at least 10 mg/mL, at least 20 mg/mL, at least about 0.5 mg/mL, at least about 1 mg/mL, at least about 5 mg/mL, at least about 10 mg/mL, or at least about 20 mg/mL. The concentration of the solute in the solution can be below the saturation limit. The solvent can comprise, water and/or ethanol. The composition or solution can further comprise an additional agent selected from a pigment or an odorant.

In another aspect of the present disclosure, a method of forming a coating on a substrate comprises: (i) providing a composition comprising a compound Formula I, the composition being dissolved in a solvent to form a solution; (ii) applying the solution to a surface of the substrate; and (iii) causing the composition to re-solidify on the surface to form the coating. In some embodiments, the composition further comprises an additive (e.g., a compound of Formula II). A mass ratio of the additive to the compound of Formula I can be in a range of 0.1 to 1.

In another aspect of the disclosure, a method of forming a coating on a substrate comprises: (i) providing a composition comprising a compound Formula I, the composition being dissolved in a solvent to form a solution; (ii) applying the solution to a surface of the substrate; and (iii) causing the composition to re-solidify on the surface to form the coating. The coating can be optically transparent throughout, or can have an average transmittance of at least 60% for light in the visible range. In some embodiments, an entirety of the coating has a transmittance of at least 60% for light in the visible range. Accordingly, the coating can be free of visible residues larger than 0.25 µm² in area.

In another aspect of the present disclosure, a method of forming a coating on a substrate comprises: (i) providing a composition comprising a compound of Formula II, the composition being dissolved in a solvent to form a solution; (ii) applying the solution to a surface of the substrate; and (iii) causing the composition to re-solidify on the surface to form the coating. The coating can be optically transparent throughout, or can have an average transmittance of at least 60% for light in the visible range. In some embodiments, an entirety of the protective layer has a transmittance of at least 60% for light in the visible range. Accordingly, the protective layer can be free of visible residues larger than 0.25 µm² in area.

In another aspect of the present disclosure, a method for producing a composition comprising a compound of Formula I and an additive includes:

(i) providing a compound of Formula III:

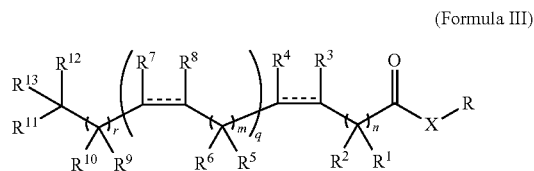

(Formula III)

wherein:

X is O or $NR^1$;

$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen;

$R^3$, $R^4$, $R^7$, and $R^8$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkenyl, —$C_2$-$C_6$alkynyl, —$C_3$-$C_7$cycloalkyl, aryl, or heteroaryl wherein each alkyl, alkynyl, cycloalkyl, aryl, or heteroaryl is optionally substituted with one or more —$OR^{14}$, —$NR^{14}R^{15}$, —$SR^{14}$, or halogen; or $R^3$ and $R^4$ can combine with the carbon atoms to which they are attached to form a $C_3$-$C_6$ cycloalkyl, a $C_4$-$C_6$cycloalkenyl, or 3- to 6-membered ring heterocycle; and/or $R^7$ and $R^8$ can combine with the carbon atoms to which they are attached to form a $C_3$-$C_6$ cycloalkyl, a $C_4$-$C_6$cycloalkenyl, or 3- to 6-membered ring heterocycle;

$R^{14}$ and $R^{15}$ are each independently, at each occurrence, —H, —$C_1$-$C_6$alkyl, —$C_2$-$C_6$alkenyl, or —$C_2$-$C_6$alkynyl;

the symbol ====== represents a single bond or a cis or trans double bond;

n is 0, 1, 2, 3, 4, 5, 6, 7 or 8;

m is 0, 1, 2 or 3;

q is 0, 1, 2, 3, 4 or 5; and r is 0, 1, 2, 3, 4, 5, 6, 7 or 8; and

R is selected from —H, —$C_1$-$C_6$alkyl, —$C_2$-$C_6$alkenyl, —$C_2$-$C_6$alkynyl, —$C_3$-$C_7$cycloalkyl, aryl, or heteroaryl;

(ii) converting the compound of Formula III to produce a compound of Formula I

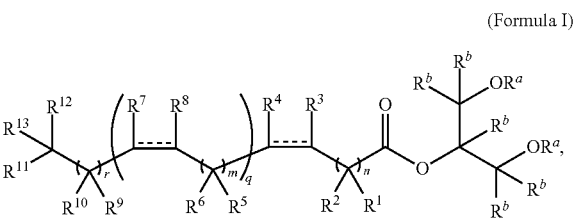

(Formula I)

wherein:

each $R^a$ is independently —H or —$C_1$-$C_6$alkyl;

each $R^b$ is independently selected from —H, —$C_1$-$C_6$alkyl, or —OH;

$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen;

$R^3$, $R^4$, $R^7$, and $R^8$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkenyl, —$C_2$-$C_6$alkynyl, —$C_3$-$C_7$cycloalkyl, aryl, or heteroaryl wherein each alkyl, alkynyl, cycloalkyl, aryl, or heteroaryl is optionally substituted with one or more —$OR^{14}$, —$NR^{14}R^{15}$, —$SR^{14}$, or halogen; or $R^3$ and $R^4$ can combine with the carbon atoms to which they are attached to form a $C_3$-$C_6$ cycloalkyl, a $C_4$-$C_6$cycloalkenyl, or 3- to 6-membered ring heterocycle; and/or $R^7$ and $R^8$ can combine with the carbon atoms to which they are attached to form a $C_3$-$C_6$ cycloalkyl, a $C_4$-$C_6$cycloalkenyl, or 3- to 6-membered ring heterocycle;

$R^{14}$ and $R^{15}$ are each independently, at each occurrence, —H, —$C_1$-$C_6$alkyl, —$C_2$-$C_6$alkenyl, or —$C_2$-$C_6$alkynyl;

the symbol ====== represents a single bond or a cis or trans double bond;

n is 0, 1, 2, 3, 4, 5, 6, 7 or 8;

m is 0, 1, 2 or 3;

q is 0, 1, 2, 3, 4 or 5; and r is 0, 1, 2, 3, 4, 5, 6, 7 or 8;

(iii) combining the compound of Formula I with an additive such that a molar ratio of the additive to the compound of Formula I is in a range of about 0.1 to 1.

In another aspect of the present disclosure, a method of forming a protective coating includes (i) providing a solution comprising a solute dissolved in a solvent, the solute comprising a composition of compounds selected from the group consisting of 1-monoacylglycerides, fatty acids, esters, amides, amines, thiols, carboxylic acids, ethers, aliphatic waxes, alcohols, salts (inorganic and organic), and compounds of Formula I; (ii) applying the solution to a surface of a substrate; and (iii) causing the solute to solidify on the surface and form the protective coating. The protective coating can have a thickness greater than 0.1 microns.

The protective layer can have an average transmittance of at least 60% for light in the visible range.

In another aspect, a method of forming a protective coating includes (i) providing a solution comprising a solute dissolved in a solvent, the solute comprising a compound of Formula I; (ii) applying the solution to a surface of a substrate, and (iii) causing the solute to solidify on the surface and form the protective coating. The protective coating can include the compound of Formula I and can be characterized as being free of free of visible precipitates or other visible residues larger than 0.25 $\mu m^2$ in area.

In another aspect of the present disclosure, a method for reducing food spoilage comprises coating a food substrate with a composition comprising Formula I and an additive in a mass or molar ratio of 0.1 to 1. In some embodiments, the additive is a compound of Formula II as described above.

In another aspect of the present disclosure; a method of protecting harvested produce comprises providing a solution including a solute dissolved in a solvent, and applying the solution to a surface of the harvested produce to form a coating over the produce. The coating can be formed from the solute and can be less than 3 microns thick, and the coating can serve to reduce a rate of mass loss of the harvested produce by at least 10%.

In another aspect of the present disclosure, a solution comprising a compound of Formula I and an additive is disclosed, wherein the molar ratio of the additive to the compound of Formula I is in a range of about 0.1 to 1; and wherein the additive and the compound of Formula I are dissolved in a concentration of at least about 0.5 mg/mL.

In another aspect of the present disclosure, the compounds described herein can be used to form a protective coating on a substrate. The substrate can be an agricultural product, and the coating can help reduce spoilage of the agricultural product.

Methods described herein can each include at least one or more of the following features, either alone or in combination with one another. The composition can be dissolved in the solution at a concentration of at least 0.5 mg/mL or at least 1 mg/mL. The dissolving is performed at a temperature in the range of about 0° C. to about 40° C. The concentration of the solute in the solution can be below the saturation limit. The solvent can comprise water and/or ethanol. The solvent can be at least 25% water by volume, at least 50% water by volume, at least 75% water by volume, at least 90% water by volume, less than 35% water by volume, at least about 25% water by volume, at least about 50% water by volume, at least about 75% water by volume, at least about 90% water by volume, or less than about 35% water by volume.

Causing the composition to re-solidify can include removing (e.g., evaporating) the solvent to precipitate the composition. The compound of Formula III can be an acid, an ester, or an amide. Converting the compound of Formula III to produce a compound of Formula I can include esterifying the acid of Formula III. Converting the compound of Formula III to produce a compound of Formula I can include transesterifying the ester or amide of Formula III. Converting the compound of Formula III to produce a compound of Formula I can include treating the compound of Formula III with an alcohol and a base or acid. The base can be basic resin, sodium hydroxide, lithium hydroxide, potassium hydroxide, sodium carbonate, lithium carbonate, or potassium carbonate. The acid can be methanesulfonic acid, sulfuric acid, toluenesulfonic acid, HCl, or an acidic resin. Converting the compound of Formula III to produce a compound of Formula I can include treating the compound of Formula III with an enzyme.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 14 also shows a plot of the shelf life factor for avocados coated with compositions comprising 1-glycerol esters of stearic acid combined with myristic acid, palmitic acid, and stearic acid.

DETAILED DESCRIPTION

Described herein are compositions and solutions that can be used as coatings for a substrate such as a food product or an agricultural product. The compositions can comprise a compound of Formula I and optionally an additive such as a compound of Formula II, as previously described. Alternatively, the compositions can include a compound of Formula II and optionally an additive. The coatings can be formed, for example, by dissolving the composition in a solvent to form a solution, applying the solution to the surface of the substrate being coated, and then causing the solute to resolidify and form the coating, e.g., by evaporating the solvent and precipitating the solute.

The coatings and methods described herein offer a number of distinct features and advantages over current methods of maintaining freshness of agricultural products and food. For instance, the current disclosure provides coatings that can prevent water loss and shield agricultural products from threats such as bacteria, fungi, viruses and the like. The coatings can also protect, for instance, plants and food products from physical damage (e.g., bruising) and photodamage. Accordingly, the current compositions, solutions, and coatings can be used to help store agricultural products for extended periods of time without spoiling. In some instances, the compositions and coatings allow for food to be kept fresh in the absence of refrigeration. The compositions and coatings provided herein can also be edible (i.e., the coatings can be non-toxic for human consumption). In some embodiments, the coatings are tasteless, colorless, and/or odorless. In some preferred embodiments, the coatings are made from the same chemical feedstocks that are naturally found in the plant cuticle, (e.g., hydroxy and/or dihydroxy palmitic acids, and/or hydroxy or epoxy oleic and stearic acids) and can thus be organic and all-natural.

In addition to protecting substrates such as agricultural products and preventing mass loss and water loss as described above, in many cases it can be desirable for the coatings to be undetectable to the human eye, and/or to not cause any detectable changes in the physical appearance of the coated agricultural product. For example, coatings that precipitate or crystallize upon formation, or otherwise leave a residue upon the surface of the coated product, can cause the coated product to appear soiled or damaged, or to reduce the aesthetic appeal of the product. Consequently, the coated product may appear less desirable to a consumer as compared to a similar uncoated product. As such, in addition to being effective at preventing water/mass loss and/or protecting agricultural products as described above, in many cases it is further desirable that the coating also not leave a visible residue and/or alter the physical appearance of the coated product.

Figure 1:
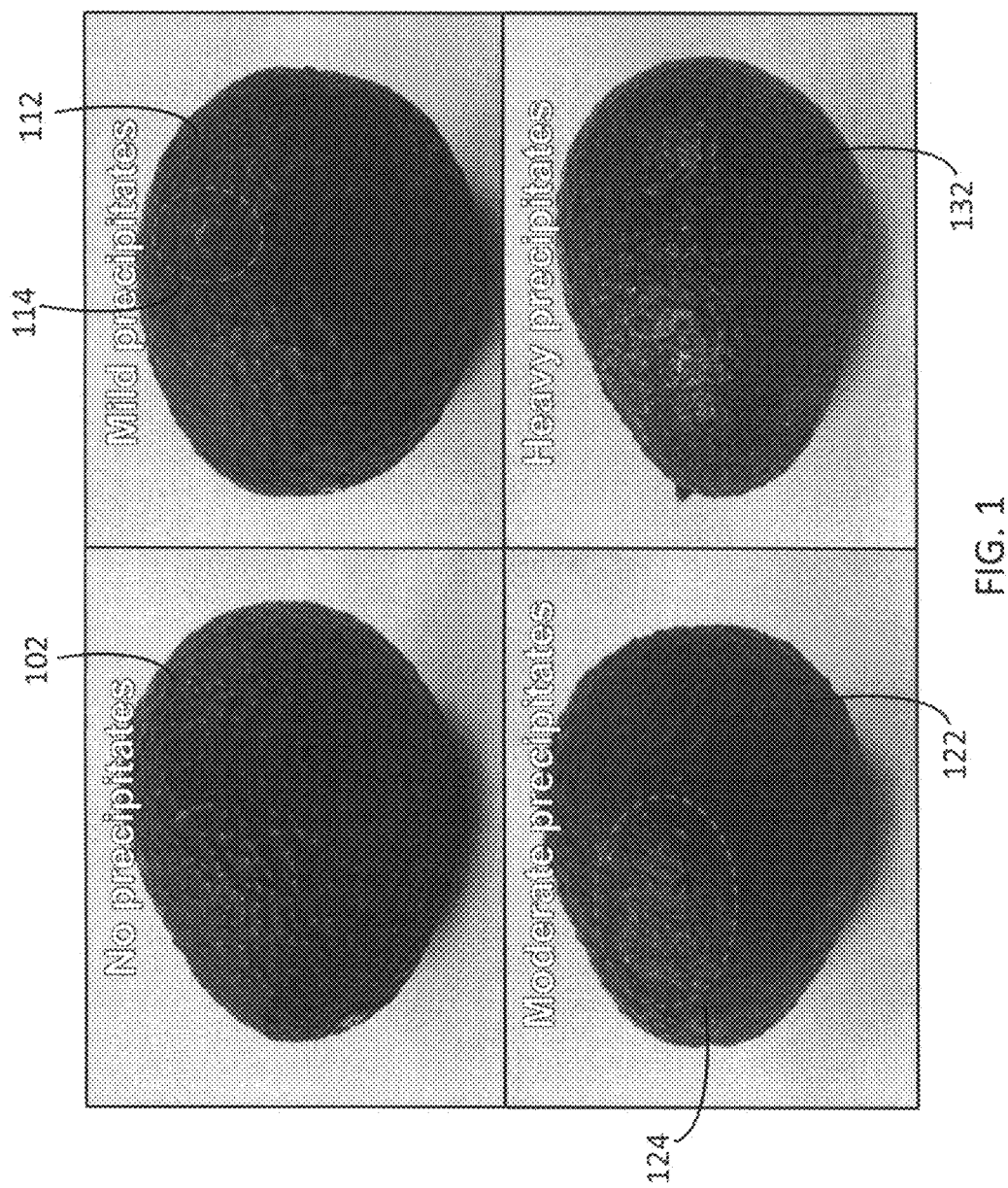
FIG. 1 shows high resolution images of coated avocados having varying levels of visible residues on their surfaces.

FIG. 1 illustrates the appearance and classification of visible residues on the surfaces of avocados after being coated with compositions described herein. Avocado 102 exhibited no visible residues. Avocado 112 had only a small patch 114 (i.e., about 1-2 cm² or smaller, or occupying about 5% or less of the surface area of the avocado) of visible residues. Avocados with one small patch of visible residues were classified as having mild residues. Avocado 122 had a large patch 124 (i.e., about 3-10 cm², or occupying about 5-25% of the surface area of the avocado) of visible residues. Avocados with one large patch of visible residues were classified as having moderate residues. Avocado 132 had wide-spread visible residues covering most or all of the surface. Such avocados were classified as having heavy residues.

As used herein, the term "substrate" refers to any object or material over which a coating is formed or material is deposited. In particular implementations, the substrate is edible to humans, and the coating is an edible coating. Examples of edible substrates include agricultural products and foods such as fruits, vegetables, produce, seeds, nuts, beef, poultry, and seafood. Although in many embodiments the coatings are formed over the entire outer surface of the substrate, in some embodiments the coatings can cover a portion of the outer surface of the substrate. The coatings can include apertures or porous regions which expose a portion of the outer surface of the substrate.

The term "alkyl" refers to a straight or branched chain saturated hydrocarbon. $C_1$-$C_6$ alkyl groups contain 1 to 6 carbon atoms. Examples of a $C_1$-$C_6$ alkyl group include, but are not limited to, methyl, ethyl, propyl, butyl, pentyl, isopropyl, isobutyl, sec-butyl and tert-butyl, isopentyl and neopentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms. As defined herein, the term "alkenyl" can include both "E" and "Z" or both "cis" and "trans" double bonds.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment.

The term "heteroaryl" means a monovalent monocyclic or bicyclic aromatic radical of 5 to 12 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom(s) is selected from N, O, or S. The aromatic radical is optionally substituted independently with one or more substituents described herein.

As used herein, the term "halo" or "halogen" means fluoro, chloro, bromo, or iodo.

The following abbreviations are used throughout. Hexadecanoic acid (i.e., palmitic acid) is abbreviated to PA. Octadecanoic acid (i.e., stearic acid) is abbreviated to SA.

Tetradecanoic acid (i.e., myristic acid) is abbreviated to MA. (9Z)-Octadecenoic acid (i.e., oleic acid) is abbreviated to OA. 1,3-dihydroxypropan-2-yl palmitate (i.e., 2-glycero palmitate) is abbreviated to PA-2G. 1,3-dihydroxypropan-2-yl octadecanoate (i.e., 2-glycero stearate) is abbreviated to SA-2G. 1,3-dihydroxypropan-2-yl tetradecanoic acid (i.e., 2-glycero myristate) is abbreviated to MA-2G. 1,3-dihydroxypropan-2-yl (9Z)-Octadecenoate (i.e., 2-glycero oleate) is abbreviated to OA-2G. 2,3-dihydroxypropan-1-yl palmitate (i.e., 1-glycero palmitate) is abbreviated to PA-1G. 2,3-dihydroxypropan-1-yl octadecanoate (i.e., 1-glycero stearate) is abbreviated to SA-1G. 2,3-dihydroxypropan-1-yl tetradecanoate (i.e., 1-glycero myristate) is abbreviated to MA-1G. 2,3-dihydroxypropan-1-yl (9Z)-Octadecenoate (i.e., 1-glycero oleate) is abbreviated to OA-1G. Ethyl hexadecanoate (i.e., ethyl palmitate) is abbreviated to EtPA.

The compositions described herein can include compounds of the Formula I:

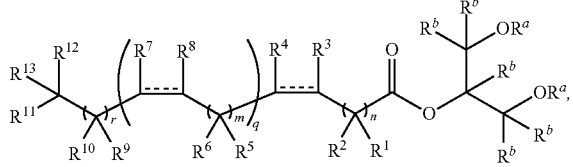

(Formula I)

wherein the definitions of $R^a$, $R^b$, $R^1$, $R^2$, $R^3$, $R^4$, $R^5$, $R^6$, $R^7$, $R^8$, $R^9$, $R^{10}$, $R^{11}$, $R^{12}$, $R^{13}$, m, n, q, and r are as described above, and optionally an additive.

In one or more embodiments, the additive is a compound of Formula II:

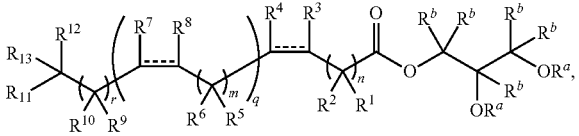

(Formula II)

wherein the definitions of $R^a$, $R^b$, $R^1$, $R^2$, $R^3$, $R^4$, $R^5$, $R^6$, $R^7$, $R^8$, $R^9$, $R^{10}$, $R^{11}$, $R^{12}$, $R^{13}$, m, n, q, and r are as described above.

In one or more embodiments, the symbol ̄ ̄ ̄ ̄ represents a single bond. In one or more embodiments, the symbol ----- represents a double bond. In some embodiments, $R^{11}$ is —OH. In some embodiments, n is 7. In some embodiments, $R^3$ and $R^4$ can be —OH. In some embodiments, n is 7 and $R^3$ is —OH. In one or more embodiments, n is 7 and $R^4$ is —OH. In some embodiments, n is 7 and $R^3$ and $R^4$ are —OH. In some embodiments, n is 7 and $R^3$ and $R^4$ combine with the carbon atoms to which they are attached to form an epoxide. The symbol ----- can represent a double bond between $R^3$ and $R^4$ when n is 7.

The difference between a compound of Formula I and a compound of Formula II is the point of connection of the glycerol ester. In some preferred embodiments, the glycerol ester is unsubstituted. Accordingly, in some preferred embodiments, the present disclosure provides compounds of the Formula I-A:

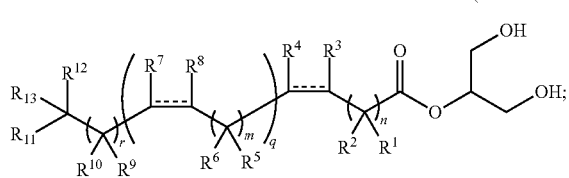

(Formula I-A)

and Formula II-A:

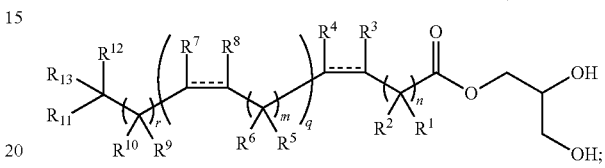

(Formula II-A)

wherein the variables m, n, q, r, $R^1$, $R^2$, $R^3$, $R^4$, $R^5$, $R^6$, $R^7$, $R^8$, $R^9$, $R^{10}$, $R^{11}$, $R^{12}$ and $R^{13}$ are defined as above for Formula I and Formula II.

Studies were carried out in order to identify compounds for coating formulations which reduce the rate of water/mass loss in coated agricultural products and for which the resulting coatings are preferably substantially undetectable to the human eye and/or do not otherwise alter the physical appearance of the coated products. For these studies, mixtures (which were typically solid but in some cases were oils) comprising compounds of Formula I and/or compounds of Formula II and/or other additives (e.g., 1-monoacylglycerides, fatty acids, esters, amides, amines, thiols, carboxylic acids, ethers, aliphatic waxes, alcohols, salts (inorganic and organic), or combinations thereof) were first formed. The mixtures were then dissolved in a solvent (e.g., either ethanol or a water and ethanol mixture, for instance in a 1:2 water:ethanol ratio or lower) to form a solution, from which coatings were formed over a variety of edible substrates (blueberries, bananas, strawberries, lemons, avocados, and limes). Details about the specific formulations used and procedures for the forming of the coatings are described below for illustrative purposes with reference to FIGS. 2-18. The substrates were then examined for the presence of visible residues on the surface and tested for percent mass loss over time, and were compared to control samples without the coatings.

A variety of different compositions of mixtures (e.g., solid mixtures) were used to form coatings on a variety of edible substrates, where the specific compositions and coating procedures are described below with reference to FIGS. 2-18. Some of the compositions were substantially pure (e.g., at least 90% or at least 95% pure) 2-monoacylglyceride compounds (e.g., compounds of Formula I). For example, coatings were formed from compositions that were substantially pure PA-2G, as well as from compositions that were substantially pure SA-2G. Some of the compositions were substantially pure (e.g., at least 90% or at least 95% pure) 1-monoacylglyceride compounds (e.g., compounds of Formula II). For example, coatings were formed from compositions that were substantially pure PA-1G, compositions that were substantially pure OA-1G, and compositions that were substantially pure SA-1G.

Some of the compositions included a compound of Formula I and an additive, where for each of these compositions various ratios of the compound of Formula I to the additive were tested. For example, coatings were formed from compositions which included the combinations of a compound of Formula I and an additive as listed in Table 1 below. Additives included, for example, a saturated or unsaturated compound of Formula II, a saturated or unsaturated fatty acid, an ethyl ester, and/or a second compound of Formula I which is different from the (first) compound of Formula I (e.g., has a different length carbon chain).

TABLE 1

Exemplary Coating Compositions

| Compound of Formula I | Additive | Note |
|---|---|---|
| SA-2G | SA-1G | Additive is a saturated compound of Formula II (1-monoacylglyceride) with the same length carbon chain as the compound of Formula I |
| PA-2G | PA-1G | Additive is a saturated compound of Formula II (1-monoacylglyceride) with the same length carbon chain as the compound of Formula I |
| PA-2G | MA-1G | Additive is a saturated compound of Formula II (1-monoacylglyceride) with a shorter length carbon chain than the compound of Formula I |
| PA-2G | OA-1G | Additive is an unsaturated compound of Formula II (1-monoacylglyceride) with a longer length carbon chain than the compound of Formula I |
| PA-2G | SA-1G | Additive is a saturated compound of Formula II (1-monoacylglyceride) with a longer length carbon chain than the compound of Formula I |
| PA-2G | PA | Additive is a saturated fatty acid with the same length carbon chain as the compound of Formula I |
| PA-2G | OA | Additive is an unsaturated fatty acid with a longer length carbon chain than the compound of Formula I |
| PA-2G | SA | Additive is a saturated fatty acid with a longer length carbon chain than the compound of Formula I |
| PA-2G | MA | Additive is a saturated fatty acid with a shorter length carbon chain than the compound of Formula I |
| PA-2G | OA-2G | Additive is an unsaturated compound of Formula I (2-monoacylglyceride) with a longer carbon chain than PA-2G |
| PA-2G | EtPA | Additive is an ethyl ester. |

In some embodiments, the compound of Formula I is PA-2G. In some embodiments, the compound of Formula I is PA-2G and the additive is PA-1G. In some embodiments, the compound of Formula I is PA-2G and the additive is SA-1G. In some embodiments, the compound of Formula I is PA-2G and the additive is MA-1G. In some embodiments, the compound of Formula I is PA-2G and the additive is OA-1G.

In some embodiments, the compound of Formula I is SA-2G. In some embodiments, the compound of Formula I is SA-2G and the additive is PA-1G. In some embodiments, the compound of Formula I is SA-2G and the additive is SA-1G. In some embodiments, the compound of Formula I is SA-2G and the additive is MA-1G. In some embodiments, the compound of Formula I is SA-2G and the additive is OA-1G.

In some embodiments, the compound of Formula I is MA-2G. In some embodiments, the compound of Formula I is MA-2G and the additive is PA-1G. In some embodiments, the compound of Formula I is MA-2G and the additive is SA-1G. In some embodiments, the compound of Formula I is MA-2G and the additive is MA-1G. In some embodiments, the compound of Formula I is MA-2G and the additive is OA-1G.

In some embodiments, the compound of Formula I is OA-2G. In some embodiments, the compound of Formula I is OA-2G and the additive is PA-1G. In some embodiments, the compound of Formula I is OA-2G and the additive is SA-1G. In some embodiments, the compound of Formula I is OA-2G and the additive is MA-1G. In some embodiments, the compound of Formula I is OA-2G and the additive is OA-1G.

In some embodiments of Formula I or Formula II, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8.

In some embodiments of Formula I or Formula II, m is 0. In some embodiments, m is 1. In some embodiments, m is 2. In some embodiments, m is 3.

In some embodiments of Formula I or Formula II, q is 0. In some embodiments, q is 1. In some embodiments, q is 2. In some embodiments, q is 3. In some embodiments, q is 4. In some embodiments, q is 5.

In some embodiments of Formula I or Formula II, r is 0. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8.

In some embodiments, $R^a$ is hydrogen. In some embodiments, $R^b$ is hydrogen. In some embodiments, $R^a$ and $R^b$ are both hydrogen.

In some embodiments of compounds of Formula I, n is 8. In some embodiments, q is 1. In some embodiments, m is 1. In some embodiments, r is 1.

In some embodiments, compounds of Formula I or Formula II have between 11 and 21 carbon atoms bonded to the carbonyl carbon (i.e., the compounds are $C_{12}$-$C_{22}$ chains). In some embodiments, the compounds of Formula I or Formula II are $C_{12}$, $C_{13}$, $C_{14}$, $C_{15}$, $C_{16}$, $C_{17}$, $C_{18}$, $C_{19}$, $C_{20}$, $C_{21}$, or $C_{22}$ chains.

In some embodiments of compounds of Formula I, n is 8 and q is 1. In some embodiments, n is 8, q is 1 and m is 1. In some embodiments, n is 8, q is 1, m is 1, and r is 1. In some embodiments, n is 8, q is 1, m is 1, r is 1, and ====== represents a single bond.

In some embodiments of compounds of Formula I, m is 3. In some embodiments, n is 8, q is 1 and m is 3. In some embodiments, n is 8, q is 1, m is 3, and r is 1. In some embodiments, n is 8, q is 1, m is 3, r is 1, and ====== represents a single bond.

In some embodiments of compounds of Formula I, n is 6. In some embodiments, n is 6 and q is 1. In some embodiments, n is 6, q is 1 and m is 1. In some embodiments, n is 6, q is 1, m is 1, and r is 1. In some embodiments, n is 6, q is 1, m is 1, r is 1, and ====== represents a single bond.

In some embodiments of compounds of Formula I, n is 7. In some embodiments, n is 7 and q is 1. In some embodiments, n is 7, q is 1 and m is 3. In some embodiments, n is 7, q is 1, m is 3, and r is 1. In some embodiments, n is 7, q is 1, m is 3, r is 1, and ====== represents a cis double bond.

In some embodiments of compounds of Formula II, n is 8. In some embodiments, q is 1. In some embodiments, m is 1. In some embodiments, r is 1.

In some embodiments of compounds of Formula II, n is 8 and q is 1. In some embodiments, n is 8, q is 1 and m is 1. In some embodiments, n is 8, q is 1, m is 1, and r is 1. In some embodiments, n is 8, q is 1, m is 1, r is 1, and ====== represents a single bond.

In some embodiments of compounds of Formula II, m is 3. In some embodiments, n is 8, q is 1 and m is 3. In some embodiments, n is 8, q is 1, m is 3, and r is 1. In some embodiments, n is 8, q is 1, m is 3, r is 1, and ===== represents a single bond.

In some embodiments of compounds of Formula II, n is 6. In some embodiments, n is 6 and q is 1. In some embodiments, n is 6, q is 1 and m is 1. In some embodiments, n is 6, q is 1, m is 1, and r is 1. In some embodiments, n is 6, q is 1, m is 1, r is 1, and ===== represents a single bond.

In some embodiments of compounds of Formula II, n is 7. In some embodiments, n is 7 and q is 1. In some embodiments, n is 7, q is 1 and m is 3. In some embodiments, n is 7, q is 1, m is 3, and r is 1. In some embodiments, n is 7, q is 1, m is 3, r is 1, and ===== represents a cis double bond.

For each of the coatings which were formed from solid mixtures which contained either a single compound of Formula I (i.e., PA-2G or SA-2G) or an additive (i.e., a compound of Formula II, including SA-1 G, PA-1 G, MA-1 G, and OA-1 G) but not a mixture of both, at most a nominal reduction in mass loss was observed for the coated edible substrates as compared to the control samples (i.e., uncoated substrates). Furthermore, all of these coatings resulted in heavy levels of visible precipitates and/or other visible residues or features on the surfaces of the edible substrates.

However, for coatings formed from solid mixtures which contained both a compound of Formula I and an additive, where the mass or molar ratio of the additive to the compound of Formula I was in a range of 0.1 to 1, a substantial reduction in mass loss over time (e.g., as compared to uncoated edible substrates, a reduction in the mass loss rate of at least 20-30% for strawberries, finger limes, and avocados, and at least 10-20% for blueberries) was observed for the coated edible substrates, and visible precipitates and/or other visible residues or features were not observed or were substantially suppressed. This result was observed for a wide variety of additives combined with a compound of Formula I, including all of the combinations listed in Table 1, as well as for a variety of different edible substrates, including blueberries, bananas, strawberries, lemons, avocados, and limes. The reduction in mass loss over time for substrates having coatings with this specific range of mass ratios of the additives to the compounds of Formula I, accompanied by the absence of visible precipitates/residues, was unexpected, in particular since coatings formed from one of the compounds but not the other either did not produce such a large reduction in mass loss in the coated substrates over time or also resulted in heavy visible precipitates and/or other visible residues or features on the surfaces of the substrates. Further details of the compounds, the solutions, the coatings, the procedures for forming the coatings, and the results are presented in the Figures and their associated descriptions below.

As described above, it was observed that for the solid mixtures which were a substantially pure compound of Formula I (e.g., at least 90% pure, at least 95% pure, or at least 99% pure), or contained the compound of Formula I but at most only small amounts of the additive (e.g., the mass or molar ratio of the additive to the compound of Formula I was less than 0.1 or 0.2 or 0.25, or the solid mixture was a substantially pure mixture of the compound of Formula I), the protective coatings that were subsequently formed all tended to at least partially precipitate or leave a visible residue on the surface of the substrate. As seen in FIG. 1, the residues were easily visible to the naked eye, creating the general appearance of a white, film-like substance over portions of the edible substrate, the portions each tending to be at least 0.25 $\mu m^2$ in area, and in some cases at least 1 $\mu m^2$ in area, at least 5 $\mu m^2$ in area, at least 10 $\mu m^2$ in area, at least 100 $\mu m^2$ in area, or at least 1000 $\mu m^2$ in area.

As also described above, similar residues were also observed for coatings formed from solid mixtures which contained a compound of Formula II but at most only small amounts of a compound of Formula I or another additive (e.g., the solid mixture was a substantially pure mixture of compound of Formula II, e.g., at least 90% pure, or only included small amounts of compounds of Formula I or an additive). However, these residues were not present, or were not visible to the naked eye (i.e., if present were smaller than 0.25 $\mu m^2$ in area), in protective coatings formed of compositions which were combinations of Formula I compounds and an additive (e.g., Formula II, fatty acid, and/or ester compounds), where the mass ratio of the additive to the compound of Formula I was greater than about 0.1 (e.g., greater than about 0.2 or between 0.2 and 1). In particular, the residues were not present, or were not visible to the naked eye, in protective coatings formed of compositions including combinations of Formula I and Formula II compounds, where the compositions were at least about 10% Formula I compounds (e.g., at least 20% Formula I compounds) and at least 10% Formula II compounds (e.g., at least 20% Formula II compounds) by mass.

In some embodiments where the coatings are used to protect edible substrates, the presence of the visible residues described above can cause the substrate to appear damaged or to have a less appealing physical appearance to consumers, which may be undesirable. Thus, in many cases, it is desirable for the coatings to be substantially free of visible residues, such that the coating is substantially transparent to light in the visible range and the appearance of the substrate does not appear to be in any way modified from its natural state (e.g., when it is uncoated).

Without wishing to be bound by theory, it is believed that the compounds of Formula I (i.e., the 2-monoacylglyceride compounds) in the solid mixtures, which were subsequently incorporated into the protective coatings, provided for the substantially improved beneficial qualities of the coatings (e.g., reduction in the mass loss rate of at least 20-30% for strawberries, finger limes, and avocados, and at least 10-20% for blueberries) in a variety of edible substrates. However, too high a concentration of compounds of Formula I caused portions of the coatings to precipitate or otherwise leave visible residues. The presence of the residues in the coatings often resulted in porous regions in the coatings, thereby at least partially negating the beneficial properties of the coatings. Combining the compounds of Formula I with a smaller concentration of additives (e.g., 1-monoacylglyceride, fatty acid, and/or ester compounds) in the solid mixtures prevented the visible residues from forming during subsequent formation of the coatings, while at the same time allowing for protective coatings with the beneficial properties described above to be formed. However, if the concentration of compounds of Formula I in the solid mixture was too low (e.g., the mass ratio of the additives to the compounds of Formula I was greater than 1, or the solid mixture was formed of the additive compounds without the compounds of Formula I), even in cases where visible residues were not observed or were less prevalent, the efficacy of the protective coatings was substantially compromised.

As described above, the mass ratio or molar ratio of the additive to the compound of Formula I can be in a range of about 0.1 to about 1. For instance, the range can be from about 0.2 to about 1; about 0.3 to about 1; about 0.1 to about 0.5; from about 0.2 to about 0.4; from about 0.25 to about 0.35; from about 0.3 to about 0.7; from about 0.4 to about 0.6; from about 0.2 to about 0.7; from about 0.5 to about 1; or from about 0.45 to about 0.55. For instance, the molar ratio of the additive (e.g., a compound of Formula II) to the compound of Formula I can be about 0.5, 0.1, 0.15, 0.2, 0.25, 0.3, 0.35, 0.4, 0.45, 0.5, 0.6, 0.65, 0.7, 0.75, 0.8, 0.85, 0.9, 0.95, 1, 1.5, 2, 2.5, 3, or greater. In some embodiments, the molar ratio can be about 0.25, about 0.3, 0.33, or about 0.35.

Additional studies were carried out to examine coatings formed from mixtures that did not contain compounds of Formula I, but included multiple component mixtures of compounds of Formula II, fatty acids, and/or esters. For example, coatings were formed from compositions which included the combinations of compounds of Formula II and one or more additives as listed in Table 2 below. Additives included, for example, a saturated or unsaturated fatty acid, an ethyl ester, and/or one or more additional compounds of Formula II which were different from the (first) compound of Formula II (e.g., have a different length carbon chain).

ans, aromatic acids, terpenoids, flavonoids, carotenoids, alkaloids, alcohols, alkanes, and aldehydes.

In some embodiments, the compositions are substantially pure. For instance, the compound of Formula I and/or Formula II used in the compositions can be greater than 90% pure. It can be, for instance, greater than 91% pure, greater than 92% pure, greater than 93% pure, greater than 94% pure, greater than 95% pure, greater than 96% pure, greater than 97% pure, greater than 98% pure, or greater than 99% pure. In some embodiments, the additive (e.g., Formula II, fatty acid, or ester) can be greater than 90% pure. It can be, for instance, greater than 91% pure, greater than 92% pure, greater than 93% pure, greater than 94% pure, greater than 95% pure, greater than 96% pure, greater than 97% pure, greater than 98% pure, or greater than 99% pure.

While the compositions described herein can be dissolved in a solvent prior to being applied to a substrate, the compositions may be provided without a solvent. In such embodiments, the compositions can be a solid mixture used in the form of a powder, e.g., a dry powder. The solid mixtures can, for example, be provided as a combination of compounds of Formula I and an additive in the ratios previously described. Such solid mixtures (e.g., powders)

TABLE 2

Exemplary Coating Compositions

| Component 1 | Component 2 | (Optional) Component 3 |
|---|---|---|
| SA-1G (Formula II) | MA (Fatty acid, shorter length carbon chain than compound of Formula II) | |
| SA-1G (Formula II) | PA (Fatty acid, shorter length carbon chain than compound of Formula II) | |
| SA-1G (Formula II) | SA (Fatty acid, same length carbon chain as compound of Formula II) | |
| PA-1G (Formula II) | MA (Fatty acid, shorter length carbon chain than compound of Formula II) | |
| PA-1G (Formula II) | PA (Fatty acid, same length carbon chain as compound of Formula II) | |
| PA-1G (Formula II) | SA (Fatty acid, longer length carbon chain than compound of Formula II) | |
| MA-1G (Formula II) | MA (Fatty acid, same length carbon chain as compound of Formula II) | |
| MA-1G (Formula II) | PA (Fatty acid, longer length carbon chain than compound of Formula II) | |
| MA-1G (Formula II) | SA (Fatty acid, longer length carbon chain than compound of Formula II) | |
| SA-1G (First compound of Formula II) | PA-1G (Second compound of Formula II, shorter carbon chain than First compound of Formula II) | |
| SA-1G (First compound of Formula II) | MA-1G (Second compound of Formula II, shorter carbon chain than First compound of Formula II) | |
| MA-1G (First compound of Formula II) | PA-1G (Second compound of Formula II, longer carbon chain than First compound of Formula II) | |
| SA-1G (Formula II) | PA (Fatty acid, shorter length carbon chain than compound of Formula II) | OA (Fatty acid, same length carbon chain as compound of Formula II) |

In one or more embodiments, the compositions described herein are substantially free of impurities such as proteins, polysaccharides, phenols, lignans, aromatic acids, terpenoids, flavonoids, carotenoids, alkaloids, alcohols, alkanes, and aldehydes. In one or more embodiments, compositions described herein contain less than about 10% (e.g., less than about 9%, less than about 8%, less than about 7%, less than about 6%, less than about 5%, less than about 4%, less than about 3%, less than about 2%, or less than about 1%) of impurities such as proteins, polysaccharides, phenols, ligncan be formed having an average grain diameter of less than 2 millimeters. For instance, the solid mixtures can have an average grain diameter of 50 to 1,000 microns (e.g., 100 µm, 200 µm, 300 µm, 400 µm, 500 µm, 600 µm, 700 µm, 800 µm or 900 µm). Solid mixtures with smaller average grain diameter, for instance in the range of 50 nm to 50 µm, can be used as well. In some embodiments, control of the average grain size can provide advantages such as allowing for more efficient dissolution of the mixture in a solvent.

In some embodiments, the composition of the disclosure can be provided in combination with and/or dissolved in a solvent. The composition can be substantially soluble in a solvent, such as water, ethanol, or a combination of both. In some embodiments, a composition comprising Formula I (e.g., a composition comprising a compound of Formula I and Formula II) can be soluble in water at a range of at least about 0.5 mg/mL, at least about 1 mg/mL, at least about 5 mg/mL, at least about 10 mg/mL, at least about 20 mg/mL, at least about 50 mg/mL, or at least about 100 mg/mL. In some embodiments, a composition comprising Formula I (e.g., a composition comprising a compound of Formula I and Formula II) can be soluble in ethanol at a range of at least about 1 mg/mL, at least about 5 mg/mL, at least about 10 mg/mL, at least about 20 mg/mL, at least about 50 mg/mL, or at least about 100 mg/mL. In some embodiments, a composition comprising Formula I (e.g., a composition comprising a compound of Formula I and Formula II) can be soluble in a mixture of water and ethanol at a range of at least about 1 mg/mL, at least about 5 mg/mL, at least about 10 mg/mL, at least about 20 mg/mL, at least about 50 mg/mL, or at least about 100 mg/mL.

If the solvent is a combination of water and ethanol, the solvent can be in any ratio from 1:99 to 99:1. For instance, the solvent can be at least 25% water by volume; at least 50% water by volume; at least 75% water by volume; or at least 90% water by volume. It is understood that the compositions disclosed herein may be substantially soluble (e.g., 100% soluble at a concentration of at least about 0.5 mg/mL, at least about 1 mg/mL, at least about 5 mg/mL, at least about 10 mg/mL, at least about 20 mg/mL, at least about 50 mg/mL, or at least about 100 mg/mL) in any of the solvents described herein. For instance, the compositions can be substantially soluble in water or a combination of water and an alcohol (e.g., ethanol). In addition to ethanol, the solvent can also comprise other organic alcohols such as methanol or isopropanol, or a combination of both. The solvent can also comprise organic solvents such as acetone, ethyl acetate or tetrahydrofuran.

In some embodiments, a composition of the present disclosure (e.g., a composition comprising a compound of Formula I and a compound of Formula II) can be a solid at about 25° C. and about one atmosphere of pressure. In some embodiments, a compound of the present disclosure (e.g., a composition comprising a compound of Formula I and a compound of Formula II) can be a liquid or oil at about 25° C. and about one atmosphere of pressure.

In preferred embodiments, the solvent is non-toxic for human consumption. In some embodiments, the solvent is not appreciably absorbed into the substrate when the substrate is coated with a mixture of solvent and compounds of the disclosure. In some embodiments, the solvent is used to dissolve the compounds and coat the substrate. The solvent can then evaporate, leaving the composition on the surface of the substrate. In some embodiments, the evaporation of solvent takes place before the consumption of the substrate (e.g., food product) by a consumer.

In some embodiments, prior to forming a protective coating over the surface of the substrate, the solid compounds of the present disclosure are dissolved in a solvent (e.g., ethanol or a combination of ethanol and $H_2O$). Without wishing to be bound by theory, while the solid mixtures can be highly soluble (e.g., at least 90% soluble at a concentration of at least about 0.5 mg/mL, at least about 1 mg/mL, at least about 5 mg/mL, at least about 10 mg/mL, at least about 20 mg/mL, at least about 50 mg/mL, or at least about 100 mg/mL) in ethanol, many solid mixtures containing an additive (e.g., 1-monoacylglycerides) and a compound of Formula I (e.g., 2-monoacylglycerides) at a respective mass ratio in the range of 0.1 to 1 were found to be highly soluble in solvents that were at least 25% water by volume, for example combinations of EtOH and $H_2O$ which were as high as 40% $H_2O$ by volume. For example, at or near room temperature (e.g., at a temperature in the range of 0° C. to 40° C., such as in the range of 15° C. to 35° C.), the solubility limit of the solid mixture in a solvent that is at least 25% water by volume can be sufficiently high to allow for a solute (e.g., compounds of Formula I and/or an additive) to solvent ratio of at least 0.5 mg or 1 mg of solid mixture per milliliter of solvent, for example a solute to solvent ratio in the range of 1 to 20 mg or 0.5 to 100 mg of solid mixture per milliliter of solvent.

In some embodiments, a solid mixture that is highly soluble (e.g., at least 90% soluble at a concentration of at least about 0.5 mg/mL, at least about 1 mg/mL, at least about 5 mg/mL, at least about 10 mg/mL, at least about 20 mg/mL, at least about 50 mg/mL, or at least about 100 mg/mL) in a solvent with a high percentage of water can be beneficial by reducing the overall costs associated with forming the protective coatings, and can also allow for the use of a non-toxic solvent which can optionally be recycled.

The composition can be a solid at standard temperature and pressure (i.e., about 25° C. and about 1 atmosphere of pressure). In some embodiments, a composition of the disclosure (e.g., a composition comprising a compound of Formula I and a compound of Formula II) can include solid crystals having an average diameter of less than about 2 millimeters (e.g., less than 1.5 millimeters, or less than 1 millimeter).

In one or more embodiments, the compound of Formula I can be selected from:

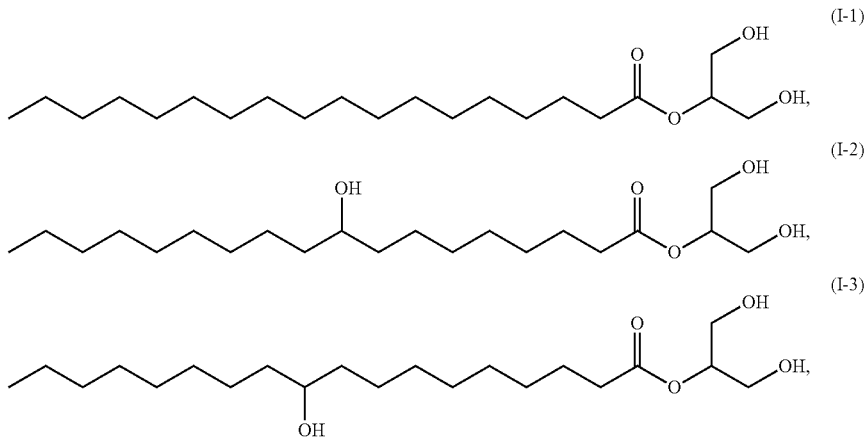

-continued
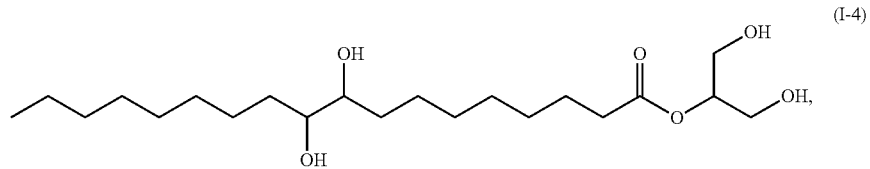
(I-4)
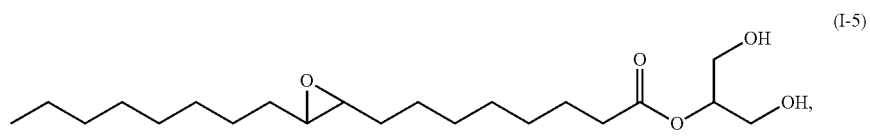
(I-5)
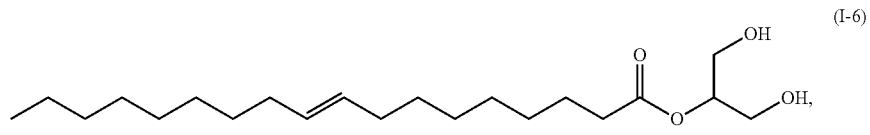
(I-6)
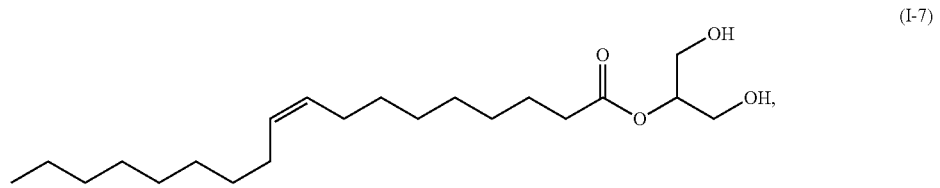
(I-7)
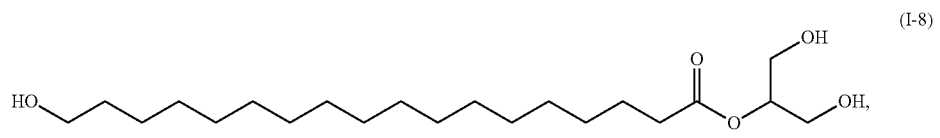
(I-8)
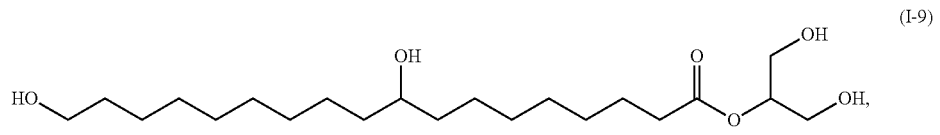
(I-9)
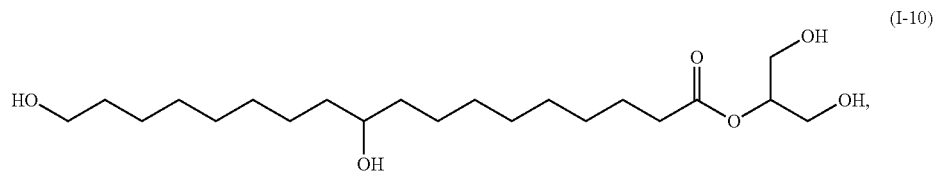
(I-10)
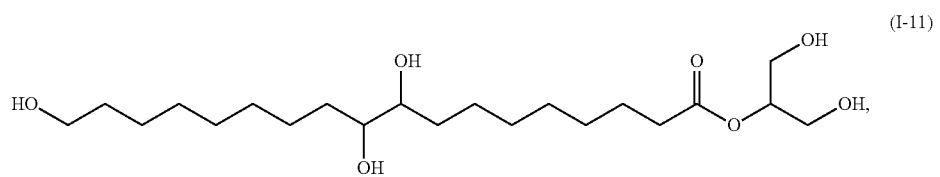
(I-11)
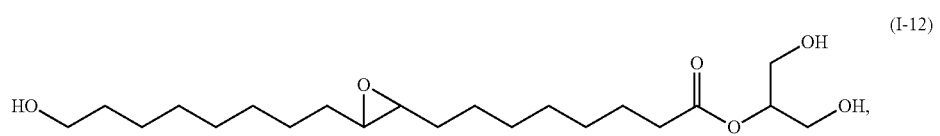
(I-12)
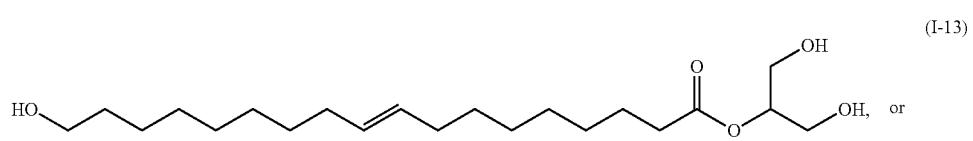
(I-13) or
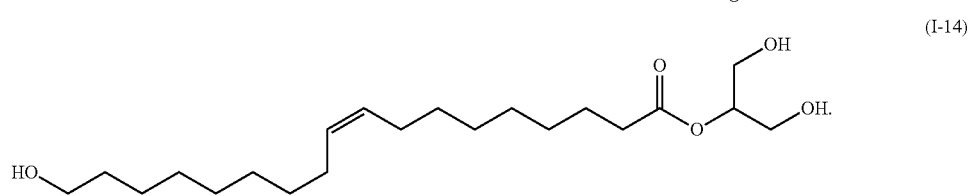
(I-14)

In one or more embodiments, the compound of Formula I can be selected from:
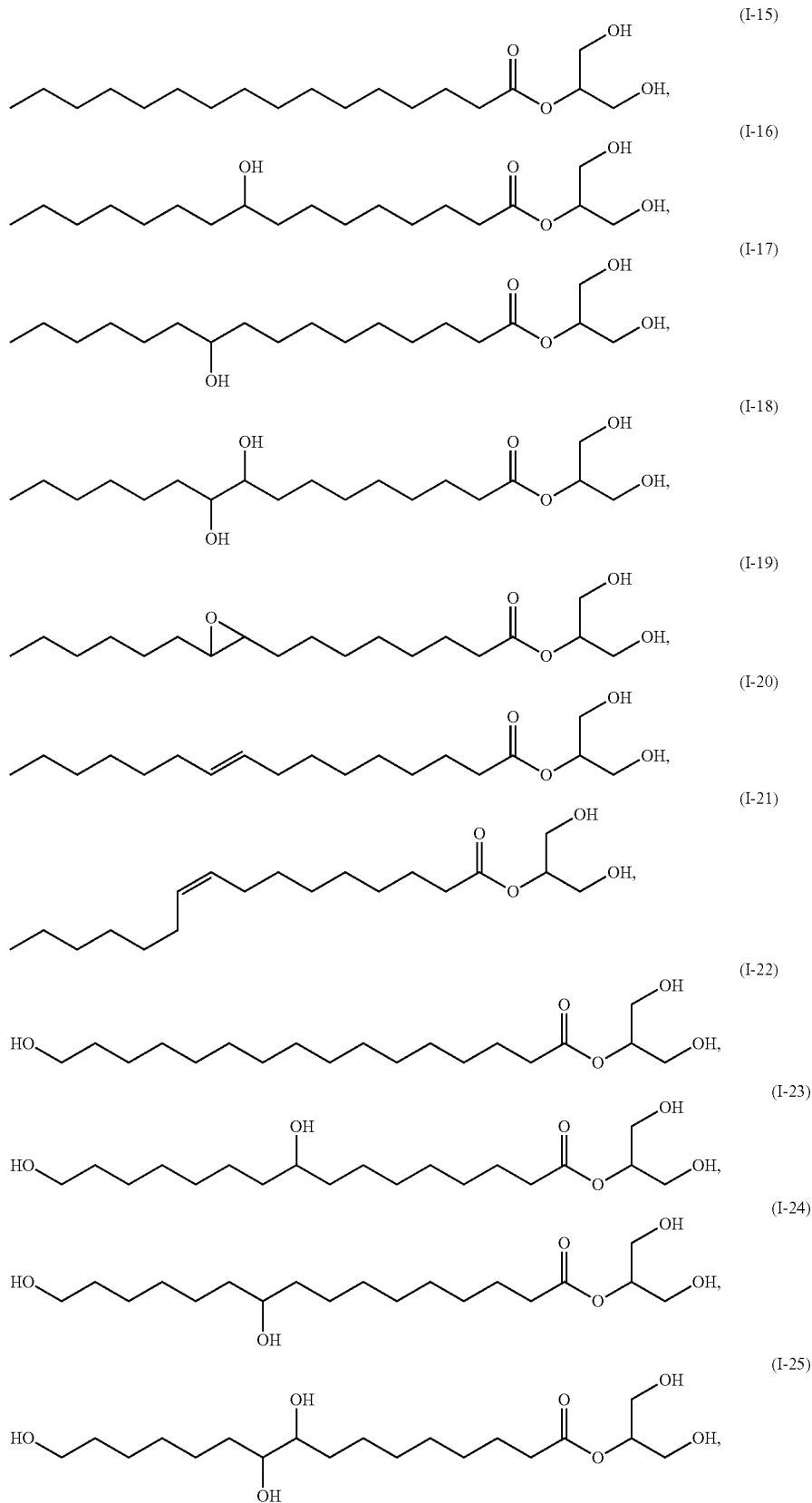

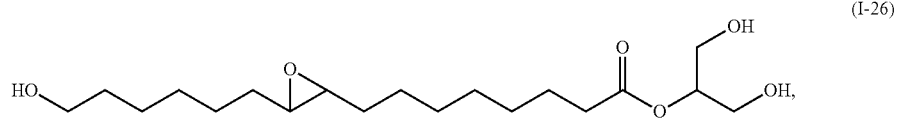
(I-26)
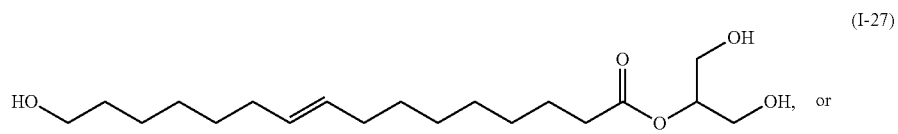
(I-27)
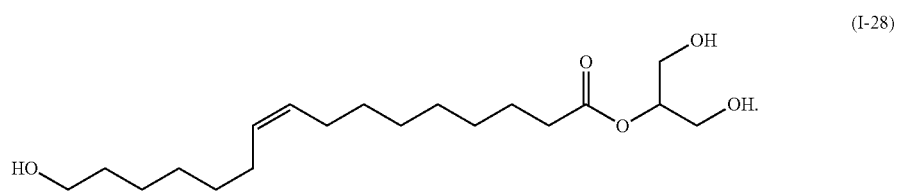
(I-28)
In one or more embodiments, the compound of Formula II can be selected from:
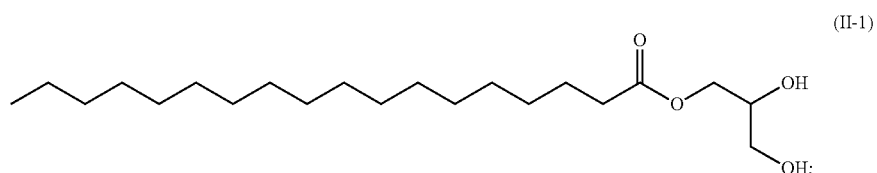
(II-1)
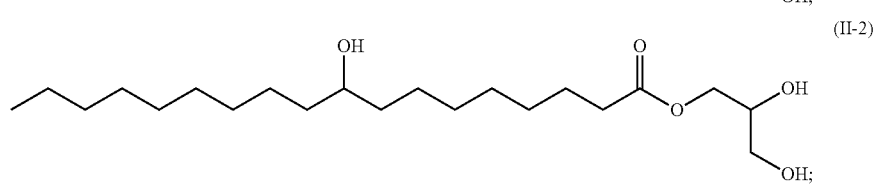
(II-2)
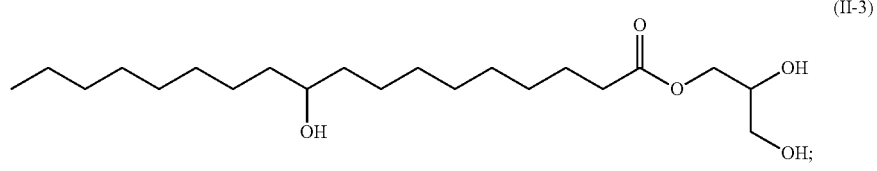
(II-3)
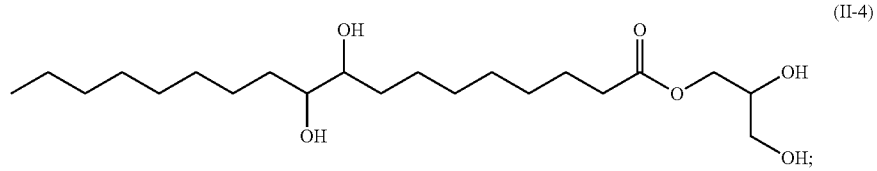
(II-4)
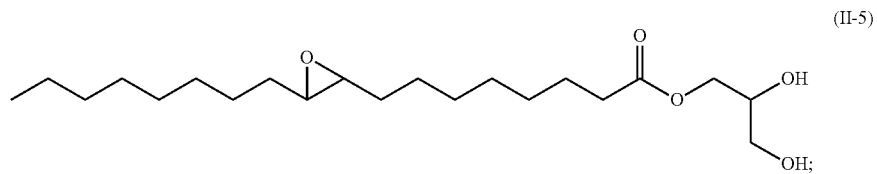
(II-5)
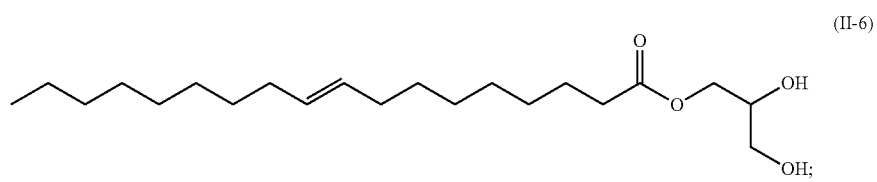
(II-6)

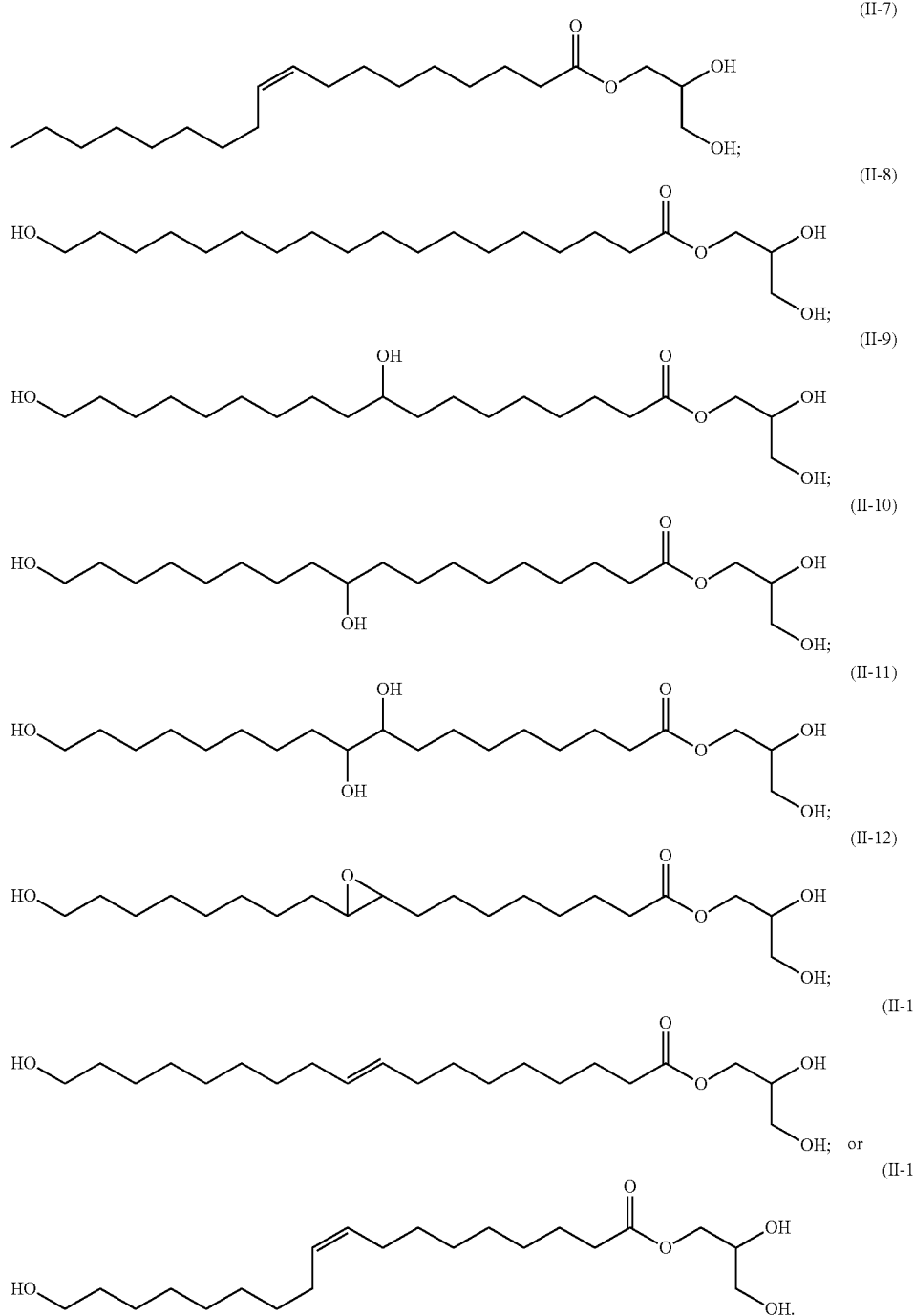
In one or more embodiments, the compound of Formula II can be selected from:
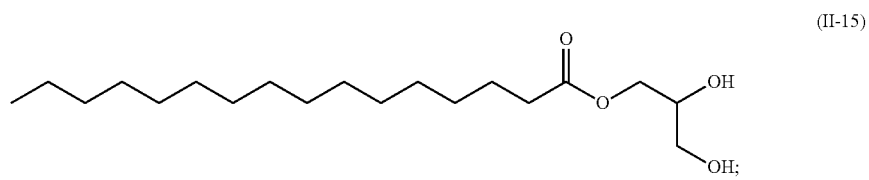

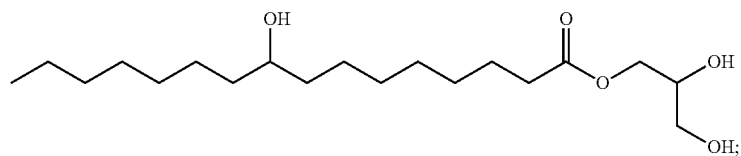
(II-16)
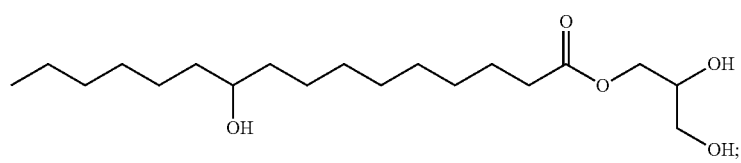
(II-17)
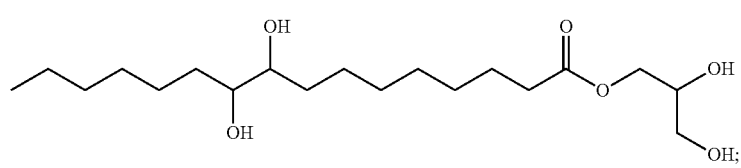
(II-18)
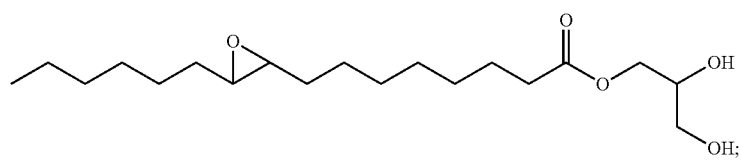
(II-19)
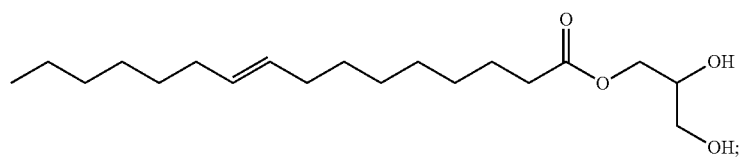
(II-20)
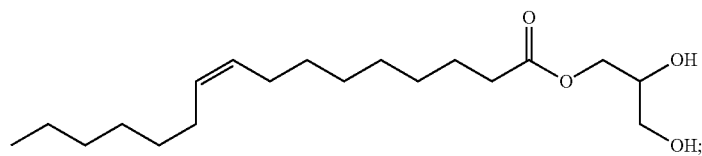
(II-21)
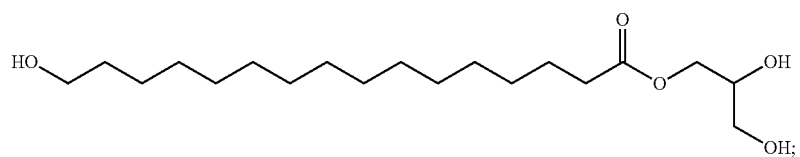
(II-22)
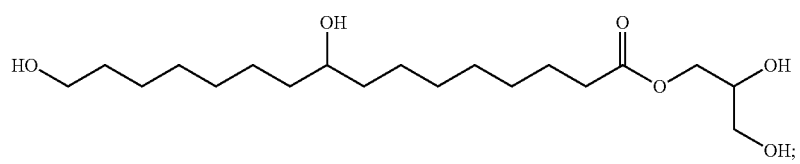
(II-23)
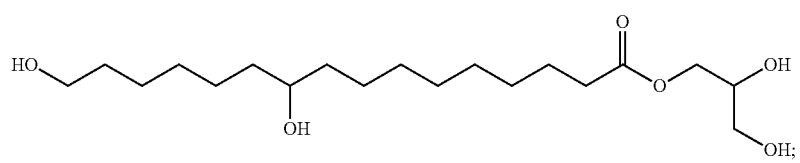
(II-24)

-continued

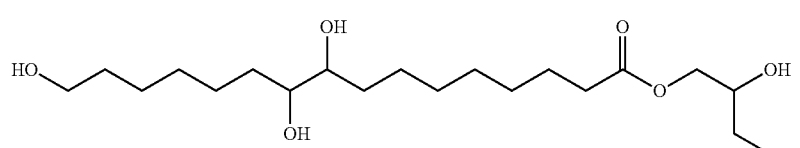

(II-25)

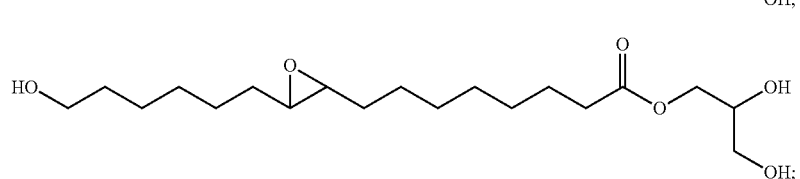

(II-26)

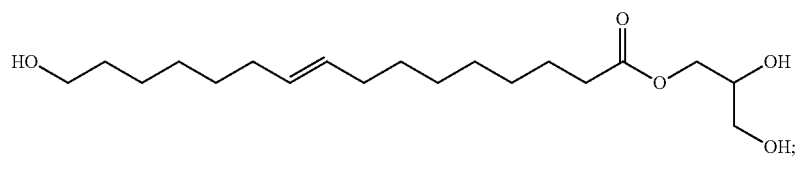

(II-27)

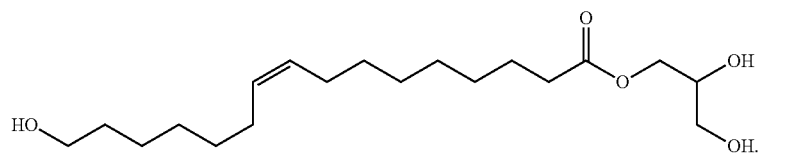

(II-28)

The compounds and compositions of the present disclosure can be dissolved in a solvent before application to a substrate. In some embodiments, the mass ratio or molar ratio of the additive (e.g., a compound of Formula II) to the compound of Formula I is in a range of 0.1 to 1, and wherein the additive and the compound of Formula I are dissolved in a solvent at a concentration of at least about 0.5 mg/mL. In some embodiments, the concentration of the composition in the solvent is at least about 1 mg/mL. In some embodiments, the concentration of the composition in the solvent is at least about 5 mg/mL, at least about 10 mg/mL, at least about 20 mg/mL, at least about 50 mg/mL, or at least about 100 mg/mL. In some embodiments, the solution of the composition in the solvent is saturated or supersaturated. In some embodiments, the concentration of the composition is below the saturation limit in the solution. The dissolution can be performed at a temperature in the range of about 0° C. to about 40° C. (e.g., in the range of about 15° C. to about 30° C.).

The composition can further comprise an additional agent selected from a pigment or an odorant. In some embodiments, the additive is a compound of Formula II.

The compounds and compositions described herein can be used as agents to reduce (e.g., prevent or diminish) food spoilage. For instance, the compounds can be applied to the surface of a food product to supplement the natural cutin barrier found in food products.

Without wishing to be bound by any theory, the coatings formed from compositions of the present disclosure can prevent or suppress water loss (e.g., as compared to uncoated produce, reduce the mass loss rate by at least 20-30% for strawberries, finger limes, and avocados, and at least 10-20% for blueberries) from the substrate via evaporation through the substrate surface, thereby reducing mass loss over time. The coatings formed from the compositions can also prevent oxidation via reaction with oxygen gas that comes into contact with the substrate. The coating can comprise a compound of Formula I along with an additive (e.g. a compound of Formula II). Accordingly, spoilage of, for instance, food or agricultural products is reduced because the chemical balance of the food product does not change significantly from the balance just before harvest (e.g., just before a food product is picked). For example, in some embodiments, coatings of the present disclosure can prevent oxidation (e.g., via ambient oxygen) of compounds that occur naturally in the agricultural products by providing a barrier between atmospheric oxygen and the compounds. For example, in some embodiments the coatings can prevent moisture loss from the agricultural products by providing a barrier between the moisture in the product and the atmosphere. Additionally, the coatings formed from the compounds of the disclosure can protect a substrate such as a food or agricultural product from pathogens such as bacteria, fungi or viruses by presenting a physical barrier between the pathogen and the substrate.

Factors that can affect how well the compositions are able to achieve these functions (e.g., how well the compositions are able to coat and/or protect a substrate) include the specific composition of the precursor compounds used to form the compositions, as well as the thickness, density, and uniformity of the coatings formed from the compositions. In particular, if the coating is non-uniform or includes regions where the composition has locally precipitated, the functionality of the resulting coatings may be compromised.

In some embodiments, the composition (i.e., a mixture of a compound of Formula I and an additive such as a compound of Formula II) is dissolved in a solvent (e.g., water, ethanol, or a combination of both) and applied to the surface of the substrate. The application of the composition can be accomplished by a number of different methods such as spraying, dipping, and the like. For instance, a harvest of fresh food product (e.g., fruit) can be sprayed with a solution comprising a solvent (e.g., water, ethanol or a mixture of the two) and a composition of the disclosure. Alternatively, the harvest can be submerged in a solution comprising a composition of the disclosure and filtered to separate the food products from the solution.

In some embodiments, the coating of a food product is accomplished by contacting the food product with a solution comprising a composition of the present disclosure and allowing the solvent to evaporate. The compositions (e.g., the compound of Formula I and the additive) are left over on the surface of the food product after the solvent dries and thus form the coating.

In some embodiments, the solvent can be removed by mechanical means (e.g., dabbing or swabbing with a towel or other absorbent fabric or surface). In some embodiments, the solvent can be dried by blowing air over the coated food products. In some embodiments, the solvent can be dried by application of a vacuum to the coated food products. In some embodiments, the solvent can be left to evaporate under ambient conditions (i.e., standard temperature and pressure). In the case where the substrate is dipped in a solution of compound and filtered, the residual amounts of the composition of the disclosure that are left after filtration can be sufficient to coat the food product.

One of skill in the art will readily recognize that it can be possible to use, for instance, desiccants and other tools known in the art to effectively remove the solvent from freshly contacted (e.g., sprayed or dipped) substrate without disturbing the coating.

The compounds and solutions of the present disclosure can be applied to a substrate (e.g., a food product) before or after harvest of the food product. For instance, solutions of the present disclosure can be applied to a food product while the food product is still growing, or has not yet been harvested (e.g., before the food product has been picked). Alternatively, the compounds of the present disclosure can be applied after harvest. For instance, freshly picked fruit can be consolidated in containers such as baskets and the solutions of the disclosure can be applied to the fruit shortly after picking.

In some embodiments, the coatings can be undetectable to the human eye. Alternatively, the coating can be formed so as to have a visual quality that is aesthetically pleasing (e.g., to a consumer). For example, when the substrate is an edible substrate such as a fruit or a vegetable, it can be preferable that the coating not modify the general appearance of the substrate surface to make the substrate more appealing. Alternatively, the coating can make the substrate appear shinier or brighter and thus more aesthetically pleasing to the eye (e.g., to a consumer).

As previously described, the coatings can form visible precipitates or other visible residues on the surface of a substrate upon application to the substrate. Without wishing to be bound by any theory, visible precipitates or other visible residues larger than 0.25 square microns (0.25 $\mu m^2$) in area can cause light in the visible spectrum to disperse, creating the appearance of a defect in the underlying substrate. Accordingly, for a given desired thickness of the coating, the specific composition as well as the method of application of the coating can be selected such that the resulting coating is substantially transparent and is substantially free of visible residues larger than 0.25 $\mu m^2$ in area. In some embodiments, the coatings are substantially free of any visible residues formed from the compounds of Formula I and/or additive. In some embodiments, the visible residues are less than 0.25 $\mu m^2$ in area (e.g., less than 0.2 $\mu m^2$, less than 0.15 $\mu m^2$, or less than 0.1 $\mu m^2$). Additionally, visible residues larger than 0.25 $\mu m^2$ in area can disturb the coating such that portions of the substrate in some embodiments are not fully covered and thus not fully protected. This can lead to moisture loss, for instance, and accelerate spoilage.

In some embodiments, the coating can be formed so as to intentionally alter the physical appearance of the substrate, for example to make the substrate appear shinier or brighter and thus more aesthetically pleasing to the eye (e.g., to a consumer), or to have the appearance of a natural wax such as bloom on freshly picked blueberries. In these cases, it may be preferable that the coatings include visible residues larger than 0.25 $\mu m^2$ in area. In such embodiments, it may be preferable that the areal density of visible residues larger than 0.25 $\mu m^2$ in area over the surface be relatively small, so as to improve the physical appearance of the substrate without substantially degrading the quality of the coating. For example, the coating can include at least 10 separate visible residues larger 0.25 $\mu m^2$ in area per square centimeter of the surface of the substrate.

The protective coatings can be applied at a thickness which causes them to decrease the percent mass loss of the substrates over time, as compared to control samples without the coatings. In some implementations, the protective coatings have an average thickness of about 0.1 microns. In some embodiments, the average thickness of the coating can be at least 0.15 microns, at least 0.2 microns, or at least 0.25 microns. In some embodiments, the coatings have a minimum thickness of at least about 0.1 microns. In some embodiments, the coatings can be substantially free of defects while also having an average thickness of about 0.4 microns or greater.

The protective coatings described herein can also be formed substantially thinner than other conventional edible coatings (e.g., wax coatings) while still causing a substantial decrease in the rate of mass loss of the coated produce (or other perishable substrate). For example, in some embodiments, coatings formed over produce by methods described herein can be less than 3 microns thick, less than 2 microns thick, less than 1.5 microns thick, between 0.1 and 3 microns thick, or between 0.05 and 2 microns thick, and can simultaneously reduce the rate of mass loss of the produce (as compared to similar uncoated produce at the same state of ripening) by at least 5%, at least 10%, at least 15%, at least 20%, at least 25%, at least 30%, at least 35%, or at least 40%.

The protective coatings may also be sufficiently optically transparent so as to prevent the coatings from being detectable by the human eye. For example, the coatings can have an average transmittance of at least 60% (e.g., about 60%, at least 65%, at least 70%, at least 80%, at least 85%, at least 90%, at least 95%, about 99% or about 100%) for light in the visible range such as sunlight (i.e., the portion of the solar spectrum having a wavelength between 400 nanometers and 700 nanometers). As used herein, "transmittance" is defined as the ratio of transmitted light power to incident light power. As used herein, "average transmittance" refers to the average value of the transmittance over the entire area of the coating. In some embodiments, the entire coating can in all regions have a transmittance of at least 60% (e.g., about 60%, at least 65%, at least 70%, at least 80%, at least 85%, at least 90%, at least 95%, about 99% or about 100%) for light in the visible range. Because transmittance typically decreases with coating thickness, the coatings can be made thin enough to allow for sufficient transmittance of visible light while still being thick enough to serve as a barrier to mass/moisture loss, as previously described. For example, the protective coatings have an average thickness of less than 2 microns, less than 1.5 microns, less than 1 micron, or less than 0.5 microns.

The compounds of Formula I and/or Formula II may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I.

Those skilled in the art will recognize if a stereocenter exists in the compounds of Formula I and/or Formula II. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

In some embodiments, a compound of Formula I can be prepared from a compound of Formula III (where Formula III is a compound as previously defined) according to Scheme 1.

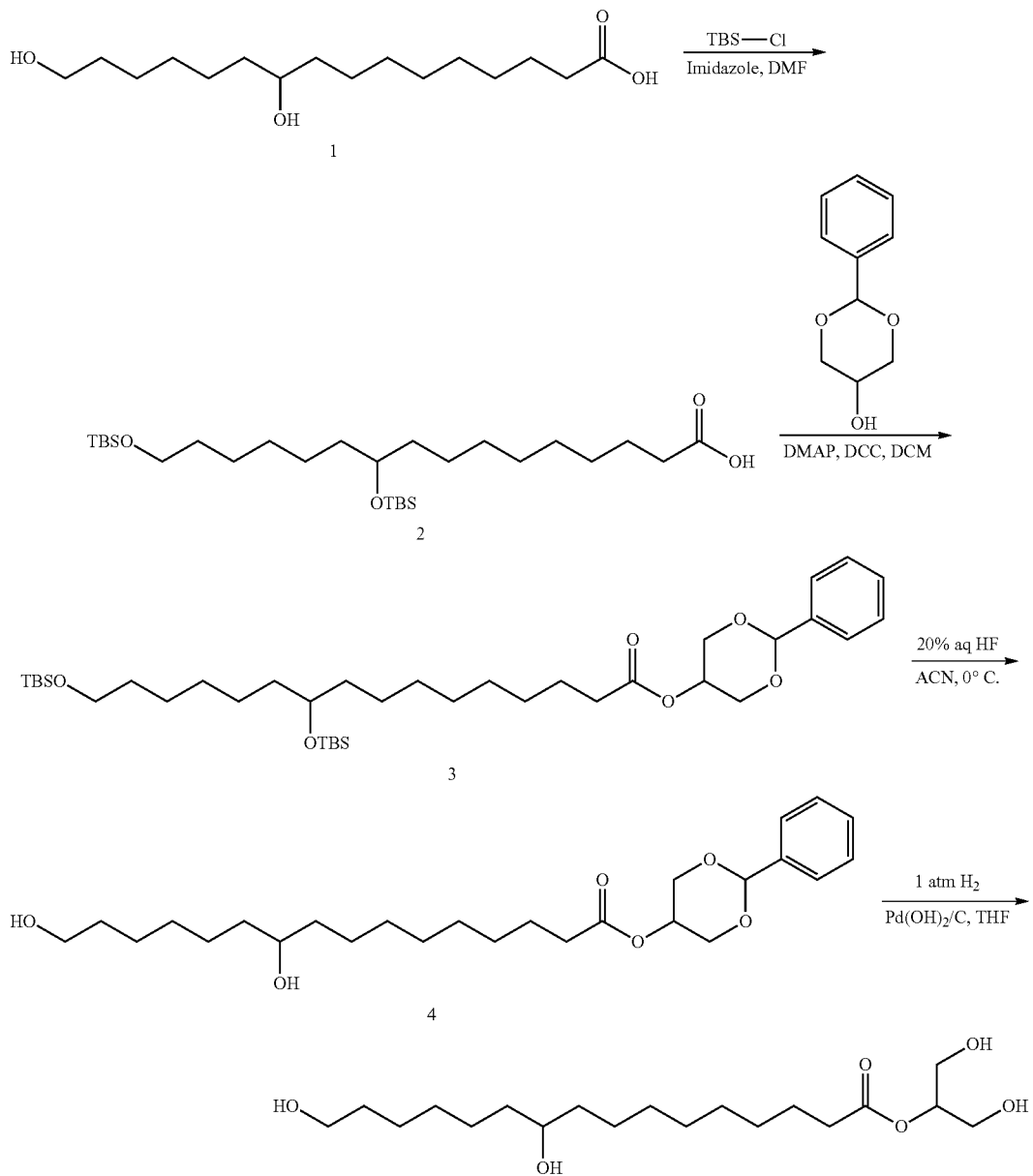

As shown in Scheme 1, glycerol ester compounds of Formula I (e.g., 1-24) can be prepared from the corresponding acid by protecting any hydroxy groups that may be present in the acid (e.g., Formula III). As shown above in Scheme 1, hydroxy groups can be protected with any suitable hydroxy protecting group known in the art, for example a -TBS (tert-butyldimethylsilyl) protecting group. Esterification of the protected acid with an appropriately protected glycerol derivative (e.g., 2-phenyl-1, 3-dioxan-5-ol) can be accomplished by stirring in the presence of DMAP and DCC. Deprotection of the silyl protecting groups can be accomplished with an appropriate agent such as hydrofluoric acid or tetrabutylammonium fluoride (TBAF). Finally, the glycerol group can be deprotected using standard conditions, for instance, hydrogenation or treatment with an acid.

A skilled artisan will understand the chemical synthesis procedures set forth herein can be adjusted as necessary. For instance, other protecting groups can be used to protect, e.g., the alcohol groups as will be understood by one of skill in the art.

In some embodiments, the compound of Formula III is an acid and the converting step comprises esterifying the acid of Formula III. In some embodiments, the compound of Formula III is an ester and the converting step comprises transesterifying the ester of Formula III. In some embodiments, the compound of Formula III is an amide and the converting step comprises transesterifying the amide of Formula III. In some embodiments, the converting step comprises treating the compound of Formula III with an appropriate alcohol and base or acid. In some embodiments, the base is sodium hydroxide, lithium hydroxide, potassium hydroxide, sodium carbonate, lithium carbonate, or potassium carbonate. In some embodiments, the step of converting a compound of Formula III to a compound of Formula II comprises treating the compound of Formula III with an enzyme.

In some embodiments, the forming of the compositions and the subsequent formation of the coatings is carried out by multiple parties. For example, a supplier or manufacturer of compounds suitable for the compositions described herein could form a solution comprising the compounds dissolved in a solvent and provide (e.g., supply or sell) the solution to a grower or distributor of produce. The grower or distributor could then apply the solution to produce, for example by dipping the produce in the solution, spraying the solution onto the produce, or brushing the solution onto the produce. The grower or distributor could then cause the composition to re-solidify on the surface of the produce to form the coating, for example by placing the produce on a drying rack and allowing the solvent to evaporate (or alternatively by blow drying the produce), thereby allowing the composition to solidify and form a coating over the produce. That is, after applying the solution to the produce, the solvent can be removed in order to precipitate the composition over the produce. As another example, a supplier or manufacturer of compounds suitable for the compositions described herein could form a solid mixture (e.g., in powder form) of the compounds and provide (e.g., supply or sell) the solid mixture to a grower or distributor of produce. The grower or distributor could then dissolve the solid mixture in a solvent to form a solution and apply the solution to produce, for example by dipping the produce in the solution, spraying the solution onto the produce, or brushing the solution onto the produce. The grower or distributor could then cause the composition to re-solidify on the surface of the produce to form the coating, for example by placing the produce on a drying rack and allowing the solvent to evaporate (or alternatively by blow drying the produce), thereby allowing the composition to solidify and form a coating over the produce.

In some cases where multiple parties are involved, the first party (e.g., the party that forms the solid compositions and/or solutions) may optionally provide instructions or recommendations about, for example, how to form solutions from the solid compositions, how to treat the produce or other substrates, and/or how to cause the solvent to be removed and the coatings to be formed. The instructions can, for example, be provided in either written or oral form, and may indicate one or more of the following: (i) that solid compositions are to be dissolved in a solvent and then applied to a substrate; (ii) suitable solvents in which to dissolve the solid compositions, as well as suitable concentrations for the solid compositions dissolved in the solvent; (iii) suitable procedures for applying the solutions to the substrates; and/or (iv) suitable procedures for removing (e.g., evaporating) the solvent and/or forming a coating over the surface of the substrate. While the instructions or recommendations can be supplied by the first party directly with the solid compositions and/or solutions (e.g., on packaging in which the solid compositions and/or solutions are stored), the instructions or recommendations may alternatively be supplied separately, for example on a website owned or controlled by the first party, or in advertising or marketing material provided by or on behalf of the first party.

In view of the above, it is recognized that in some cases, a party forms and/or provides solid compositions and/or solutions according to one or more embodiments described herein (i.e., a first party) may not directly apply the compositions/solutions to the substrates to form coatings, but can instead direct (e.g., can instruct or request) a second party (or third party) to apply the compositions/solutions to the substrates and/or to form coatings. That is, even if the first party does not apply the solution to a surface of the substrate, the first party may still cause the solution to be applied to a surface of the substrate, for example by providing instructions or recommendations as described above. Similarly, the first party can also cause the solvent to be removed and/or the composition to re-solidify on the surface to form the coating, for example by providing instructions or recommendations to the second party on procedures for removing (e.g., evaporating) the solvent and/or for allowing the composition to re-solidify on the surface to form the coating. Accordingly, as used herein, the act of applying a composition or solution to a surface of a substrate can also include directing or instructing another party to apply the composition or solution to the surface of the substrate, or causing the composition or solution to be applied to the surface of the substrate. Additionally, as used herein, the act of causing a composition to re-solidify on the surface of a substrate to form the coating can also include directing or instructing another party to on how to cause the composition to re-solidify on the surface of a substrate to form the coating.

EXAMPLES

The disclosure is further illustrated by the following synthesis and use examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

All reagents and solvents were purchased and used without further purification unless specified. Palmitic acid (98%) was purchased from Sigma-Aldrich. p-TsOH and MTBE were purchased from Alfa-Aesar. Toluene, Et$_2$O, and EtOAc were purchased from VDR. Lipozyme® TL IM lipase was purchased from Novozymes. 10 wt % Pd/C was purchased from Strem Chemicals and used as received. All reactions were carried out under an atmosphere of air with non-dried solvents unless otherwise stated. Yields refer to chromatographically and spectroscopically ($^1$H NMR) homogeneous materials, unless otherwise stated. Reactions were monitored by thin layer chromatography (TLC) carried out on 0.25 mm E. Merck silica gel plates (60F-254) using UV light as the visualizing agent and an acidic mixture of anisaldehyde, ceric ammonium molybdate, or basic aqueous potassium permangante (KMnO$_4$), and heat as developing agents. NMR spectra were recorded on a Bruker Avance 500 MHz and/or Varian VNMRs 600 MHz instruments and calibrated using residual un-deuterated solvent as an internal reference (CHCl$_3$ at 7.26 ppm $^1$H NMR, 77.16 ppm $^{13}$C NMR). The following abbreviations (or combinations thereof) were used to explain the multiplicities: s=singlet, d=doublet, t=triplet, q=quartet, m=multiplet, br=broad. Mass spectra (MS) were recorded on a time of-flight mass spectrometer by electrospray ionization (ESI) or field desorption (FD) at the UC Santa Barbara mass spectrometry facility. 1,3-bis(benzyloxy)propan-2-ol was synthesized according to the procedure of Nemoto et al. (*J. Org. Chem.*, 1992, 57, p. 435).

The following abbreviations are used in the following examples and throughout the specification:
DCC=N,N'-Dicyclohexylcarbodiimide
DCM=dichloromethane
DMAP=Dimethylamino pyridine
DMF=N,N-dimethylformamide
MBTE=$^t$BME=tert-butylmethyl ether
p-TsOH=para toluenesulfonic acid
TBS=TBDPS=tert-butyldimethyl silyl Example 1: Synthesis of 1,3-dihydroxypropan-2-yl Palmitate (3)

Step 1. 1,3-bis(benzyloxy)propan-2-yl palmitate (6)

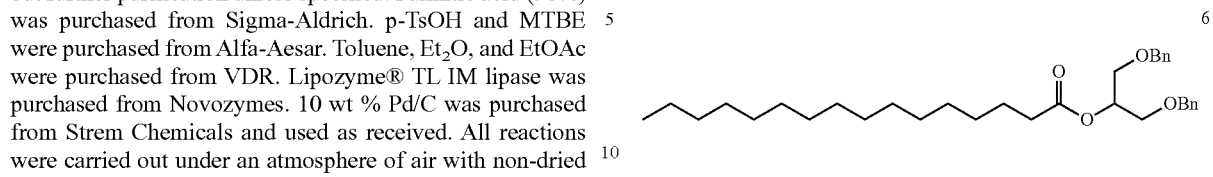

70.62 g (275.34 mmole) of palmitic acid (5), 5.24 g (27.54 mmole) of p-TsOH, 75 g (275.34 mmole) of 1,3-bis(benzyloxy)propan-2-ol, and 622 mL of toluene were charged into a round bottom flask equipped with a Teflon coated magnetic stir bar. A Dean-Stark Head and condenser were attached to the flask and a positive flow of N$_2$ was initiated. The flask was heated to reflux in a heating mantle while the reaction mixture was stirred vigorously until the amount of water collected (~5 mL) in the Dean-Stark Head indicated full ester conversion (~8 hr). The flask was allowed to cool down to room temperature and the reaction mixture was poured into a separatory funnel containing 75 mL of a saturated aqueous solution of Na$_2$CO$_3$ and 75 mL of brine. The toluene fraction was collected and the aqueous layer was extracted with 125 mL of Et$_2$O. The organic layers were combined and washed with 100 mL of brine, dried over MgSO$_4$, filtered and concentrated in vacuo. The crude colorless oil was dried under high vacuum providing (135.6 g, 265.49 mmole, crude yield=96.4%) of 1,3-bis(benzyloxy)propan-2-yl palmitate (6).

HRMS (ESI-TOF) (m/z): calcd. for C$_{33}$H$_{50}$O$_4$Na, [M+Na]$^+$, 533.3607. found, 533.3588.

$^1$H NMR (600 MHz, CDCl$_3$): δ 7.41-7.28 (m, 10H), 5.28 (p, J=5.0 Hz, 1H), 4.59 (d, J=12.1 Hz, 2H), 4.54 (d, J=12.1 Hz, 2H), 3.68 (d, J=5.2 Hz, 4H), 2.37 (t, J=7.5 Hz, 2H), 1.66 (p, J=7.4 Hz, 2H), 1.41-1.15 (m, 24H), 0.92 (t, J=7.0 Hz, 3H) ppm.

$^{13}$C NMR (151 MHz, CDCl$_3$): δ 173.37, 138.09, 128.43, 127.72, 127.66, 73.31, 71.30, 68.81, 34.53, 32.03, 29.80, 29.79, 29.76, 29.72, 29.57, 29.47, 29.40, 29.20, 25.10, 22.79, 14.23 ppm.

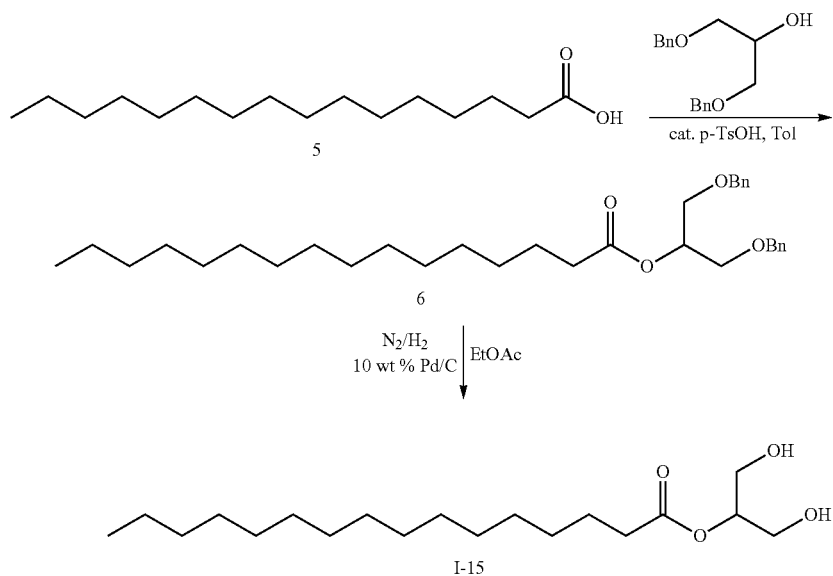

Step 2. 1,3-dihydroxypropan-2-yl palmitate (I-1)

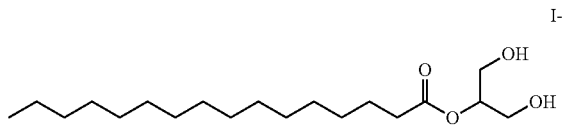
I-1

7.66 g (15.00 mmole) of 1,3-bis(benzyloxy)propan-2-yl palmitate (6), 79.8 mg (0.75 mmole) of 10 wt % Pd/C and 100 mL of EtOAc were charged to a 3 neck round bottom flask equipped with a Teflon coated magnetic stir bar. A cold finger, with a bubbler filled with oil attached to it, and a bubbling stone connected to a 1:4 mixture of $H_2/N_2$ gas tank were affixed to the flask. $H_2/N_2$ was bubbled at 1.2 LPM into the flask until the disappearance of both starting material and mono-deprotected substrate as determined by TLC (~60 min). Once complete, the reaction mixture was filtered through a plug of Celite, which was then washed with 100 mL of EtOAc. The filtrate was placed in a refrigerator at 4° C. for 24 hrs. The precipitate from the filtrate (white and transparent needles) was filtered and dried under high vacuum yielding (2.124 g, 6.427 mmole, yield=42.8%) of 1,3-dihydroxypropan-2-yl palmitate.

HRMS (FD-TOF) (m/z): calcd. for $C_{19}H_{38}O_4$, 330.2770. found, 330.2757.

$^1$H NMR (600 MHz, CDCl$_3$): δ 4.93 (p, J=4.7 Hz, 1H), 3.84 (t, J=5.0 Hz, 4H), 2.37 (t, J=7.6 Hz, 2H), 2.03 (t, J=6.0 Hz, 2H), 1.64 (p, J=7.6 Hz, 2H), 1.38-1.17 (m, 26H), 0.88 (t, J=7.0 Hz, 3H) ppm.

$^{13}$C NMR (151 MHz, CDCl$_3$): δ 174.22, 75.21, 62.73, 34.51, 32.08, 29.84, 29.83, 29.81, 29.80, 29.75, 29.61, 29.51, 29.41, 29.26, 25.13, 22.85, 14.27 ppm.

Example 2—Synthesis of 1,3-dihydroxypropan-2-yl Palmitate by Enzyme Catalysis 3.66 g (4.50 mmole) of tripalmitin (7), 7.26 mg of Lipozyme® TL-IM lipase, 2.65 mL of EtOH, and 363 mL of MTBE were charged to a round bottom flask equipped with a teflon coated magnetic stir bar. The reaction mixture was stirred for 15 min at room temperature, filtered, and concentrated in vacuo. 15 mL of hexanes was added to the crude product and the product/hexanes mixture was stored in a refrigerator at 4° C. for 24 hrs. The crude mixture was filtered, washed with 30 mL of cold hexanes, and dried under high vacuum yielding 1.256 g (3.8 mmole, yield=84.4%) of 1,3-dihydroxypropan-2-yl palmitate (I-1). (Note: yield is based on total mass being from 1,3-dihydroxypropan-2-yl palmitate, however it contains 12.16 mole % (20 wt %) of diacylglycerol palmitate.)

HRMS (FD-TOF) (m/z): calcd. for $C_{19}H_{38}O_4$, 330.2770. found, 330.2757.

$^1$H NMR (600 MHz, CDCl$_3$): δ 4.93 (p, J=4.7 Hz, 1H), 3.84 (t, J=5.0 Hz, 4H), 2.37 (t, J=7.6 Hz, 2H), 2.03 (t, J=6.0 Hz, 2H), 1.64 (p, J=7.6 Hz, 2H), 1.38-1.17 (m, 26H), 0.88 (t, J=7.0 Hz, 3H) ppm.

$^{13}$C NMR (151 MHz, CDCl$_3$): δ 174.22, 75.21, 62.73, 34.51, 32.08, 29.84, 29.83, 29.81, 29.80, 29.75, 29.61, 29.51, 29.41, 29.26, 25.13, 22.85, 14.27 ppm.

Example 3: Synthesis of 1,3-dihydroxypropan-2-yl octadecanoate

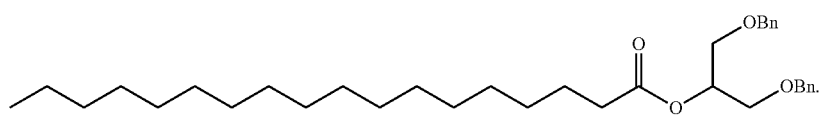

28.45 g (100 mmole) of stearic acid acid, 0.95 g (5 mmole) of p-TsOH, 27.23 g (275.34 mmole) of 1,3-bis(benzyloxy)propan-2-ol, and 200 mL of toluene were charged into a round bottom flask equipped with a Teflon coated magnetic stir bar. A Dean-Stark Head and condenser were attached to the flask and a positive flow of $N_2$ was initiated. The flask was heated to reflux in an oil bath while the reaction mixture was stirred vigorously until the amount of water collected (~1.8 mL) in the Dean-Stark Head indicated full ester conversion (~16 hr). The flask was allowed to cool down to room temperature and the solution was diluted with 100 mL of hexanes. The reaction mixture was

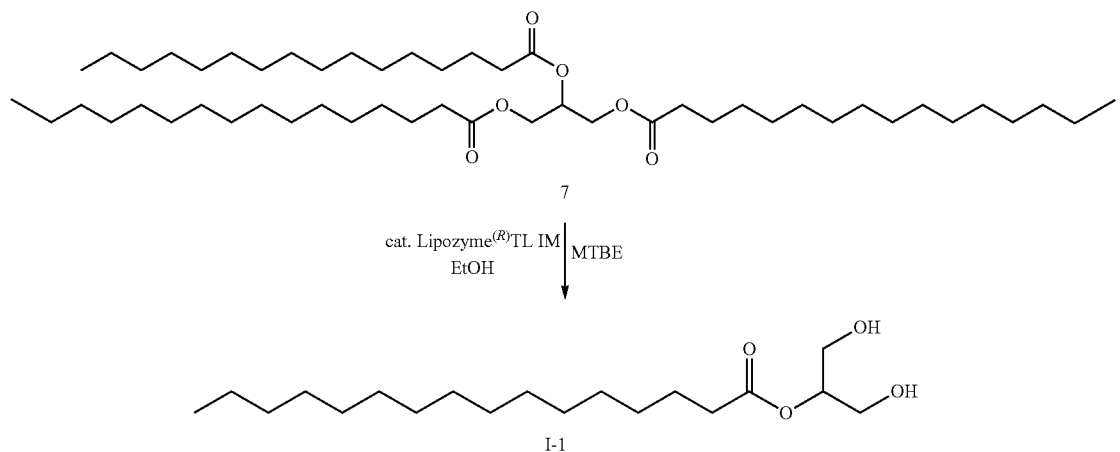

poured into a separatory funnel containing 50 mL of a saturated aqueous solution of Na$_2$CO$_3$. The organic fraction was collected and the aqueous layer was extracted twice more with 50 mL portions of hexanes. The organic layers were combined and washed with 100 mL of brine, dried over MgSO$_4$, filtered and concentrated in vacuo. The crude colorless oil was further purified by selective liquid-liquid extraction using hexanes and acetonitrile and the product was again concentrated in vacuo, yielding (43.96 g, 81.60 mmole, yield=81.6%) of 1,3-bis(benzyloxy)propan-2-yl stearate.

$^1$H NMR (600 MHz, CDCl$_3$): δ 7.36-7.27 (m, 10H), 5.23 (p, J=5.0 Hz, 1H), 4.55 (d, J=12.0 Hz, 2H), 4.51 (d, J=12.1 Hz, 2H), 3.65 (d, J=5.0 Hz, 4H), 2.33 (t, J=7.5 Hz, 2H), 1.62 (p, J=7.4 Hz, 2H), 1.35-1.22 (m, 25H), 0.88 (t, J=6.9 Hz, 3H) ppm.

6.73 g (12.50 mmole) of 1,3-bis(benzyloxy)propan-2-yl stearate, 439 mg (0.625 mmole) of 20 wt % Pd(OH)$_2$/C and 125 mL of EtOAc were charged to a 3 neck round bottom flask equipped with a Teflon coated magnetic stir bar. A cold finger, with a bubbler filled with oil attached to it, and a bubbling stone connected to a 1:4 mixture of H$_2$/N$_2$ gas tank were affixed to the flask. H$_2$/N$_2$ was bubbled at 1.2 LPM into the flask until the disappearance of both starting material and mono-deprotected substrate as determined by TLC (~120 min). Once complete, the reaction mixture was filtered through a plug of Celite, which was then washed with 150 mL of EtOAc. The filtrate was placed in a refrigerator at 4° C. for 48 hrs. The precipitate from the filtrate (white and transparent needles) was filtered and dried under high vacuum yielding (2.12 g, 5.91 mmole, yield=47.3%) of 1,3-dihydroxypropan-2-yl stearate.

LRMS (ESI+) (m/z): calcd. for C$_{21}$H$_{43}$O$_4$ [M+H]$^+$, 359.32. found 359.47.

$^1$H NMR (600 MHz, CDCl$_3$): δ 4.92 (p, J=4.7 Hz, 1H), 3.88-3.78 (m, 4H), 2.40-2.34 (m, 2H), 2.09 (t, J=6.2 Hz, 2H), 1.64 (p, J=7.3 Hz, 2H), 1.25 (s, 25H), 0.88 (t, J=7.0 Hz, 3H) ppm.

$^{13}$C NMR (151 MHz, CDCl$_3$): δ 174.32, 75.20, 62.63, 34.57, 32.14, 29.91, 29.89, 29.87, 29.82, 29.68, 29.57, 29.47, 29.33, 25.17, 22.90, 14.32 ppm.

FIGS. 2-18 illustrate the effects of coating a variety of edible substrates with the compositions described herein. To form the coatings, solid mixtures of the compositions were first fully dissolved in ethanol at a concentration of 10 mg/mL (except where a different concentration is specified) to form a solution. The solution was then applied to the substrate either by spraying or dip coating, as detailed for each of the substrates below. The substrates were then dried on drying racks under ambient conditions (temperature in the range of 23° C.-27° C., humidity in the range of 40%-55%) until all of the solvent had evaporated, allowing the coatings to form over the substrates. The resultant coatings each had a thickness in the range of about 0.5 μm to 1 μm. For all mixtures described, PA was purchased from Sigma Aldrich, PA-1G was purchased from Tokyo Chemical Industry Co, PA-2G was prepared following the method of Example 1 above, SA was purchased from Sigma Aldrich, SA-1G was purchased from Alfa Aesar, SA-2G was prepared following the method of Example 3 above, MA was purchased from Sigma Aldrich, MA-1G was purchased from Tokyo Chemical Industry Co, OA was purchased from Sigma Aldrich, and EtPA was purchased from Sigma Aldrich.

Figure 2:
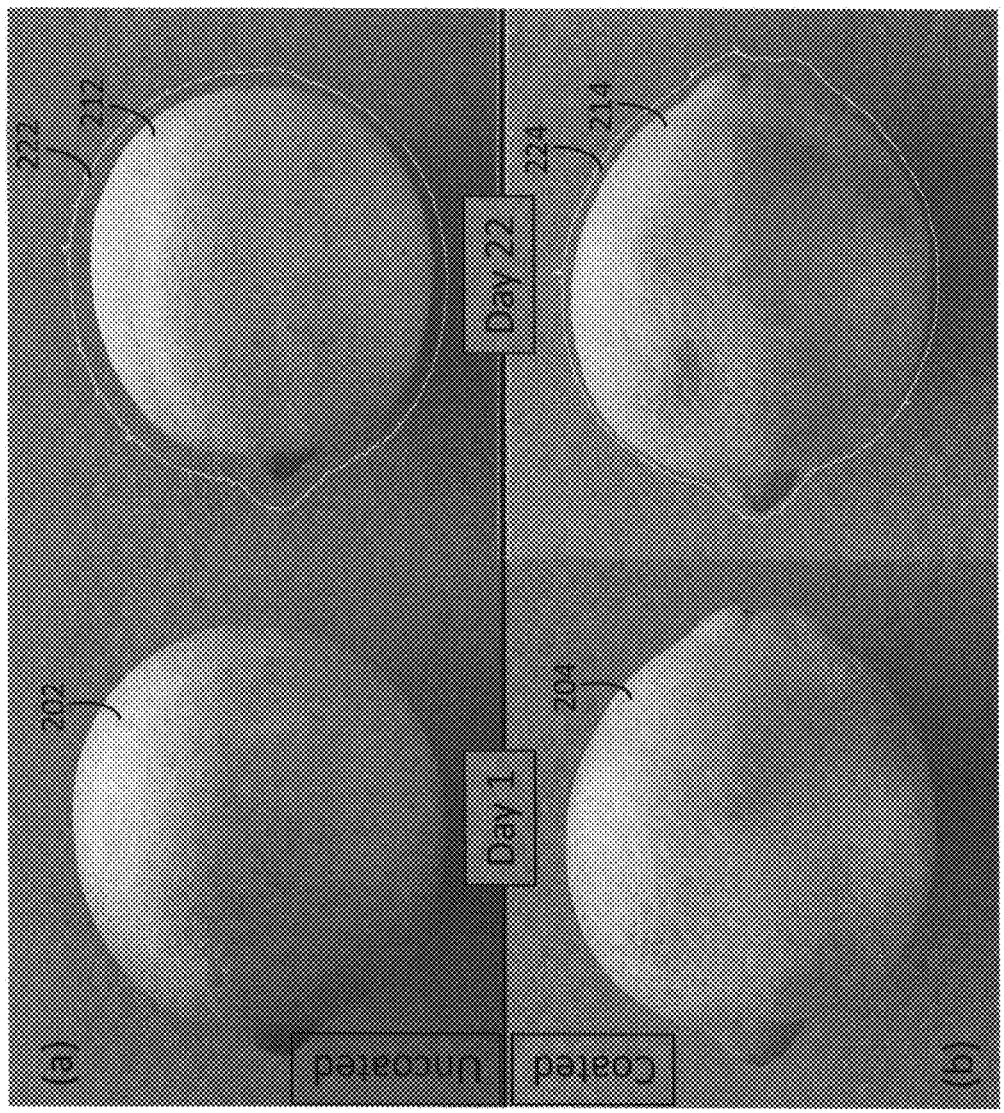
FIG. 2 shows high resolution time lapse photographs of lemons, both with and without coatings formed of compounds described herein.

Example 3—Effect of Compositions Comprising 1- and 2-Monoacylglycerides on Lemons FIG. 2 shows the effects of mass loss over time observed in lemons over the course of 3 weeks, both for uncoated lemons and for lemons which were coated with a composition described herein. The composition included PA-2G (compound of Formula I) and PA-1G (additive). The mass ratio and molar ratio of the PA-1G to PA-2G was about 0.33 (i.e., a molar ratio of about 25:75). The PA-2G was prepared

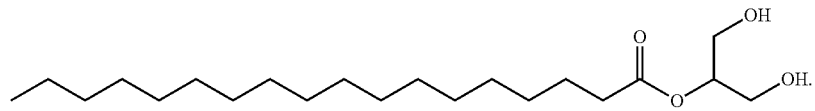 [SMILES: CCCCCCCCCCCCCCCCCC(=O)OC(CO)CO]

following the method of Example 1 above. The composition was dissolved in ethanol at a concentration of 10 mg/mL to form a solution, and the solution was applied to the surface of the lemons to form the coatings.

In order to form the coatings, the lemons were placed in a bag, and the solution containing the composition was poured into the bag. The bag was then sealed and lightly agitated until the entire surface of each lemon was wet. The lemons were then removed from the bag and allowed to dry on drying racks under ambient room conditions at a temperature in the range of about 23° C.-27° C. and humidity in the range of about 40%-55%. No visible residues or other visible precipitates were observed on the coated lemons.

The lemons were held at these same temperature and humidity conditions for the entire duration of the time they were tested for mass loss. 202 is a high resolution photograph of an uncoated lemon immediately after being picked (Day 1), and 204 is a high resolution photograph of a lemon immediately after being picked and coated on the same day. 212 and 214 are photographs of the uncoated and coated lemons, respectively, taken on Day 22, 21 days after photographs 202 and 204. In order to better visualize the cross-sectional area loss (which is directly related to mass loss), an overlay 222 of the outline of the untreated lemon on Day 1 is shown around 212, and an overlay 224 of the outline of the untreated lemon on Day 1 is shown around 214. The coated lemons had a cross sectional area greater than 90% of their original area (i.e., greater than 92% of their original area), whereas the uncoated lemons had a cross sectional area less than 80% of their original area (i.e., about 78% of their original area).

Figure 3:
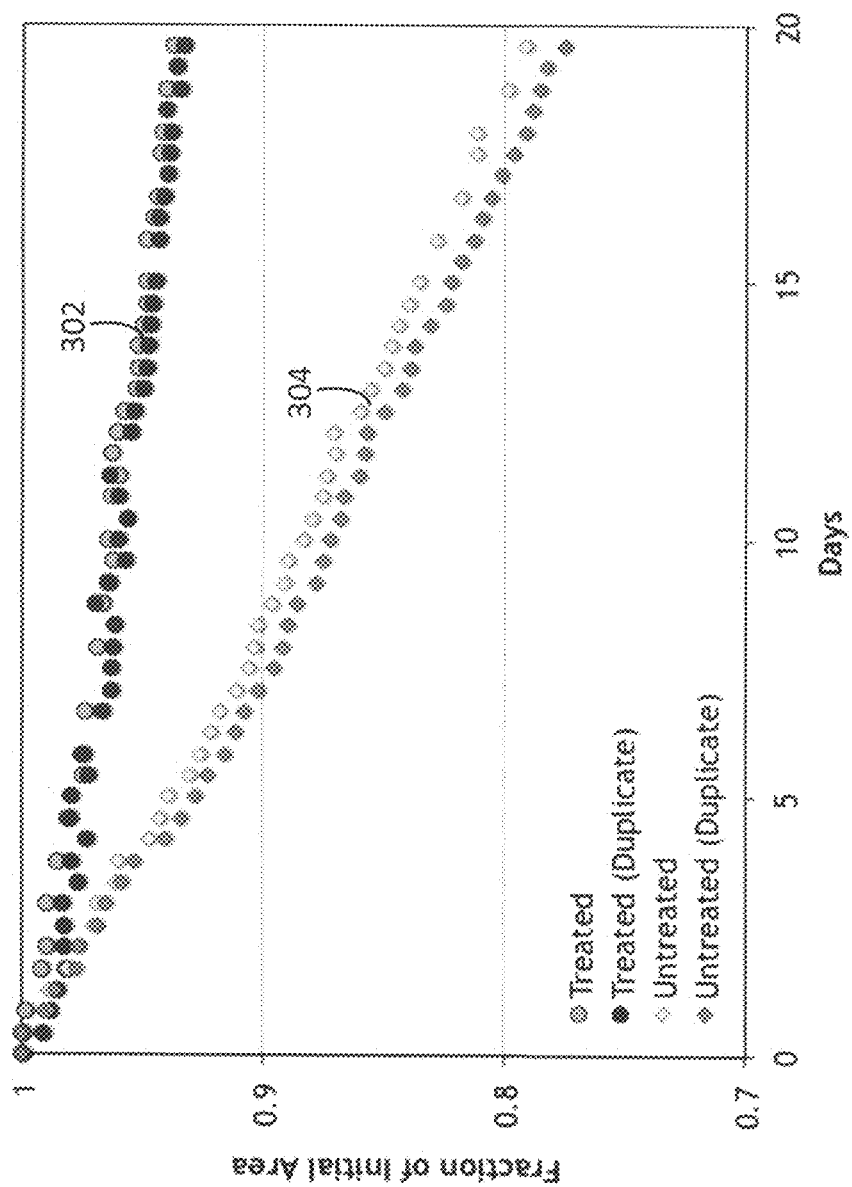
FIG. 3 is a normalized plot of the cross-sectional areas of the lemons of FIG. 2 as a function of time.

FIG. 3 shows plots for both coated (302) and uncoated (304) lemons indicating the reduction in cross sectional area as a function of time over a period of 20 days. Specifically, on each day, high resolution images of each of the lemons were taken and analyzed with image processing software (as in FIG. 2) to determine the ratio of the cross sectional area on the particular day to the initial cross sectional area of the lemon. As seen in FIG. 3, after 20 days, the coated lemons had a cross sectional area greater than 90% of their original area (in fact greater than 92% of their original area), whereas the uncoated lemons had a cross sectional area less than 80% of their original area.

Figure 4:
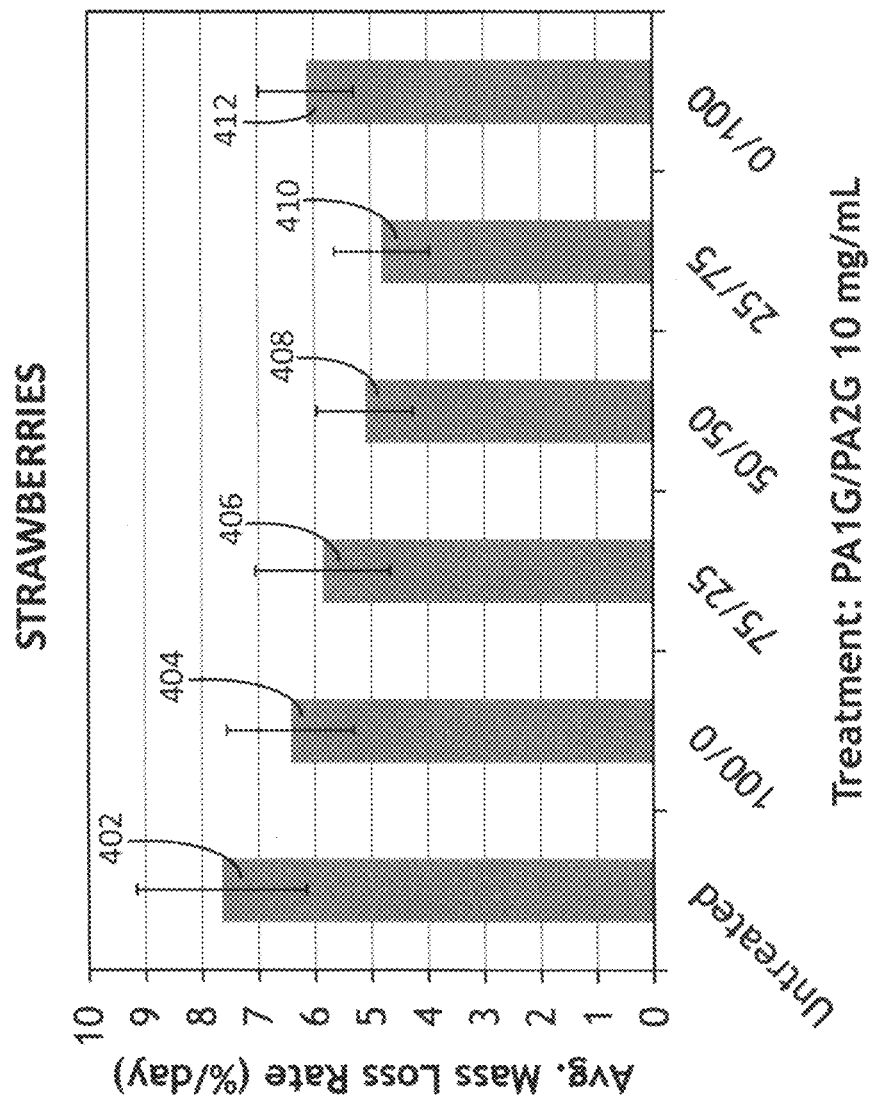
FIG. 4 is a plot of average mass loss rates of strawberries, both with and without coatings formed of compounds described herein.

Example 4—Effect of Compositions Comprising 1- and 2-Monoacylglycerides on Strawberries FIG. 4 is a graph showing average daily mass loss rates for strawberries coated with various mixtures of PA-2G (compound of Formula I) and PA-1G (additive) measured over the course of 4 days. Each bar in the graph represents average daily mass loss rates for a group of 15 strawberries. The strawberries corresponding to bar 402 were uncoated (control group). The strawberries corresponding to bar 404 were coated with a mixture that was substantially pure PA-1G. The strawberries corresponding to bar 406 were coated with a mixture that was about 75% PA-1G and 25% PA-2G by mass (mass ratio and molar ratio of PA-1G to PA-2G was about 3). The strawberries corresponding to bar 408 were coated with a mixture that was about 50% PA-1G and 50% PA-2G by mass (mass ratio and molar ratio of PA-1G to PA-2G was about 1). The strawberries corresponding to bar 410 were coated with a mixture that was about 25% PA-1G and 75% PA-2G by mass (mass ratio and molar ratio of PA-1G to PA-2G was about 0.33). The strawberries corresponding to bar 412 were coated with a mixture that was substantially pure PA-2G. The compositions were each dissolved in ethanol at a concentration of 10 mg/mL to form a solution, and the solution was applied to the surface of the strawberries to form the coatings.

In order to form the coatings, the strawberries were spray coated according to the following procedures. First, the strawberries were placed on drying racks. Solutions containing each of the coating compositions were placed in spray bottles which generated a fine mist spray. For each bottle, the spray head was held approximately six inches from the strawberries, and the strawberries were sprayed and then allowed to dry on the drying racks. The strawberries were kept under ambient room conditions at a temperature in the range of about 23° C.-27° C. and humidity in the range of about 40%-55% while they dried and for the entire duration of the time they were tested.

As shown in FIG. 4, the uncoated strawberries (402) exhibited an average mass loss rate of greater than 7.5% per day. The mass loss rates of the strawberries coated with the substantially pure PA-1G formulation (404) and the substantially pure PA-2G formulation (412) exhibited average daily mass loss rates between 6% and 6.5%, which was nominally better than the uncoated strawberries (402). However, the strawberries coated with substantially pure PA-1G or substantially pure PA-2G formulations (404 and 412, respectively) all exhibited heavy residues on their surfaces. The strawberries corresponding to bar 406 (PA-1G to PA-2G mass ratio of about 3) exhibited slightly improved mass loss rates, slightly less than 6% per day, but still exhibited moderate residues on their surfaces. The strawberries corresponding to bars 408 and 410 (PA-1G to PA-2G mass ratios of about 1 and 0.33, respectively) exhibited substantially improved mass loss rates; the strawberries corresponding to bar 408 exhibited average daily mass loss rates of just over 5%, while the strawberries corresponding to bar 410 exhibited average daily mass loss rates of under 5%, with none of the strawberries in either of these groups exhibiting visible residues on their surfaces.

Figure 5:
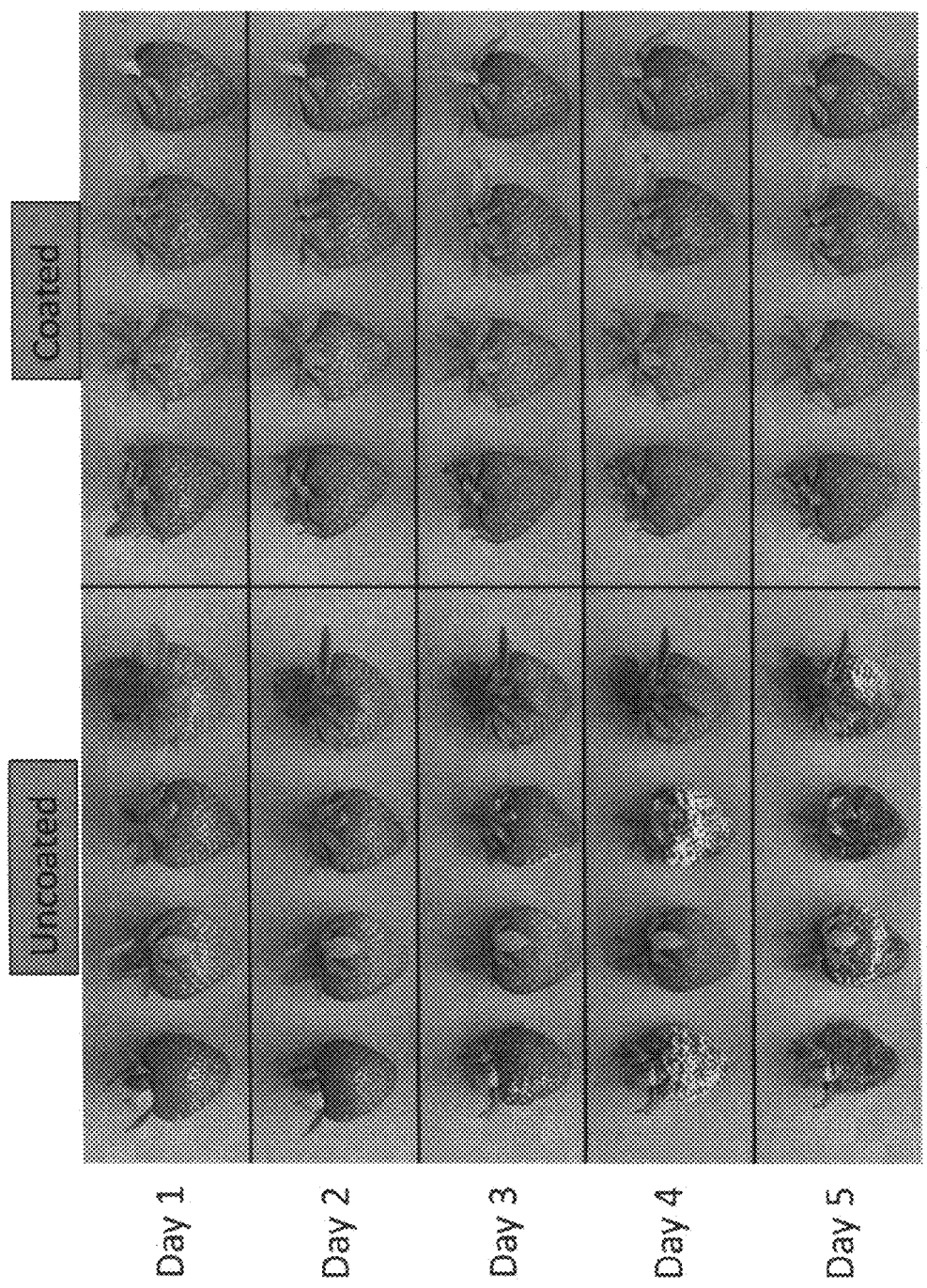
FIG. 5 shows high resolution time lapse photographs of strawberries, both with and without coatings formed of compounds described herein.

FIG. 5 shows high resolution photographs of 4 coated and 4 uncoated strawberries over the course of 5 days at the temperature and humidity conditions described above, where the coated strawberries were coated with mixtures having a PA-1G to PA-2G mass ratio and molar ratio of about 0.33 (i.e., about 25:75) as in bar 410 in FIG. 4. As seen, the uncoated strawberries began to exhibit fungal growth and discoloration by day 3, and were mostly covered in fungus by day 5. In contrast, the coated strawberries did not exhibit any fungal growth by day 5 and were largely similar in overall color and appearance on day 1 and day 5.

Figure 6:
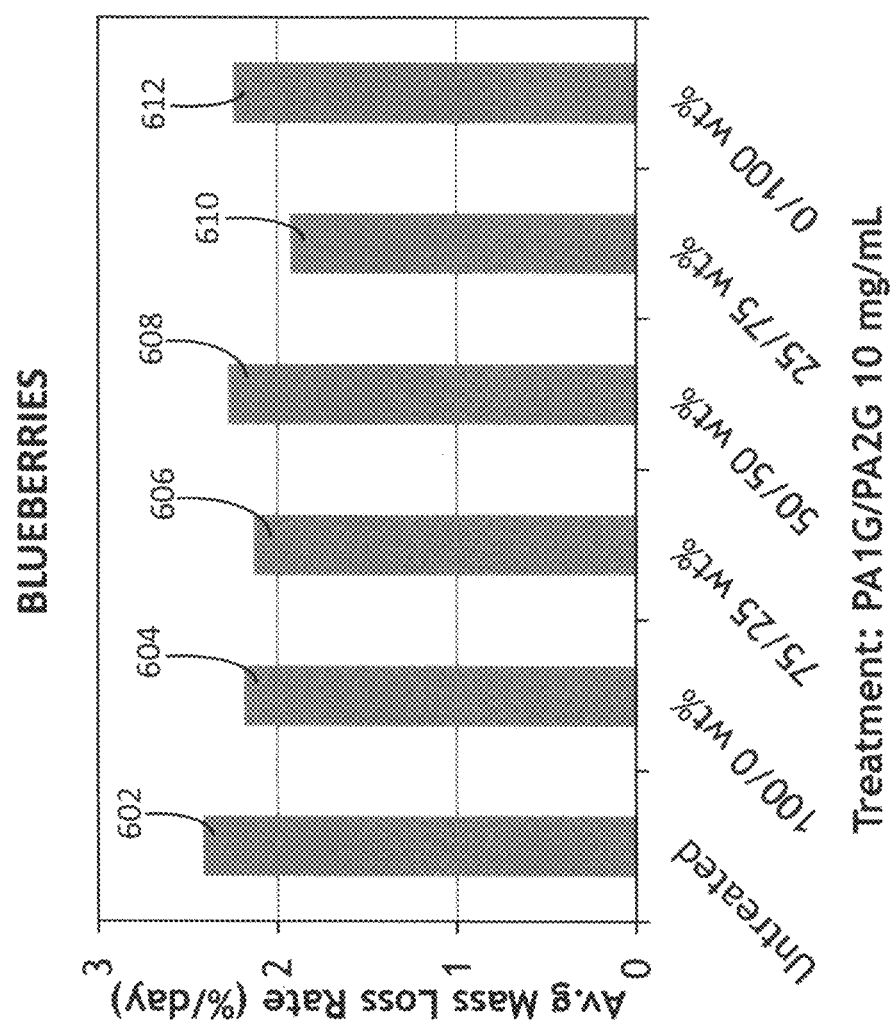
FIG. 6 is a plot of average mass loss rates of blueberries, both with and without coatings formed of 1-glycerol and 2-glycerol esters of palmitic acid.

Example 5—Effect of Compositions Comprising 1- and 2-Monoacylglycerides on Blueberries FIG. 6 is a graph showing average daily mass loss rates for blueberries coated with various mixtures of PA-2G (compound of Formula I) and PA-1G (additive) measured over the course of several days. Each bar in the graph represents average daily mass loss rates for a group of 60 blueberries. The blueberries corresponding to bar 602 were uncoated (control group). The blueberries corresponding to bar 604 were coated with a mixture that was substantially pure PA-1G. The blueberries corresponding to bar 606 were coated with a mixture that was about 75% PA-1G and 25% PA-2G by mass (i.e., the mass ratio and molar ratio of PA-1G to PA-2G was about 3). The blueberries corresponding to bar 608 were coated with a mixture that was about 50% PA-1G and 50% PA-2G by mass (i.e., the mass ratio and molar ratio of PA-1G to PA-2G was about 1). The blueberries corresponding to bar 610 were coated with a mixture that was about 25% PA-1G and 75% PA-2G by mass (mass ratio and molar ratio of PA-1G to PA-2G was about 0.33). The blueberries corresponding to bar 612 were coated with a mixture that was substantially pure PA-2G. The compositions were each dissolved in ethanol at a concentration of 10 mg/mL to form a solution, and the solution was applied to the surface of the blueberries to form the coatings.

In order to form the coatings, the blueberries were placed in bags, and the solution containing the composition was poured into the bag. The bag was then sealed and lightly agitated until the entire surface of each blueberry was wet. The blueberries were then removed from the bag and allowed to dry on drying racks. The blueberries were kept under ambient room conditions at a temperature in the range of about 23° C.-27° C. and humidity in the range of about 40%-55% while they dried and for the entire duration of the time they were tested.

As shown in FIG. 6, the uncoated blueberries (602) exhibited an average mass loss rate of nearly 2.5% per day. The mass loss rates of the blueberries coated with the substantially pure PA-1G formulation (604) and the substantially pure PA-2G formulation (612), as well as the blueberries corresponding to bars 606 (PA-1G to PA-2G ratio of about 3) and 608 (PA-1G to PA-2G ratio of about 1) exhibited average daily mass loss rates between 2.1% and 2.3%, which was nominally better than the uncoated blueberries (602). However, the blueberries coated with substantially pure PA-1G or substantially pure PA-2G formulations (604 and 612, respectively) all exhibited heavy residues on their surfaces, and the blueberries corresponding to bar 606 (PA-1G to PA-2G mass ratio of about 3) exhibited moderate residues on their surfaces. The blueberries corresponding to bar 610 (PA-1G to PA-2G mass ratios of about 0.33) exhibited mass loss rates under 2%, which was a substantial improvement over the uncoated blueberries (602), and also did not exhibit any visible residues on their surfaces.

Figure 7:
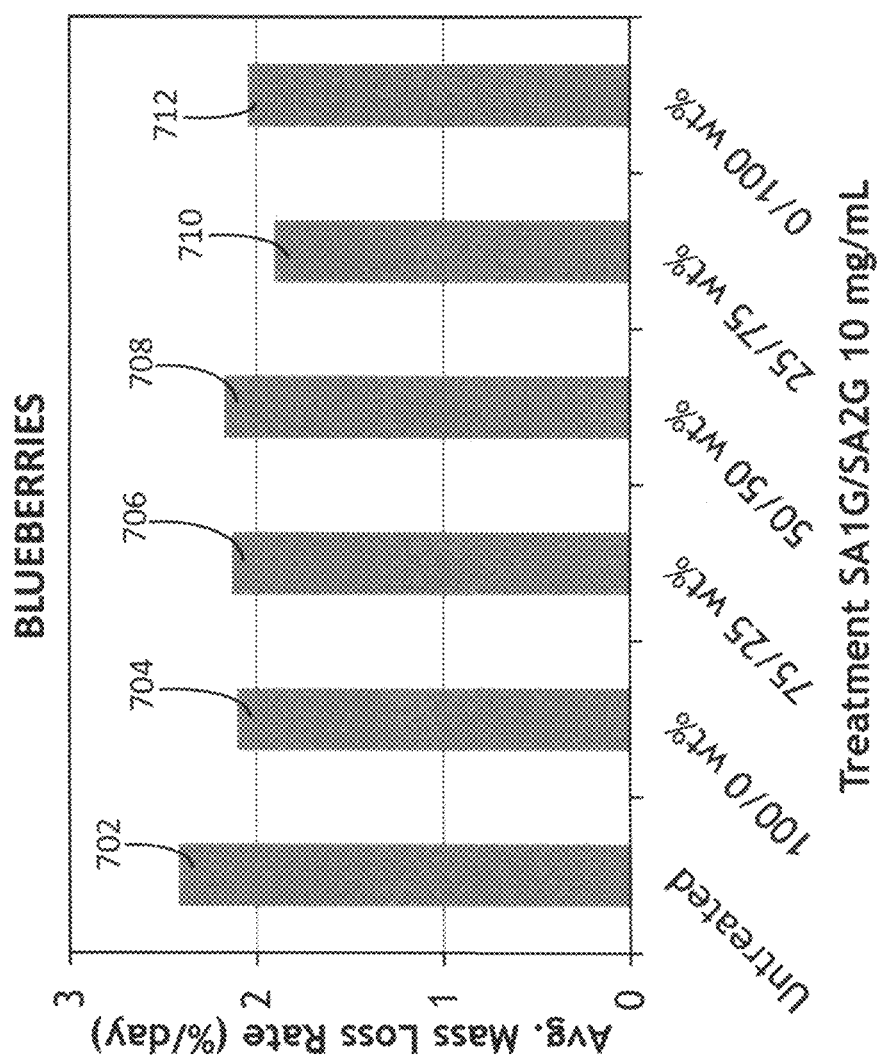
FIG. 7 is a plot of average mass loss rates of blueberries, both with and without coatings formed of 1-glycerol and 2-glycerol esters of stearic acid.

FIG. 7 is a graph showing average daily mass loss rates for blueberries coated with various mixtures of SA-2G (compound of Formula I) and SA-1G (additive) measured over the course of several days. Each bar in the graph represents average daily mass loss rates for a group of 60 blueberries. The blueberries corresponding to bar 702 were uncoated (control group). The blueberries corresponding to bar 704 were coated with a mixture that was substantially pure SA-1G. The blueberries corresponding to bar 706 were coated with a mixture that was about 75% SA-1G and 25% SA-2G by mass (mass ratio and molar ratio of SA-1G to SA-2G was about 3). The blueberries corresponding to bar 708 were coated with a mixture that was about 50% SA-1G and 50% SA-2G by mass (mass ratio and molar ratio of SA-1G to SA-2G was about 1). The blueberries corresponding to bar 710 were coated with a mixture that was about 25% SA-1G and 75% SA-2G by mass (mass ratio and molar ratio of SA-1G to SA-2G was about 0.33). The blueberries corresponding to bar 712 were coated with a mixture that was substantially pure SA-2G. The compositions were each dissolved in ethanol at a concentration of 10 mg/mL to form a solution, and the solution was applied to the surface of the blueberries to form the coatings.

In order to form the coatings, the blueberries were placed in bags, and the solution containing the composition was poured into the bag. The bag was then sealed and lightly agitated until the entire surface of each blueberry was wet. The blueberries were then removed from the bag and allowed to dry on drying racks. The blueberries were kept under ambient room conditions at a temperature in the range of about 23° C.-27° C. and humidity in the range of about 40%-55% while they dried and for the entire duration of the time they were tested.

As shown in FIG. 7, the results for SA-1G/SA-2G mixtures were similar to those for PA-1G/PA-2G mixtures. The uncoated blueberries (702) exhibited an average mass loss rate of about 2.4% per day. The mass loss rates of the blueberries coated with the substantially pure SA-1G formulation (704) and the substantially pure SA-2G formulation (712), as well as the blueberries corresponding to bars 706 (SA-1G to SA-2G ratio of about 3) and 708 (SA-1G to SA-2G ratio of about 1) exhibited average daily mass loss rates between 2.1% and 2.2%, which was nominally better than the uncoated blueberries (702). However, the blueberries coated with substantially pure SA-1G or substantially pure SA-2G formulations (704 and 712, respectively) all exhibited heavy residues on their surfaces, and the blueberries corresponding to bar 706 (SA-1G to SA-2G mass ratio of about 3) exhibited moderate residues on their surfaces. The blueberries corresponding to bar 710 (SA-1G to SA-2G mass ratios of about 0.33) exhibited average mass loss rates of about 1.8%, which was a substantial improvement over the uncoated blueberries (702), and also did not exhibit any visible residues on their surfaces.

Figure 8:
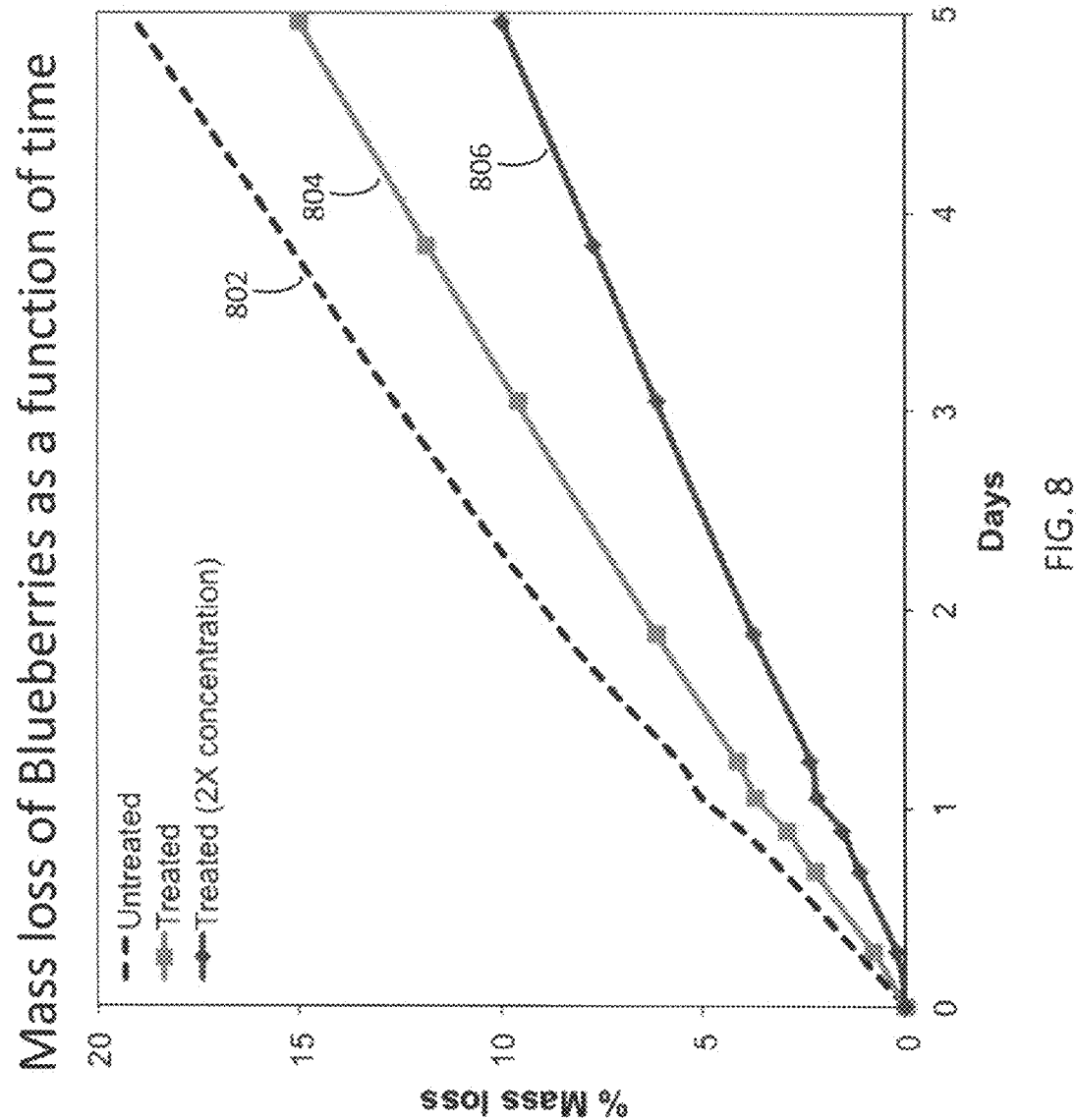
FIG. 8 is a plot of the percent mass loss of blueberries as a function of time.

FIG. 8, which illustrates the results of another blueberry study, shows plots of the percent mass loss over the course of 5 days in uncoated blueberries (802), blueberries coated using a first solution of 10 mg/mL of compounds dissolved in ethanol (804), and blueberries coated using a second solution of 20 mg/mL of compounds dissolved in ethanol (806). The compounds in both the first and second solutions included a mixture of PA-1G and PA-2G, where the mass ratio and molar ratio of PA-1G to PA-2G was about 0.33 (i.e., a ratio of 25:75 as with bar 610 in FIG. 6). To form the coatings over the coated blueberries, the following dip coating procedures were used. Each blueberry was picked up with a set of tweezers and individually dipped in the solution for approximately 1 second or less, after which the blueberry was placed on a drying rack and allowed to dry. The blueberries were kept under ambient room conditions at a temperature in the range of about 23° C.-27° C. and humidity in the range of about 40%-55% while they dried and for the entire duration of the time they were tested. Mass loss was measured by carefully weighing the blueberries each day, where the reported percent mass loss was equal to the ratio of mass reduction to initial mass. As shown, the percent mass loss for uncoated blueberries was almost 20% after 5 days, whereas the percent mass loss for blueberries coated with the 10 mg/mL solution was less than 15% after 5 days, and the percent mass loss for blueberries coated with the 20 mg/mL solution was less than 10% after 5 days.

Figure 9:
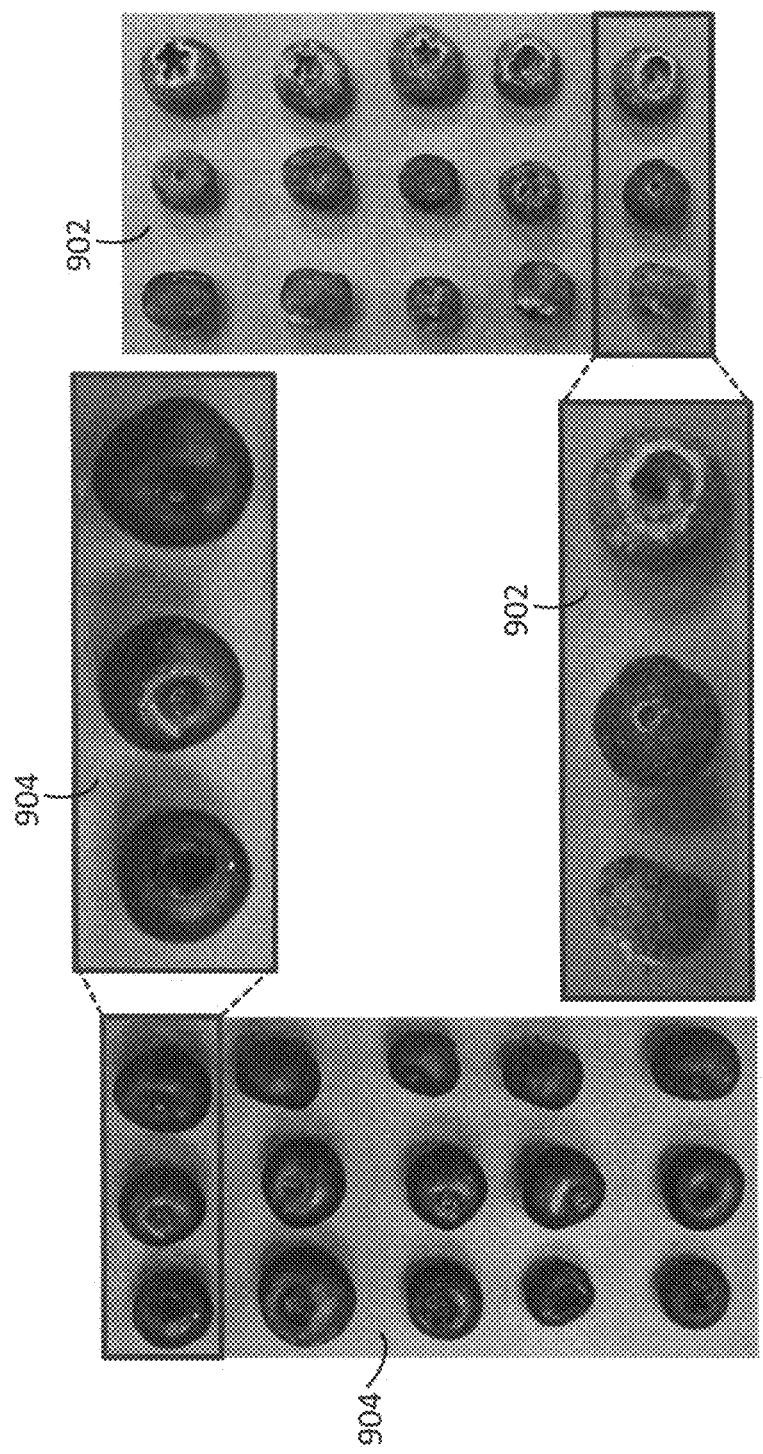
FIG. 9 shows high resolution photographs of blueberries, both with and without coatings formed of compounds described herein.

FIG. 9 shows high resolution photographs of the uncoated blueberries (802) from the study in FIG. 8, and of the blueberries coated with the 10 mg/mL solution of a 25:75 mass ratio and molar ratio (i.e., 0.33) of PA-1G to PA-2G (804) from the study of FIG. 8, taken at day 5. The skins of the uncoated blueberries 802 were highly wrinkled as a result of mass loss of the blueberries, whereas the skins of the coated blueberries remained very smooth.

Figure 10:
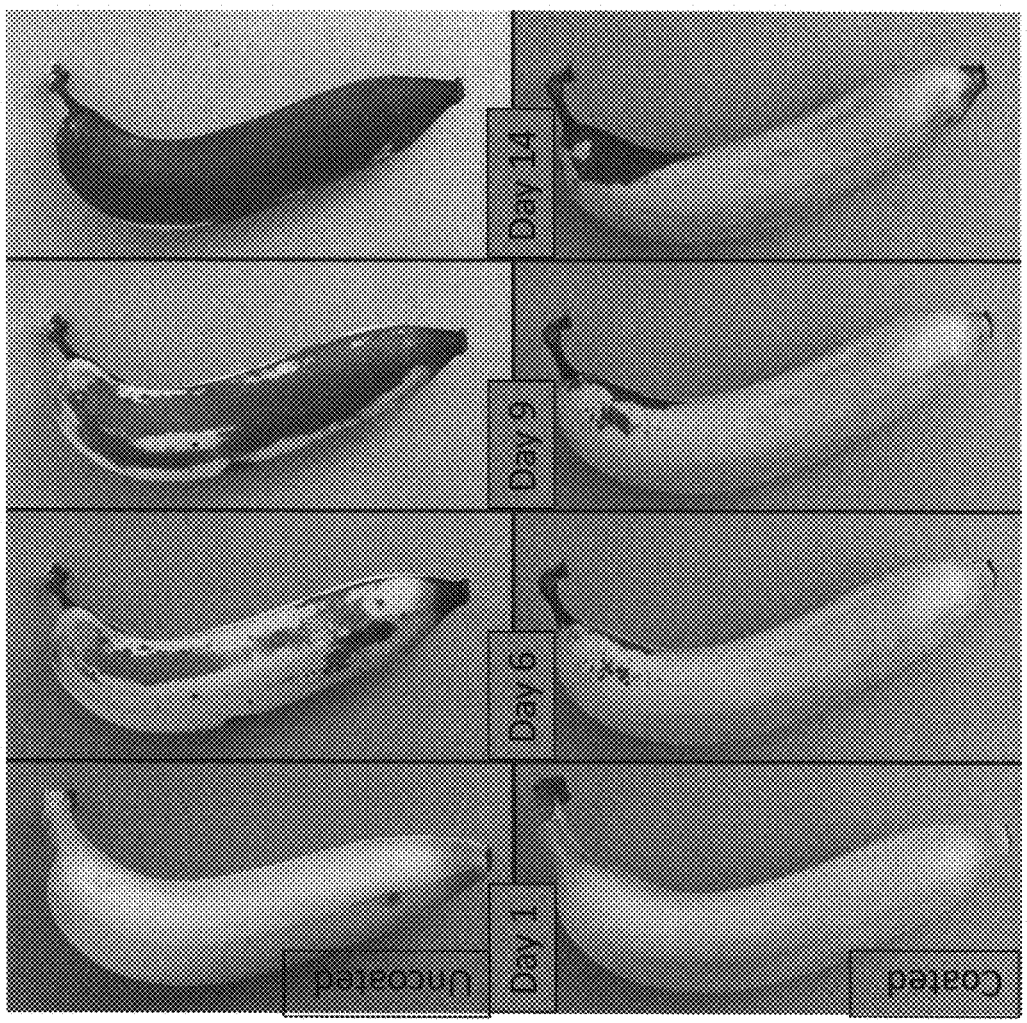
FIG. 10 shows high resolution time lapse photographs of bananas, both with and without coatings formed of compounds described herein.

Example 6—Effect of Compositions Comprising 1- and 2-Monoacylglycerides on Bananas FIG. 10 shows high resolution photographs of coated and uncoated bananas over the course of 14 days, where the coatings were formed from a composition dissolved in a solvent. The composition included PA-2G (compound of Formula I) and PA-1G (additive). The mass ratio and molar ratio of the PA-1G to PA-2G was about 0.33 (i.e., about 25:75). The composition was dissolved in ethanol at a concentration of 10 mg/mL to form a solution, and the solution was applied to the surface of the lemons to form the coatings.

In order to form the coatings, the bananas were placed in a bag, and the solution containing the composition was poured into the bag. The bag was then sealed and lightly agitated until the entire surface of each banana was wet. The bananas were then removed from the bag and allowed to dry on drying racks under ambient room conditions at a temperature in the range of about 23° C.-27° C. and humidity in the range of about 40%-55%. The bananas were held at these same temperature and humidity conditions for the entire duration of the time they were tested. As shown, the coatings clearly served as an effective barrier to oxidation, thereby preventing discoloration of the bananas and slowing down the ripening process. For example, for the uncoated banana, over 30% of the peel was a light brown color at Day 6, over 80% of the peel was a light brown color at Day 9, and almost the entire peel was a darker brown color by Day 14. On the other hand, for the coated banana, only slight browning and discoloration were observed even by Day 14.

Figure 11:
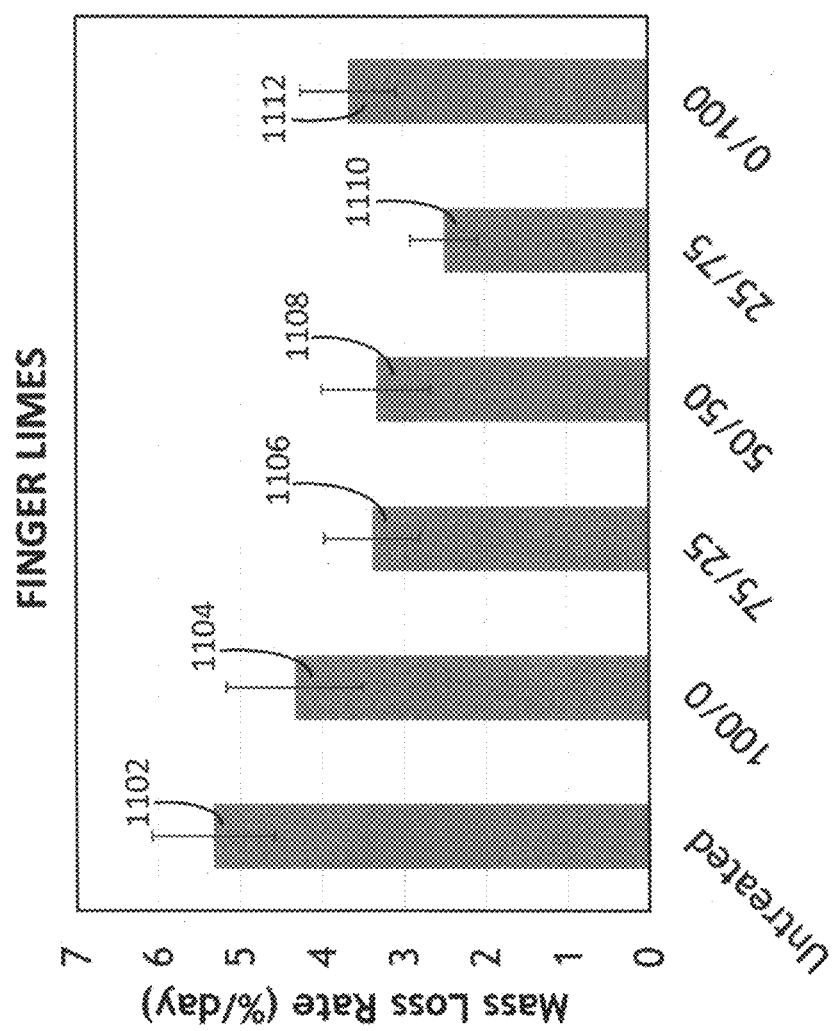
FIG. 11 shows a plot of mass loss rates per day for finger limes coated with 1-glycerol and 2-glycerol esters of palmitic acid.

Example 7—Effect of Compositions Comprising 1- and 2-Monoacylglycerides on Finger Limes FIG. 11 is a graph showing average daily mass loss rates for finger limes coated with various mixtures of PA-2G (compound of Formula I) and PA-1G (additive) measured over the course of several days. Each bar in the graph represents average daily mass loss rates for a group of 24 finger limes. The finger limes corresponding to bar 1102 were uncoated (control group). The finger limes corresponding to bar 1104 were coated with a mixture that was substantially pure PA-1G. The finger limes corresponding to bar 1106 were coated with a mixture that was about 75% PA-1G and 25% PA-2G by mass (mass ratio and molar ratio of PA-1G to PA-2G was about 3). The finger limes corresponding to bar 1108 were coated with a mixture that was about 50% PA-1G and 50% PA-2G by mass (mass ratio and molar ratio of PA-1G to PA-2G was about 1). The finger limes corresponding to bar 1110 were coated with a mixture that was about 25% PA-1G and 75% PA-2G by mass (mass ratio and molar ratio of PA-1G to PA-2G was about 0.33). The finger limes corresponding to bar 1112 were coated with a mixture that was substantially pure PA-2G. The compositions were each dissolved in ethanol at a concentration of 10 mg/mL to form a solution, and the solution was applied to the surface of the finger limes to form the coatings.

In order to form the coatings, the finger limes were placed in bags, and the solution containing the composition was poured into the bag. The bag was then sealed and lightly agitated until the entire surface of each finger lime was wet. The finger limes were then removed from the bag and allowed to dry on drying racks. The finger limes were kept under ambient room conditions at a temperature in the range of about 23° C.-27° C. and humidity in the range of about 40%-55% while they dried and for the entire duration of the time they were tested.

As shown in FIG. 11, the uncoated finger limes (1102) exhibited an average mass loss rate of over 5% per day. The mass loss rates of the finger limes coated with the substantially pure PA-1G formulation (1104) and the substantially pure PA-2G formulation (1112) exhibited average daily mass loss rates of just over 4% and just under 4%, respectively, which was nominally better than the uncoated finger limes (1102). However, the finger limes coated with substantially pure PA-1G or substantially pure PA-2G formulations (1104 and 1112, respectively) all exhibited heavy residues on their surfaces. The finger limes corresponding to bar 1106 (75:25 mass ratio of PA-1G to PA-2G, or a mass ratio of about 3) showed improved results, yielding an average daily mass loss rate of less than 3.5% but still exhibiting moderate residues on their surfaces. The finger limes corresponding to bars 1108 and 1110 (PA-1G to PA-2G mass ratios of about 1 (50:50) and 0.33 (25:75), respectively) exhibited mass loss rates under 3.5% and under 2.6%, respectively, which was a substantial improvement over the uncoated finger limes (1102), and also did not exhibit any visible residues on their surfaces.

Figure 12:
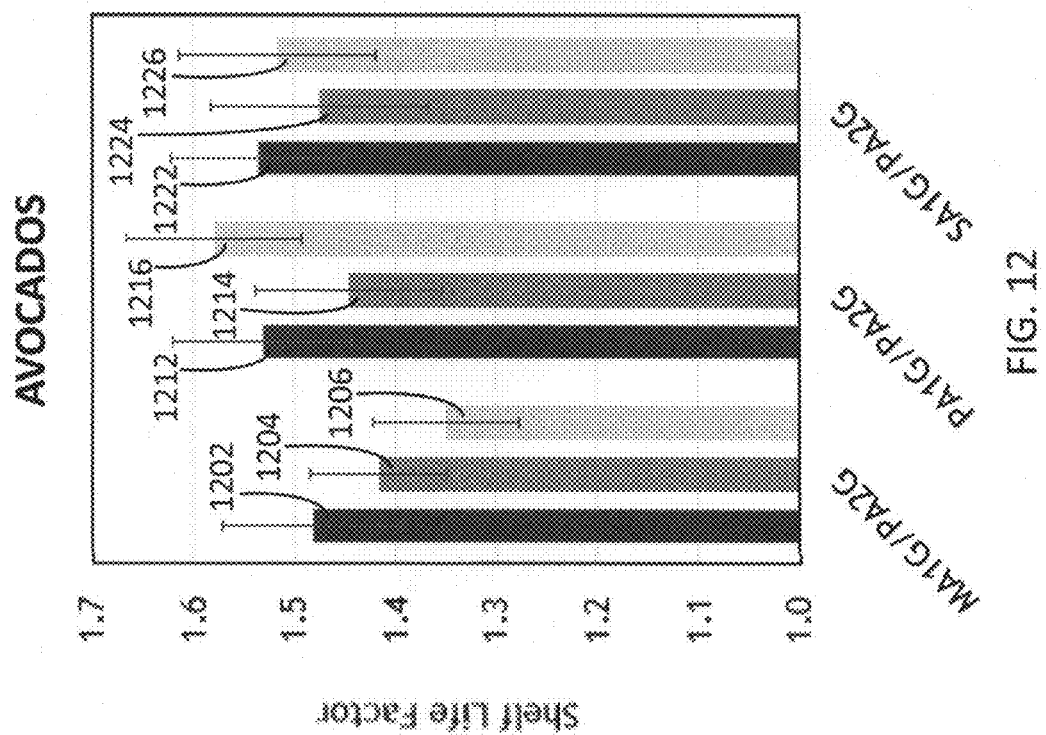
FIG. 12 shows a plot of the shelf life factor of avocados coated with coatings formed of 2-glycerol esters of palmitic acid and 1-glycerol esters of myristic acid, palmitic acid, and stearic acid.

Example 8—Effect of Compositions Comprising 1- and 2-Monoacylglycerides on Avocados FIG. 12 is a graph showing the shelf life factor for avocados coated with various mixtures of PA-2G (compound of Formula I) and a 1-monoacylglyceride additive (bars 1202, 1204, and 1206 are for MA-1G; bars 1212, 1214, and 1216 are for PA-1G; bars 1222, 1224, and 1226 are for SA-1G). As used herein, the term "shelf life factor" is defined as the ratio of the average mass loss rate of uncoated produce (measured for a control group) to the average mass loss rate of the corresponding coated produce. Hence a larger shelf life factor corresponds to a greater reduction in average mass loss rate. Bars 1202, 1212, and 1222 correspond to a 25:75 mixture of 1-monoacylglycerides to PA-2G (molar ratio of 1-monoacylglycerides to PA-2G of about 0.33). Bars 1204, 1214, and 1224 correspond to a 50:50 mixture of 1-monoacylglycerides to PA-2G (molar ratio of 1-monoacylglycerides to PA-2G of about 1). Bars 1206, 1216, and 1226 correspond to a 75:25 mixture of 1-monoacylglycerides to PA-2G (molar ratio of 1-monoacylglycerides to PA-2G of about 3).

Each bar in the graph represents a group of 30 avocados. All coatings were formed by dipping the avocados in a solution comprising the associated mixture dissolved in substantially pure ethanol at a concentration of 5 mg/mL, placing the avocados on drying racks, and allowing the avocados to dry under ambient room conditions at a temperature in the range of about 23° C.-27° C. and humidity in the range of about 40%-55%. The avocados were held at these same temperature and humidity conditions for the entire duration of the time they were tested.

As seen, for both the MA-1G/PA-2G and SA-1G/PA-2G combinations, the greatest shelf life factor was achieved for a 1-monoacylglyceride to PA-2G molar ratio of about 0.33. Furthermore, for both of these combinations, the avocados coated with the 25:75 (i.e., molar ratio of about 0.33) and 50:50 (i.e., a molar ratio of about 1) molar ratio mixtures did not exhibit any visible residues on their surfaces, whereas the avocados with 75:25 mixtures exhibited moderate to heavy residues. For the case of the PA-1G/PA-2G combinations, although the shelf life factor for the avocados coated with the 75:25 mixture was greater than that of the avocados coated with the 25:75 mixture, the avocados coated with the 75:25 mixture exhibited moderate to heavy residues, whereas the avocados coated with the 25:75 and 50:50 mixtures exhibited no visible residues. Although not shown, no coatings formed of any mixtures containing only a single constituent of any of the compounds illustrated in FIG. 12 were undetectable to the human eye.

Figure 13:
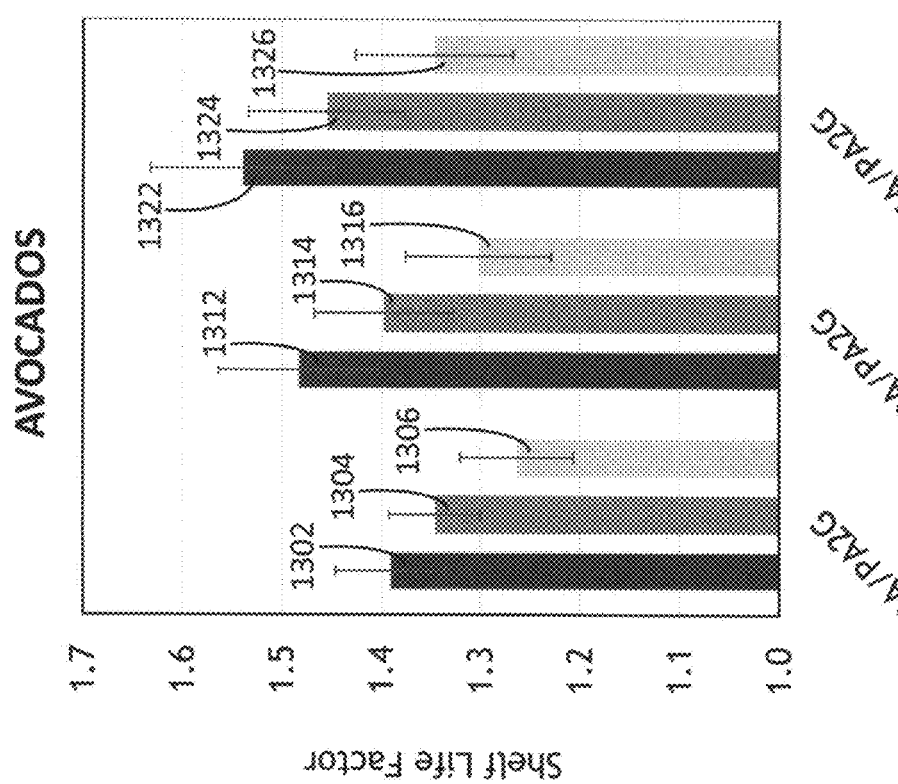
FIG. 13 shows a plot of the shelf life factor of avocados coated with coatings formed of 2-glycerol esters of palmitic acid and myristic acid, palmitic acid, and stearic acid.

Example 9—Effect of Compositions Comprising 2-Monoacylglycerides and Additives on Avocados FIG. 13 is a graph showing the shelf life factor for avocados coated with various mixtures of PA-2G (compound of Formula I) and a fatty acid additive (bars 1302, 1304, and 1306 are for MA; bars 1312, 1314, and 1316 are for PA; bars 1322, 1324, and 1326 are for SA). Bars 1302, 1312, and 1322 correspond to a 25:75 mixture of fatty acid to PA-2G (molar ratio of fatty acid to PA-2G of about 0.33). The mass ratios are about 0.23, 0.25, and 0.28, respectively. Bars 1304, 1314, and 1324 correspond to a 50:50 mixture of fatty acid to PA-2G (molar ratio of fatty acid to PA-2G of about 1). The mass ratios are about 0.35, 0.39, and 0.43, respectively. Bars 1306, 1316, and 1326 correspond to a 75:25 mixture of fatty acid to PA-2G (molar ratio of fatty acid to PA-2G of about 3). The mass ratios are about 2.1, 2.3, and 2.6, respectively.

Each bar in the graph represents a group of 30 avocados. All coatings were formed by dipping the avocados in a solution comprising the associated mixture dissolved in substantially pure ethanol at a concentration of 5 mg/mL, placing the avocados on drying racks, and allowing the avocados to dry under ambient room conditions at a temperature in the range of about 23° C.-27° C. and humidity in the range of about 40%-55%. The avocados were held at these same temperature and humidity conditions for the entire duration of the time they were tested.

As seen, for all three of these combinations, the greatest shelf life factor was achieved for a fatty acid to PA-2G molar ratio of about 0.33. Furthermore, for all of these combinations, the avocados coated with the 25:75 and 50:50 molar ratio mixtures did not exhibit any visible residues on their surfaces, whereas the avocados with 75:25 mixtures exhibited moderate to heavy residues. Although not shown, no coatings formed of any mixtures containing only a single constituent of any of the compounds illustrated in FIG. 13 were undetectable to the human eye.

Figure 14:
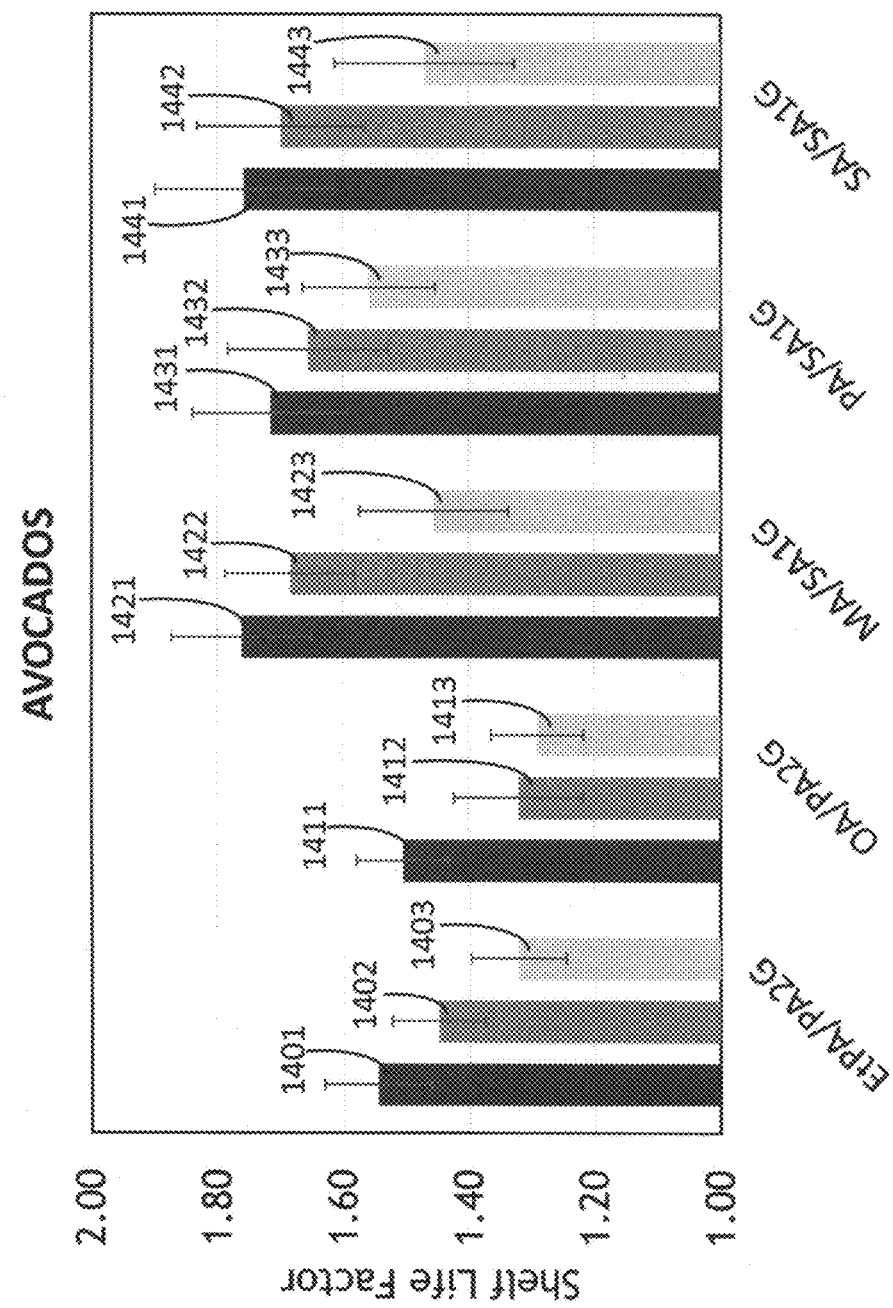
FIG. 14 shows a plot of the shelf life factor for avocados coated with compositions comprising 2-glycerol esters of palmitic acid combined with ethyl palmitate and oleic acid.

FIG. 14 is a graph showing the shelf life factor for avocados coated with various other compounds. Each bar in the graph represents a group of 30 avocados. All coatings were formed by dipping the avocados in a solution comprising the associated mixture dissolved in substantially pure ethanol at a concentration of 5 mg/mL, placing the avocados on drying racks, and allowing the avocados to dry under ambient room conditions at a temperature in the range of about 23° C.-27° C. and humidity in the range of about 40%-55%. The avocados were held at these same temperature and humidity conditions for the entire duration of the time they were tested.

Bars 1401-1403 correspond to mixtures of PA-2G (compound of Formula I) with ethyl palmitate as an additive. Bars 1411-1413 correspond to mixtures of PA-2G (compound of Formula I) with oleic acid (unsaturated fatty acid) as an additive. Bars 1401 and 1411 correspond to a 25:75 mixture of additive to PA-2G (molar ratio of additive to PA-2G of about 0.33). The mass ratios are both about 0.86. Bars 1402 and 1412 correspond to a 50:50 mixture of additive to PA-2G (molar ratio of additive to PA-2G of about 1). The mass ratios both are about 0.43. Bars 1403 and 1413 correspond to a 75:25 mixture of additive to PA-2G (molar ratio of additive to PA-2G of about 3). The mass ratios are both about 2.58. As seen for the combinations of PA-2G and EtPA as well as for the combinations of PA-2G and OA, the greatest shelf life factor was achieved with additive to PA-2G molar ratio of about 0.33.

Bars 1421-1423, 1431-1433, and 1441-1443 correspond to coatings formed of a compound of Formula II (e.g., a 1-monoacylglyceride) and an additive (e.g., a fatty acid). Bars 1421-1423 correspond to mixtures of SA-1G (compound of Formula II) with myristic acid as an additive. Bars 1431-1433 correspond to mixtures of SA-1G (compound of Formula II) with palmitic acid as an additive. Bars 1441-1443 correspond to mixtures of SA-1G (compound of Formula II) with stearic acid as an additive. Bars 1421, 1431, and 1441 correspond to a 25:75 mixture of fatty acid to SA-1G (molar ratio of fatty acid to SA-1G of about 0.33). The mass ratios are about 0.21, 0.23, and 0.26, respectively. Bars 1422, 1432, and 1442 correspond to a 50:50 mixture of fatty acid to SA-1G (molar ratio of fatty acid to SA-1G of about 1). The mass ratios are about 0.32, 0.35, and 0.40, respectively. Bars 1423, 1443, and 1443 correspond to a 75:25 mixture of fatty acid to SA-1G (molar ratio of fatty acid to SA-1G of about 3). The mass ratios are about 1.89, 2.13, and 2.37, respectively. As seen for all three of these combinations, the greatest shelf life factor was achieved for a fatty acid to SA-1G molar ratio of about 0.33.

Figure 15:
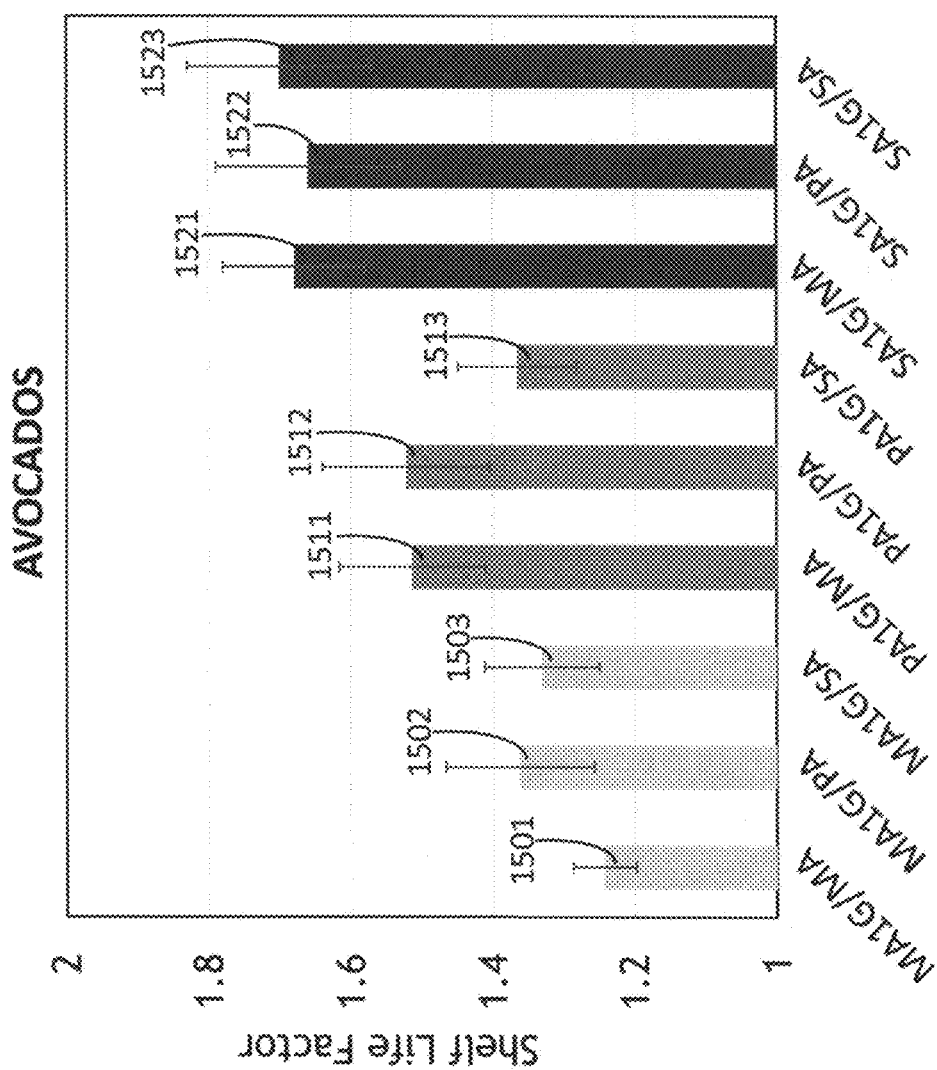
FIG. 15 shows a plot of the shelf life factor for avocados coated with 1-glycerol esters of myristic acid, palmitic acid, and stearic acid in combination with myristic acid, palmitic acid, and stearic acid.

Still referring to FIG. 14, while the largest shelf life factors for combinations of SA-1G and a fatty acid were observed for an additive to SA-1G molar ratio of about 0.33, the additive to SA-1G molar ratio corresponding to the least amount of residues on the surface was about 42:58 for each of the combinations. The same was found to also be true for coatings formed of other combinations of fatty acids and 1-monoacylglycerides, for which results are shown in FIG. 15. For the various combinations of fatty acids and 1-monoacylglycerides that were tested, some always exhibited some level of residues, while for some there was a very narrow range of ratios for which visible residues were not observed. However, without wishing to be bound by theory, because the formation of residues is sensitive to changes in drying conditions (e.g., temperature and pressure), having such a narrow process window likely results in lower reproducibility in terms of suppressing visible residues over a wide range of drying conditions.

FIG. 15 is a graph showing the shelf life factor for avocados each coated with a mixture including a compound of Formula II and a fatty acid additive. All mixtures were a 1:1 mix by mole ratio of the compound of Formula II and the fatty acid. Bars 1501-1503 correspond to coatings with MA-1G as the compound of Formula II and MA (1501), PA (1502), and SA (1503) as the fatty acid additive. The mass ratios are about 1.32, 1.18, and 1.06, respectively. Bars 1511-1513 correspond to coatings with PA-1G as the compound of Formula II and MA (1511), PA (1512), and SA (1513) as the fatty acid additive. The mass ratios are about 1.44, 1.29, and 1.16, respectively. Bars 1521-1523 correspond to coatings with SA-1G as the compound of Formula II and MA (1521), PA (1522), and SA (1523) as the fatty acid additive. The mass ratios are about 1.57, 1.39, and 1.25, respectively. Each bar in the graph represents a group of 30 avocados. All coatings were formed by dipping the avocados in a solution comprising the associated mixture dissolved in substantially pure ethanol at a concentration of 5 mg/mL, placing the avocados on drying racks, and allowing the avocados to dry under ambient room conditions at a temperature in the range of about 23° C.-27° C. and humidity in the range of about 40%-55%. The avocados were held at these same temperature and humidity conditions for the entire duration of the time they were tested.

As shown, the shelf life factor tended to increase as the carbon chain length of the 1-monoacylglyceride was increased. For example, all mixtures having a 1-monoacylglyceride with a carbon chain length greater than 13 exhibited a shelf life factor great than 1.2, all mixtures having a 1-monoacylglyceride with a carbon chain length greater than 15 exhibited a shelf life factor great than 1.35, and all mixtures having a 1-monoacylglyceride with a carbon chain length greater than 17 exhibited a shelf life factor great than 1.6.

Figure 16:
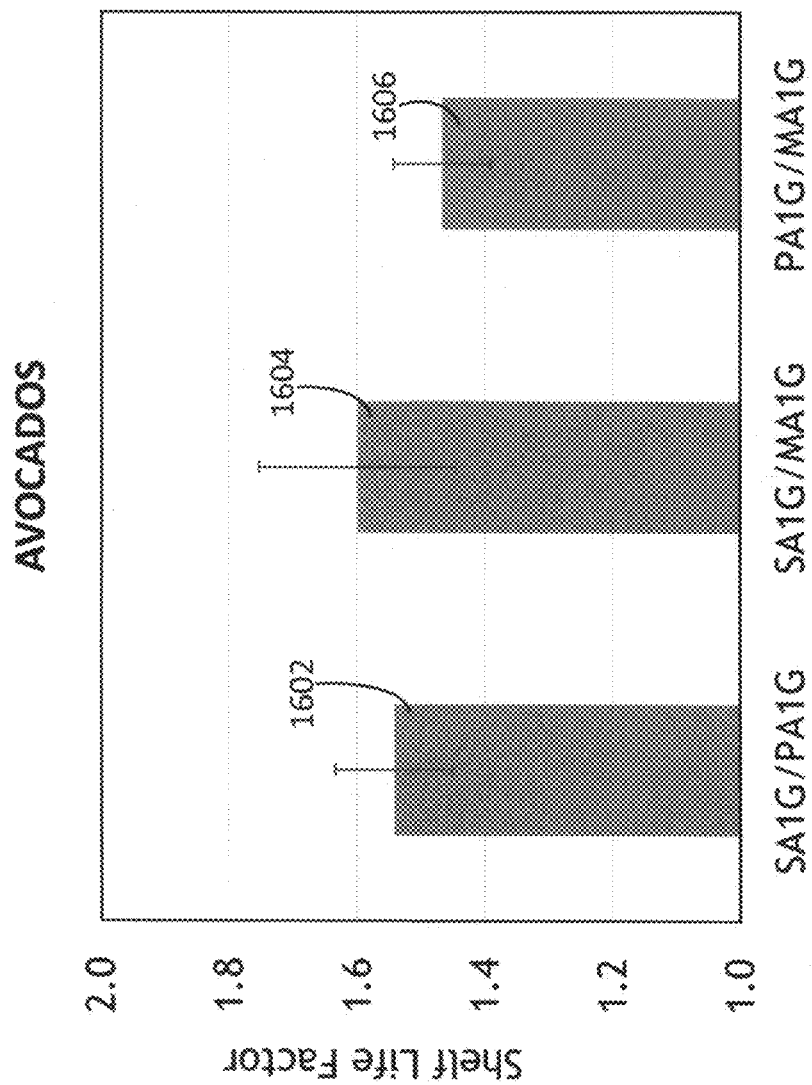
FIG. 16 shows a plot of the shelf life factor for avocados coated with mixtures of 1-glycerol esters of stearic acid, palmitic acid, and myristic acid.

FIG. 16 is a graph showing the shelf life factor for avocados each coated with a mixture including two different compounds of Formula II, mixed at a 1:1 mole ratio, where for each mixture the 2 compounds of Formula II have a different length carbon chain. Bar 1602 corresponds to a mixture of SA-1G (C18) and PA-1G (C16), bar 1604 corresponds to a mixture of SA-1G (C18) and MA-1G (C14), and bar 1606 corresponds to a mixture of PA-1G (C16) and MA-1G (C14). Each bar in the graph represents a group of 30 avocados. All coatings were formed by dipping the avocados in a solution comprising the associated mixture dissolved in substantially pure ethanol at a concentration of 5 mg/mL, placing the avocados on drying racks, and allowing the avocados to dry under ambient room conditions at a temperature in the range of about 23° C.-27° C. and humidity in the range of about 40%-55%. The avocados were held at these same temperature and humidity conditions for the entire duration of the time they were tested. As shown, the PA-1G/MA-1G mixture (1606) resulted in a shelf life factor greater than 1.4, the SA-1G/PA-1G mixture (1602) resulted in a shelf life factor greater than 1.5, and the SA-1G/MA-1G mixture (1604) resulted in a shelf life factor of about 1.6.

Figure 17:
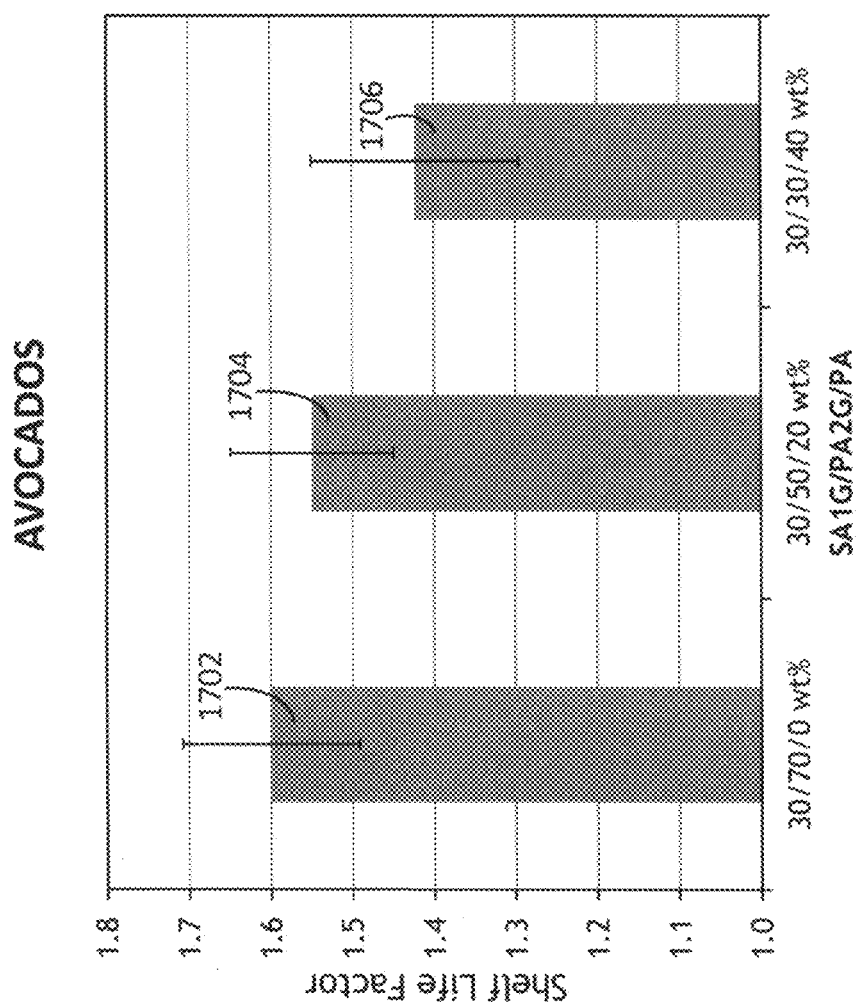
FIG. 17 shows a plot of the shelf life factor for avocados coated with mixtures comprising a combination of palmitic acid, 2-glycerol esters of palmitic acid, and 1-glycerol esters of stearic acid.
Figure 18:
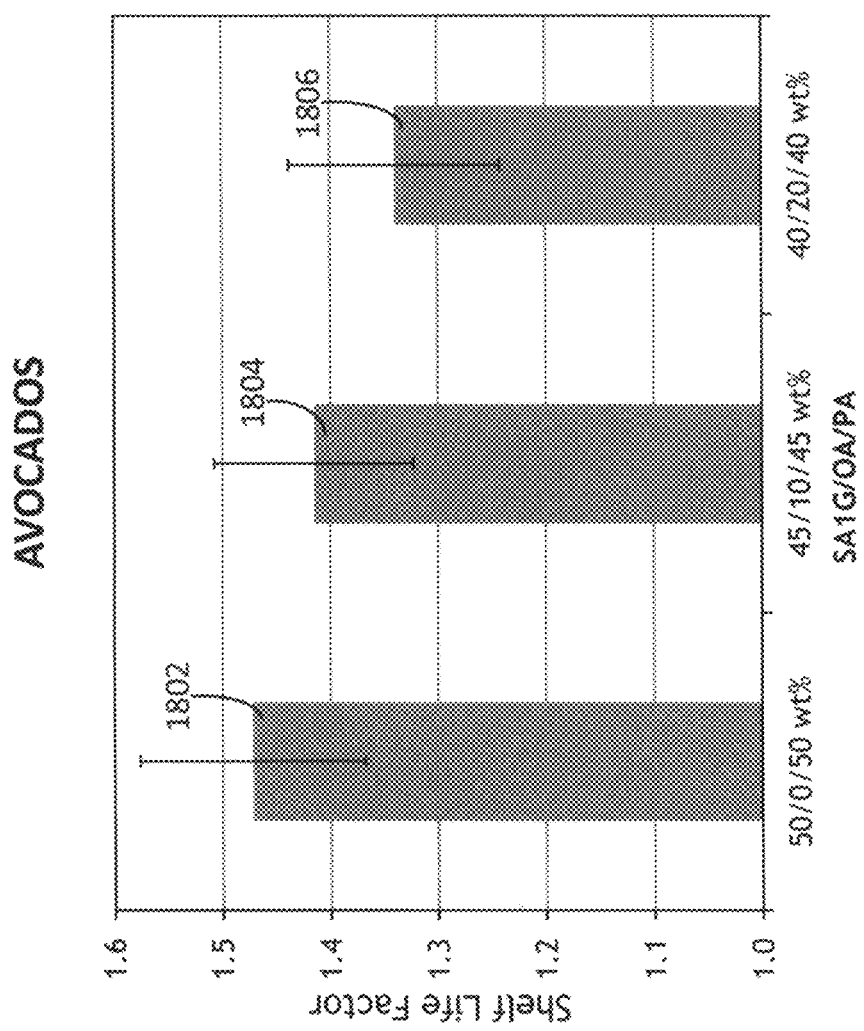
FIG. 18 shows a plot of the shelf life factor for avocados coated with mixtures comprising a combination of palmitic acid, oleic acid, and 1-glycerol esters of stearic acid.

FIGS. 17 and 18 are graphs showing the shelf life factor for avocados coated with binary or ternary compound mixtures. Each bar in both graphs represents a group of 30 avocados. All coatings were formed by dipping the avocados in a solution comprising the associated mixture dissolved in substantially pure ethanol at a concentration of 5 mg/mL, placing the avocados on drying racks, and allowing the avocados to dry under ambient room conditions at a temperature in the range of about 23° C.-27° C. and humidity in the range of about 40%-55%. The avocados were held at these same temperature and humidity conditions for the entire duration of the time they were tested.

The study illustrated in FIG. 17 was directed to examining the effects of adding a second additive to a mixture including a compound of Formula I and a first additive (the first additive being different from the second additive) in order to reduce the relative amount of the compound of Formula I in the mixture while still maintaining an effective coating with no visible precipitates or other visible residues. Because in some embodiments compounds of Formula I can be more expensive to produce and can be less stable (e.g., can convert to other types of compounds over time due to equilibrium driving forces) than other types of compounds (e.g., fatty acids and compounds of Formula II), reducing the relative composition of the compound of Formula I in the mixture can in some embodiments reduce the cost as well as increase the stability of the mixture.

Bar 1702 corresponds to avocados coated with a mixture including SA-1G (first additive, compound of Formula II) and PA-2G (compound of Formula I) mixed at a mass ratio of 30:70 (28:72 molar ratio). This coating resulted in a shelf life factor of about 1.6, and the coating was also free of any visible precipitates or other visible residues. Bar 1704 corresponds to avocados coated with a mixture including SA-1G, PA-2G, and PA mixed at a respective mass ratio of 30:50:20 (27:48:25 molar ratio). That is, as compared to the compounds corresponding to bar 1702, the coating formulation of bar 1704 could be formed by removing a portion of the PA-2G in the formulation corresponding to bar 1702 and replacing it with PA, such that the formulation of bar 1704 was 50% compounds of Formula I (by mass) and 50% additives (by mass) (48:52 molar ratio). As shown, the shelf life factor is only reduced slightly (as compared to bar 1702) to about 1.55, and the coating was found to be free of visible precipitates and other visible residues. Bar 1706 corresponds to avocados coated with a mixture including SA-1G, PA-2G, and PA mixed at a respective mass ratio of 30:30:40 (i.e., removing additional PA-2G and replacing it with PA) (25:27:47 molar ratio). In this case, the formulation was only 30% compounds of Formula I (by mass) and 70% additives (by mass) (27:73 molar ratio). As shown, although the shelf life factor is reduced (as compared to bars 1702 and 1704) to about 1.43, this coating formulation was still highly effective at reducing the rate of mass loss in avocados, and the coating was also found to be free of visible precipitates and other visible residues.

As previously described, 2-component mixtures which lacked a compound of Formula I could be made which resulted in coatings that reduced moisture loss and were also free of visible precipitates and other visible residues. However, in some embodiments the process window for these mixtures can be narrow, and small variations in composition, conditions during drying, or other process variables tended to result in the formation of visible precipitates or residues. FIG. 18 illustrates the results of a study directed to forming coatings with 3-component mixtures that lacked a compound of Formula I, and for which a wide range of composition variations could still result in coatings which provided an effective barrier to moisture loss while at the same time being free of visible precipitates and other visible residues. Bar 1802 corresponds to avocados coated with a mixture including SA-1G (compound of Formula II) and PA (first fatty acid) mixed at a mass ratio of 50:50 (42:58 molar ratio). The shelf life factor for these avocados was about 1.47. Although the coatings did not form any visible precipitates or other visible residues, small variations from this 50:50 mass ratio were found to cause visible precipitates/residues.

Bar 1804 corresponds to avocados coated with a mixture including SA-1G, OA, and PA mixed at a respective mass ratio of 45:10:45 (37:11:52 molar ratio). That is, as compared to the compounds corresponding to bar 1802, the coating formulation of bar 1804 could be formed by removing equal portions (by mass) of the SA-1G and PA in the formulation of bar 1802 and replacing them with OA. The shelf life factor for these avocados was still greater than 1.4, and no visible precipitates or other residues could be detected. Furthermore, this combination was substantially less sensitive to variations in formulation composition and process conditions as compared to the binary compound mixture of bar 1802; modest variations in composition or process conditions did not result in formation of visible precipitates or other visible residues, and the water barrier properties of the coatings were maintained.

Bar 1806 corresponds to avocados coated with a mixture including SA-1G, OA, and PA mixed at a respective mass ratio of 40:20:40 (33:21:46 molar ratio). That is, as compared to the compounds corresponding to bar 1804, the coating formulation of bar 1804 could be formed by further removing equal portions (by mass) of the SA-1G and PA in the formulation of bar 1804 and replacing them with OA. The shelf life factor for these avocados was greater than 1.3, and no visible precipitates or other residues could be detected. Furthermore, as with the combination of bar 1804, this combination was substantially less sensitive to variations in formulation composition and process conditions as compared to the binary compound mixture of bar 1802; modest variations in composition or process conditions did not result in formation of visible precipitates or other visible residues, and the water barrier properties of the coatings were maintained

EQUIVALENTS

Various implementations of the compositions and methods have been described above. However, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modification are in accordance with the variations of the disclosure. The implementations have been particularly shown and described, but it will be understood that various changes in form and details may be made. Accordingly, other implementations are within the scope of the following claims.

The invention claimed is:

1. A composition consisting of:

a compound of Formula I:

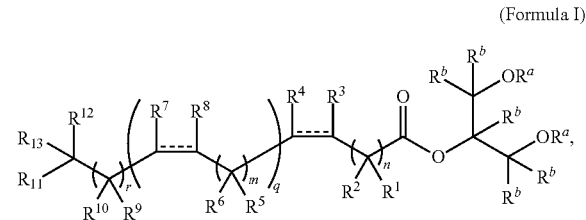

(Formula I)

and one or more additives, wherein at least one of the one or more additives comprises a compound of Formula II:

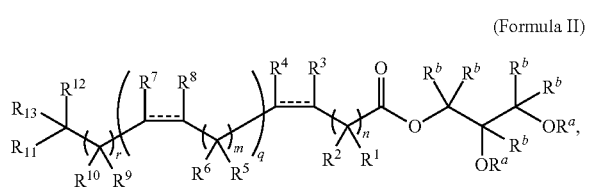

(Formula II)

wherein for each formula:

each $R^a$ is independently —H or —$C_1$-$C_6$alkyl;

each $R^b$ is independently selected from —H, —$C_1$-$C_6$alkyl, or —OH;

$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen;

$R^3$, $R^4$, $R^7$, and $R^8$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen; or $R^3$ and $R^4$ can combine with the carbon atoms to which they are attached to form a $C_3$-$C_6$ cycloalkyl, a $C_4$-$C_6$cycloalkenyl, or 3- to 6-membered ring heterocycle; and/or $R^7$ and $R^8$ can combine with the carbon atoms to which they are attached to form a $C_3$-$C_6$ cycloalkyl, a $C_4$-$C_6$cycloalkenyl, or 3- to 6-membered ring heterocycle;

$R^{14}$ and $R^{15}$ are each independently, at each occurrence, —H, —$C_1$-$C_6$alkyl, —$C_2$-$C_6$alkenyl, or —$C_2$-$C_6$alkynyl;

the symbol ====== represents a single bond or a cis or trans double bond;

n is 0, 1, 2, 3, 4, 5, 6, 7 or 8;

m is 0, 1, 2 or 3;

q is 0, 1, 2, 3, 4 or 5; and r is 0, 1, 2, 3, 4, 5, 6, 7 or 8;

wherein a molar ratio of the one or more additives to the compound of Formula I is in a range of 0.1 to 1, and the composition is formulated such that coatings formed from the composition are substantially free of visible residues.

2. The composition of claim 1, wherein a carbon chain length of the compound of Formula I is the same as a carbon chain length of the compound of Formula II.

3. The composition of claim 1, wherein a carbon chain length of the compound of Formula I is different from a carbon chain length of the compound of Formula II.

4. The composition of claim 1, wherein the compound of Formula I is selected from the group consisting of:

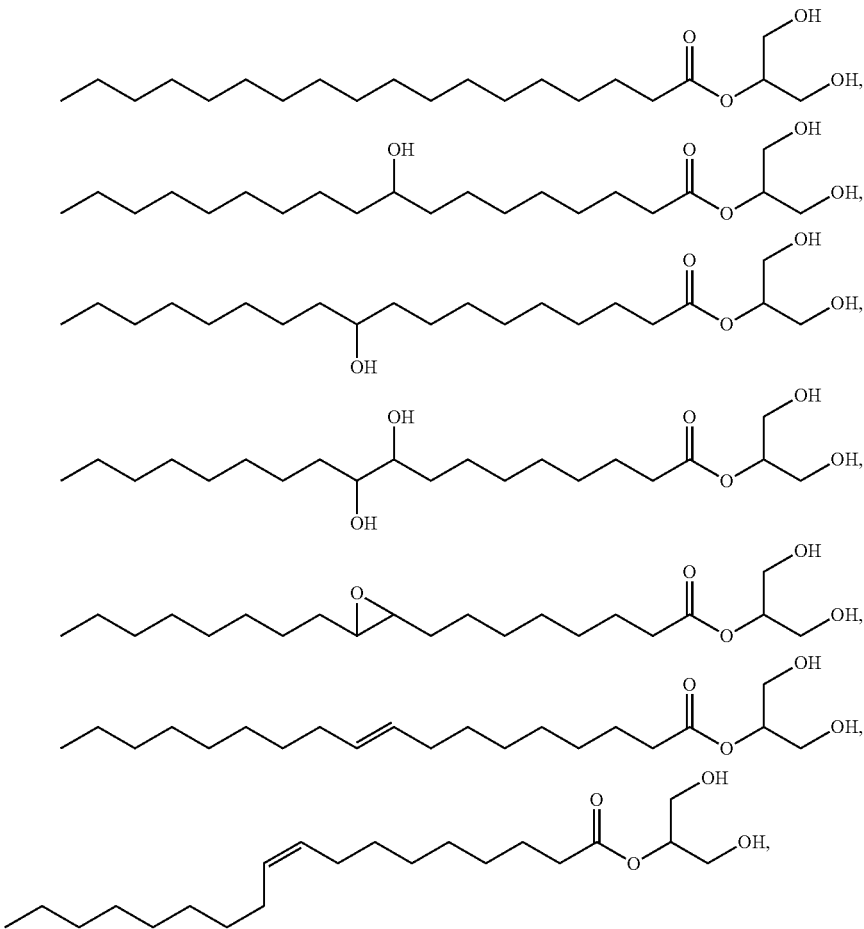

-continued
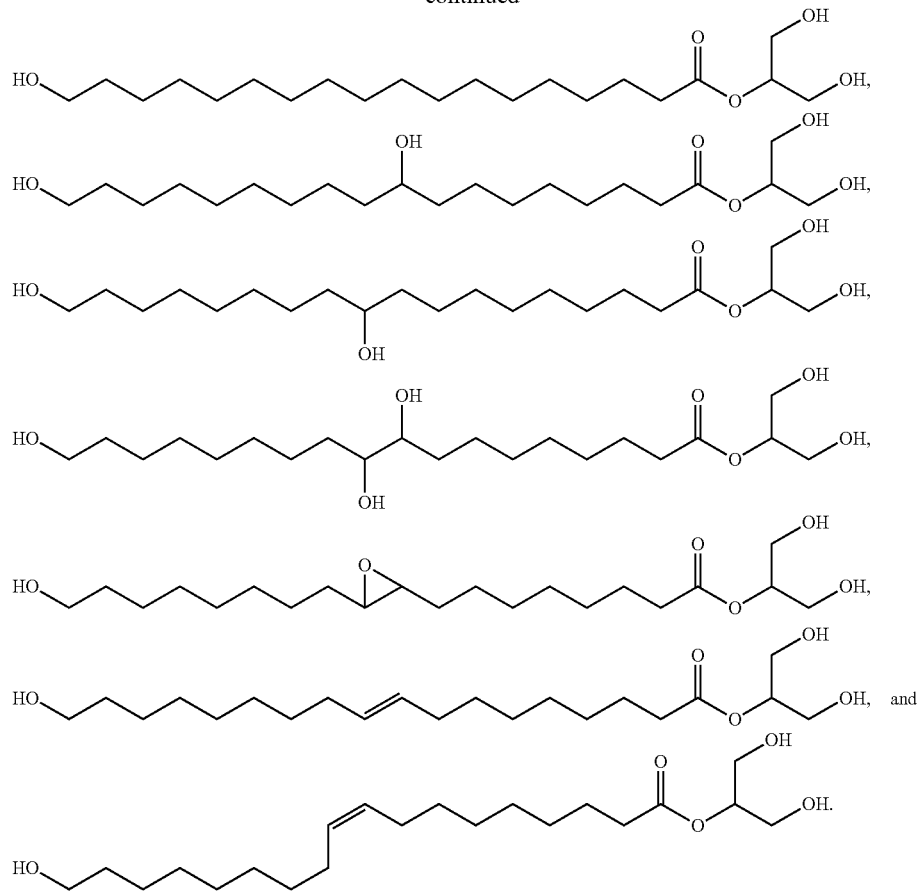
5. The composition of claim 1, wherein the compound of Formula I is selected from the group consisting of:
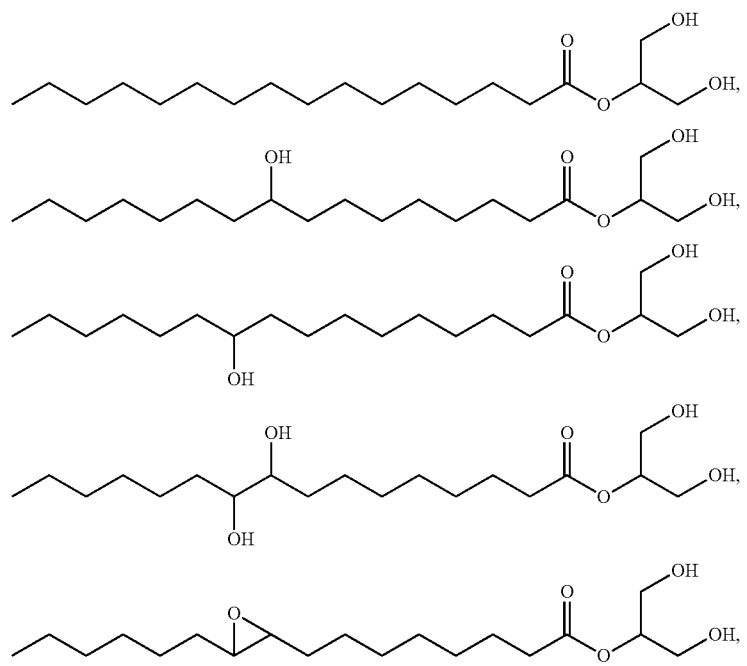

-continued

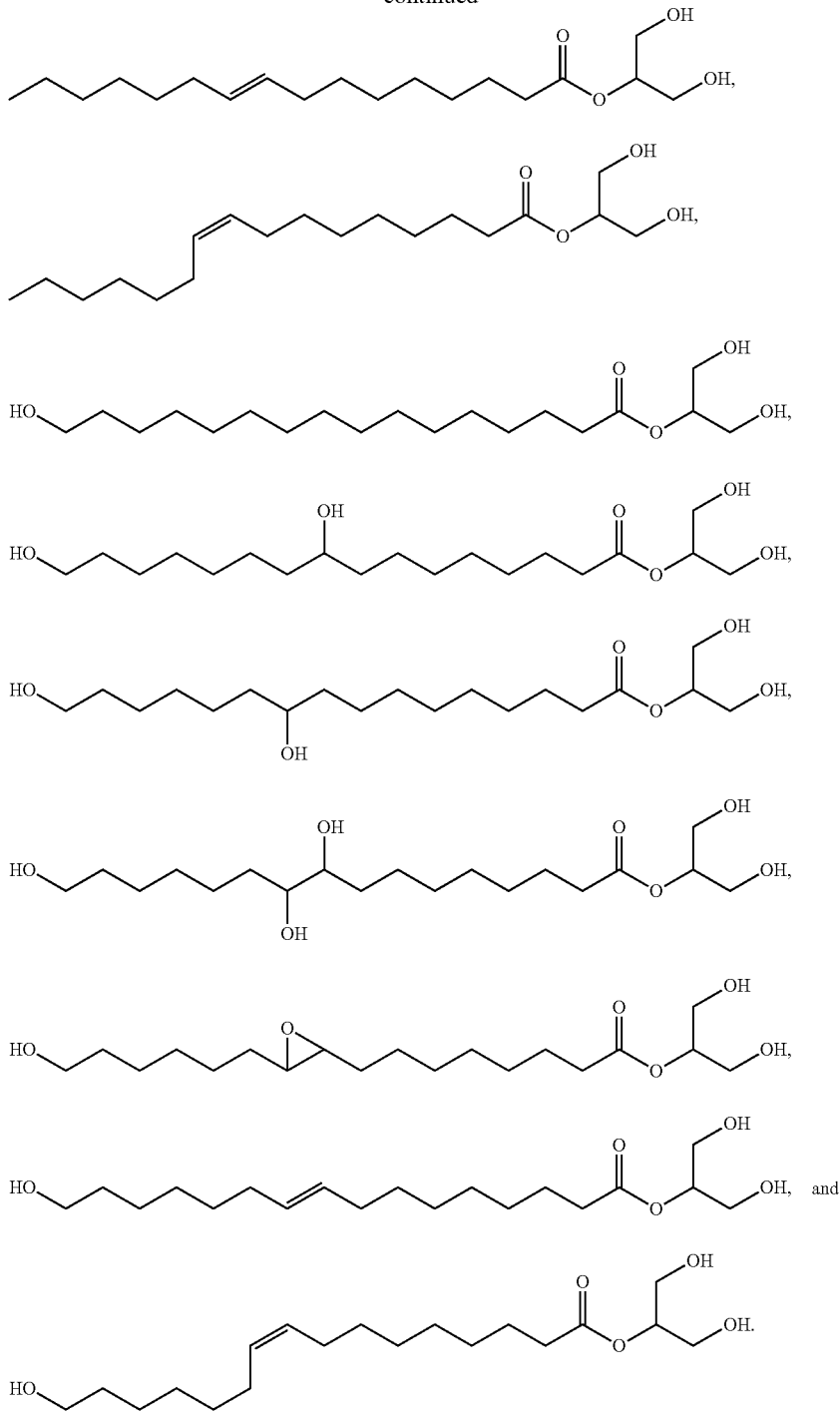

6. The composition of claim 1, wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ are each —H.

7. The composition of claim 1, wherein the one or more additives comprise a first additive and a second additive different from the first additive.

8. The composition of claim 7, wherein the first additive is a fatty acid and the second additive is the compound of Formula II.

9. The composition of claim 1, wherein the one or more additives comprise a fatty acid having a carbon chain length that is the same as a carbon chain length of the compound of Formula I.

10. The composition of claim 1, wherein the one or more additives comprise a fatty acid having a carbon chain length that is different from a carbon chain length of the compound of Formula I.

11. A mixture comprising a composition in a solvent, the composition consisting of:

a compound of Formula I:

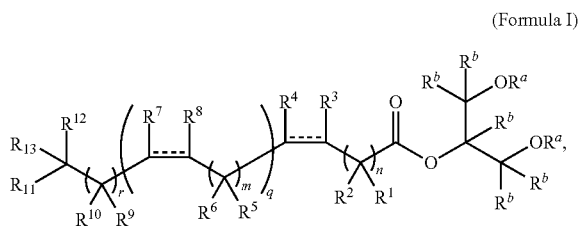

(Formula I)

and
one or more additives, wherein at least one of the one or more additives comprises a compound of Formula II:

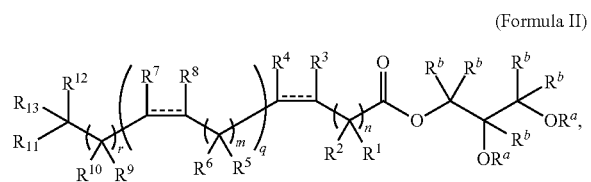

(Formula II)

wherein for each formula:
each $R^a$ is independently —H or —$C_1$-$C_6$alkyl;
each $R^b$ is independently selected from —H, —$C_1$-$C_6$alkyl, or —OH;
$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen;
$R^3$, $R^4$, $R^7$, and $R^8$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen; or
$R^3$ and $R^4$ can combine with the carbon atoms to which they are attached to form a $C_3$-$C_6$ cycloalkyl, a $C_4$-$C_6$cycloalkenyl, or 3- to 6-membered ring heterocycle; and/or
$R^7$ and $R^8$ can combine with the carbon atoms to which they are attached to form a $C_3$-$C_6$ cycloalkyl, a $C_4$-$C_6$cycloalkenyl, or 3- to 6-membered ring heterocycle;
$R^{14}$ and $R^{15}$ are each independently, at each occurrence, —H, —$C_1$-$C_6$alkyl, —$C_2$-$C_6$alkenyl, or —$C_2$-$C_6$alkynyl;
the symbol ══════ represents a single bond or a cis or trans double bond;
n is 0, 1, 2, 3, 4, 5, 6, 7 or 8;
m is 0, 1, 2 or 3;
q is 0, 1, 2, 3, 4 or 5; and
r is 0, 1, 2, 3, 4, 5, 6, 7 or 8;
wherein a molar ratio of the one or more additives to the compound of Formula I is in a range of 0.1 to 1, and the composition is formulated such that coatings formed from the composition are substantially free of visible residues; and
wherein the composition has a concentration in the solvent of at least 0.5 mg/mL.

12. The mixture of claim 11, wherein the solvent comprises water or ethanol.

13. The composition of claim 1, wherein the molar ratio of the one or more additives to the compound of Formula I is in a range of about 0.1 to about 0.5.

14. The composition of claim 13, wherein the molar ratio of the one or more additives to the compound of Formula I is in a range of about 0.2 to about 0.4.

15. The mixture of claim 11, wherein a carbon chain length of the compound of Formula I is the same as a carbon chain length of the compound of Formula II.

16. The mixture of claim 11, wherein a carbon chain length of the compound of Formula I is different from a carbon chain length of the compound of Formula II.

17. The mixture of claim 11, wherein the compound of Formula I is selected from the group consisting of:

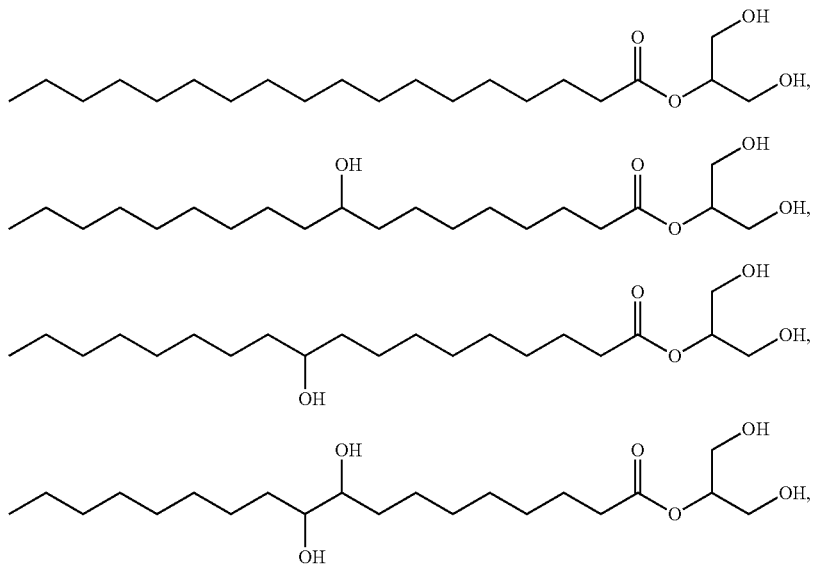

-continued
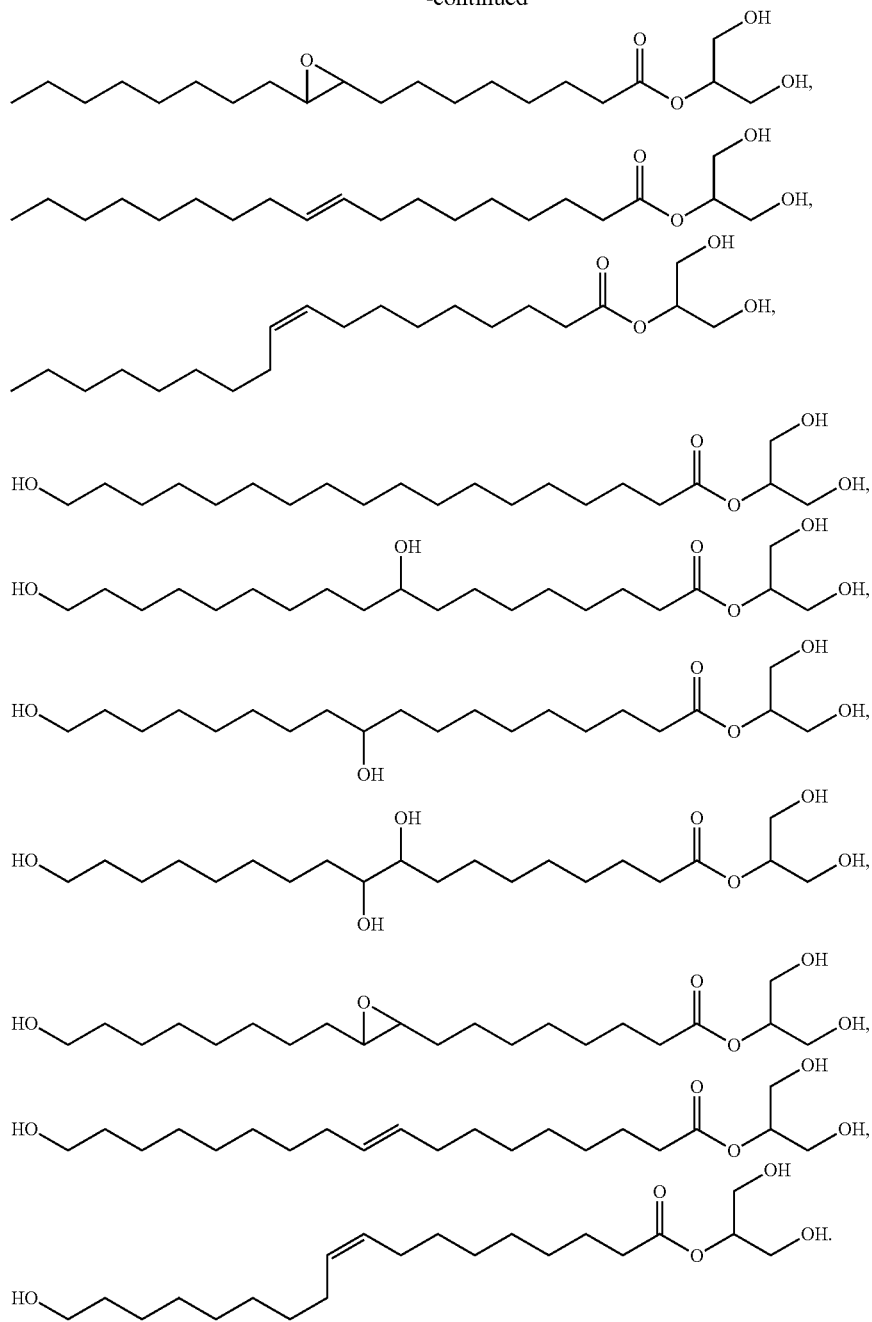
18. The mixture of claim 11, wherein the compound of Formula I is selected from the group consisting of:
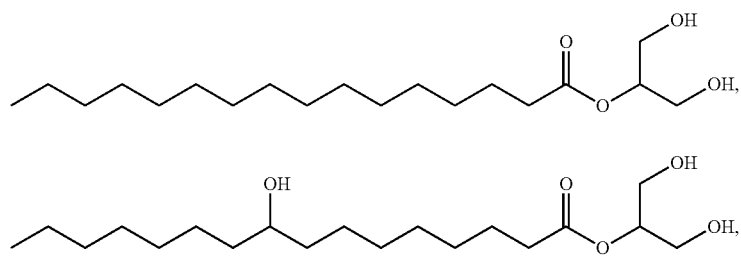

-continued
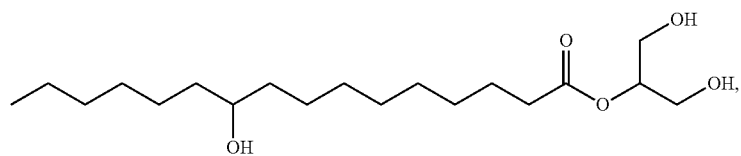
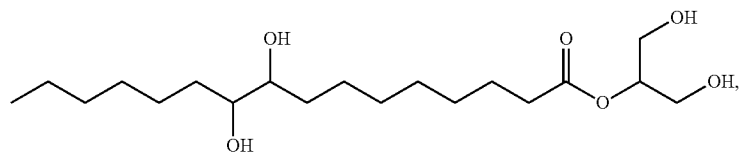
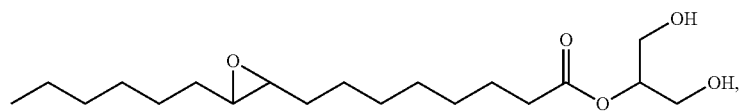
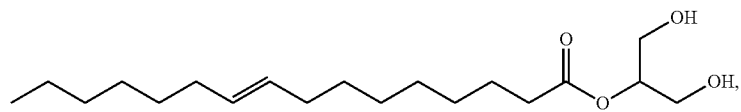
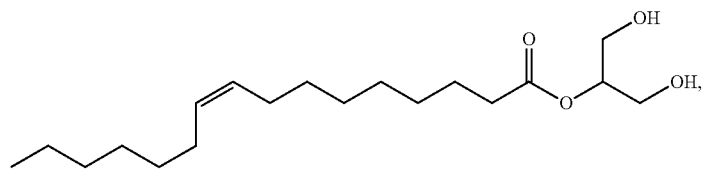
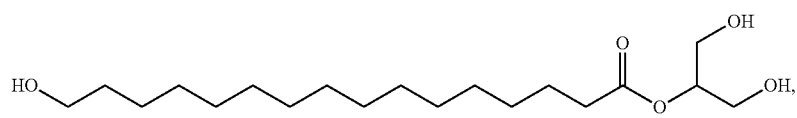
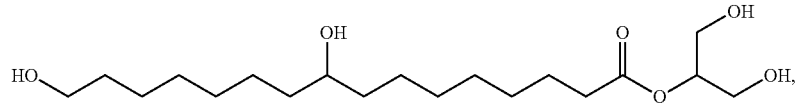
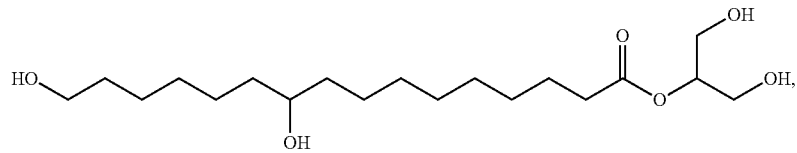
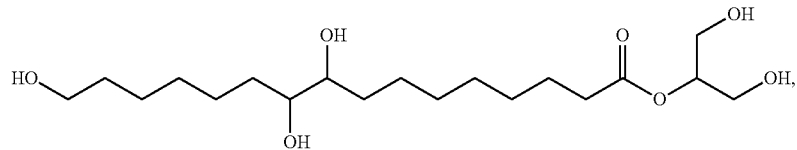
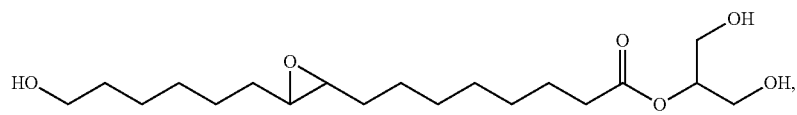
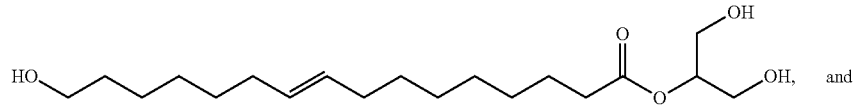 and -continued

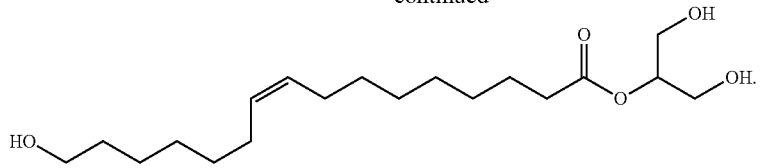

19. The mixture of claim 11, wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ are each —H.

20. The mixture of claim 11, wherein the one or more additives further comprise a fatty acid.

21. The mixture of claim 11, wherein the one or more additives comprise a fatty acid having a carbon chain length that is the same as a carbon chain length of the compound of Formula I.

22. The mixture of claim 11, wherein the one or more additives comprise a fatty acid having a carbon chain length that is different from a carbon chain length of the compound of Formula I.

23. The mixture of claim 11, wherein the molar ratio of the one or more additives to the compound of Formula I is in a range of about 0.1 to about 0.5.

24. The mixture of claim 11, wherein the molar ratio of the one or more additives to the compound of Formula I is in a range of about 0.2 to about 0.4.

25. A composition consisting of:
a compound of Formula I:

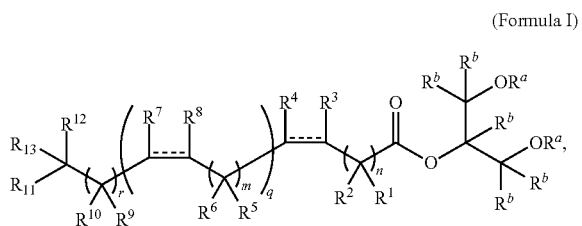

(Formula I)

and
an additive comprising one or more additives, wherein at least one of the one or more additives comprises a compound of Formula II:

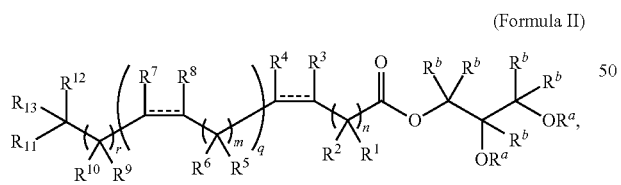

(Formula II)

wherein for each formula:
each $R^a$ is independently —H or —$C_1$-$C_6$alkyl;
each $R^b$ is independently selected from —H, —$C_1$-$C_6$alkyl, or —OH;
$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen;
$R^3$, $R^4$, $R^7$, and $R^8$ are each independently, at each occurrence, —H, —$OR^{14}$, —$NR^{14}R^{15}$, —$SR^{14}$, halogen, —$C_1$-$C_6$alkyl, —$C_2$-$C_6$alkenyl, —$C_2$-$C_6$alkynyl, —$C_3$-$C_7$cycloalkyl, aryl, or heteroaryl wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen; or
$R^3$ and $R^4$ can combine with the carbon atoms to which they are attached to form a $C_3$-$C_6$ cycloalkyl, a $C_4$-$C_6$cycloalkenyl, or 3- to 6-membered ring heterocycle; and/or
$R^7$ and $R^8$ can combine with the carbon atoms to which they are attached to form a $C_3$-$C_6$ cycloalkyl, a $C_4$-$C_6$cycloalkenyl, or 3- to 6-membered ring heterocycle;
$R^{14}$ and $R^{15}$ are each independently, at each occurrence, —H, —$C_1$-$C_6$alkyl, —$C_2$-$C_6$alkenyl, or —$C_2$-$C_6$alkynyl;
the symbol ===== represents a single bond or a cis or trans double bond;
n is 0, 1, 2, 3, 4, 5, 6, 7 or 8;
m is 0, 1, 2 or 3;
q is 0, 1, 2, 3, 4 or 5; and
r is 0, 1, 2, 3, 4, 5, 6, 7 or 8; wherein
a molar ratio of the one or more additives to the compound of Formula I is in a range of 0.1 to 1;
the compound of Formula I is selected from the group consisting of 2-glycero palmitate, 2-glycero stearate, 2-glycero myristate, and 2-glycero oleate; and
the compound of Formula II is selected from the group consisting of 1-glycero palmitate, 1-glycero stearate, 1-glycero myristate, and 1-glycero oleate.

* * * * *